United States Patent
Hezi-Yamit et al.

(10) Patent No.: US 11,338,140 B2
(45) Date of Patent: May 24, 2022

(54) MONITORING OF NEUROMODULATION USING BIOMARKERS

(71) Applicant: Medtronic Ardian Luxembourg S.a.r.l., Luxembourg (LU)

(72) Inventors: Ayala Hezi-Yamit, Santa Rosa, CA (US); Rudy Beasley, Santa Rosa, CA (US); Susan Edwards, Santa Rosa, CA (US); Lori Garcia, Santa Rosa, CA (US); Michele Lee Silver, Santa Rosa, CA (US); Christopher W. Storment, Santa Rosa, CA (US); Carol M. Sullivan, Santa Rosa, CA (US); Joseph A. Traina, Santa Rosa, CA (US); Stefan Stoyanov Tunev, Santa Rosa, CA (US)

(73) Assignee: MEDTRONIC ARDIAN LUXEMBOURG S.A.R.L., Luxembourg (LU)

(*) Notice: Subject to any disclaimer, the term of this patent is extended or adjusted under 35 U.S.C. 154(b) by 632 days.

(21) Appl. No.: 15/667,901

(22) Filed: Aug. 3, 2017

(65) Prior Publication Data

US 2018/0042535 A1     Feb. 15, 2018

Related U.S. Application Data

(63) Continuation of application No. 15/296,925, filed on Oct. 18, 2016, now Pat. No. 10,368,791, which is a
(Continued)

(51) Int. Cl.
*A61B 5/145* (2006.01)
*A61B 18/14* (2006.01)
(Continued)

(52) U.S. Cl.
CPC ........ *A61N 1/3606* (2013.01); *A61B 5/14546* (2013.01); *A61B 5/15003* (2013.01);
(Continued)

(58) Field of Classification Search
CPC .............. A61B 10/0045; A61B 10/007; A61B 2018/00511; A61B 2018/00577;
(Continued)

(56) References Cited

U.S. PATENT DOCUMENTS 2,130,758 A   9/1938 Rose
2,276,995 A   3/1942 Milinowski
(Continued)

FOREIGN PATENT DOCUMENTS

CN    101489624    7/2009
DE    3151180 A1   8/1982
(Continued)

OTHER PUBLICATIONS

Allen, E.V., Sympathectomy for essential hypertension, Circulation, 1952, 6:131-140.
(Continued)

*Primary Examiner* — Michael W Kahelin
*Assistant Examiner* — Pamela M. Bays
(74) *Attorney, Agent, or Firm* — Shumaker & Sieffert, P.A.

(57) ABSTRACT

Provided herein are methods, devices, compositions, and kits for monitoring neuromodulation efficacy based on changes in the level or activity of one or more target biomarkers. One aspect includes a comparison of baseline and post-modulation levels of one or more biomarkers in bodily fluid that have each been collected from a human subject at a relevant time, and that may be used to assess the neuromodulation efficacy. The post-neuromodulation levels for the one or more biomarkers may be collected from the human subject within about 5 minutes to about 14 days post-neuromodulation.

16 Claims, 45 Drawing Sheets

Related U.S. Application Data continuation of application No. 13/791,681, filed on Mar. 8, 2013, now Pat. No. 9,510,777.

(60) Provisional application No. 61/608,625, filed on Mar. 8, 2012, provisional application No. 61/608,626, filed on Mar. 8, 2012, provisional application No. 61/746,528, filed on Dec. 27, 2012.

(51) Int. Cl.

| | | |
|---|---|---|
| *A61B 5/00* | (2006.01) | |
| *A61B 18/02* | (2006.01) | |
| *A61N 1/36* | (2006.01) | |
| *A61B 18/00* | (2006.01) | |
| *A61N 1/05* | (2006.01) | |
| *A61B 5/20* | (2006.01) | |
| *A61B 5/15* | (2006.01) | |
| *A61B 5/157* | (2006.01) | |
| *A61B 10/00* | (2006.01) | |
| *A61B 18/18* | (2006.01) | |
| *A61N 1/32* | (2006.01) | |
| *G01N 33/68* | (2006.01) | |
| *A61N 1/40* | (2006.01) | |
| *A61N 7/02* | (2006.01) | |

(52) U.S. Cl.
CPC .......... *A61B 5/201* (2013.01); *A61B 5/4848* (2013.01); *A61B 18/1492* (2013.01); *A61N 1/0551* (2013.01); *A61N 1/3605* (2013.01); *A61N 1/36121* (2013.01); *A61B 5/1405* (2013.01); *A61B 5/14503* (2013.01); *A61B 5/15* (2013.01); *A61B 5/157* (2013.01); *A61B 5/150229* (2013.01); *A61B 5/150992* (2013.01); *A61B 5/20* (2013.01); *A61B 5/4035* (2013.01); *A61B 5/4836* (2013.01); *A61B 5/6851* (2013.01); *A61B 5/6852* (2013.01); *A61B 5/6853* (2013.01); *A61B 5/6858* (2013.01); *A61B 10/007* (2013.01); *A61B 10/0045* (2013.01); *A61B 18/02* (2013.01); *A61B 18/18* (2013.01); *A61B 2018/0022* (2013.01); *A61B 2018/00166* (2013.01); *A61B 2018/00214* (2013.01); *A61B 2018/00232* (2013.01); *A61B 2018/00279* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00875* (2013.01); *A61B 2018/0212* (2013.01); *A61N 1/05* (2013.01); *A61N 1/32* (2013.01); *A61N 1/36007* (2013.01); *A61N 1/36135* (2013.01); *A61N 1/40* (2013.01); *A61N 7/02* (2013.01); *G01N 33/68* (2013.01); *G01N 2800/347* (2013.01)

(58) Field of Classification Search
CPC ........ A61B 2018/00345; A61B 5/1405; A61B 5/201; A61B 5/15003; A61B 5/14546; A61B 5/4848; A61N 18/1492; A61N 1/3605; A61N 1/36121; A61N 1/3606; A61N 1/0551

See application file for complete search history.

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,444,203 A | 4/1984 | Engelman et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,764,504 A | 8/1988 | Johnson et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |

(56) References Cited

U.S. PATENT DOCUMENTS

| | | |
|---|---|---|
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,301,683 A | 4/1994 | Durkan |
| 5,304,120 A | 4/1994 | Crandell et al. |
| 5,304,206 A | 4/1994 | Baker, Jr. et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Ri |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,608,519 A | 3/1997 | Gourley et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster et al. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,004,269 A | 12/1999 | Crowley et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh et al. |
| 6,026,326 A | 2/2000 | Bardy |
| 6,036,687 A | 3/2000 | Laufer et al. |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,099,524 A | 8/2000 | Lipson et al. |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,142,993 A | 11/2000 | Whayne et al. |
| 6,146,380 A | 11/2000 | Racz et al. |
| 6,149,620 A | 11/2000 | Baker et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |

(56) References Cited

U.S. PATENT DOCUMENTS

| | | |
|---|---|---|
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,283,951 B1 | 9/2001 | Flaherty et al. |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,685,648 B2 | 2/2004 | Flaherty et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,711,444 B2 | 3/2004 | Koblish |
| 6,718,208 B2 | 4/2004 | Hill et al. |
| 6,735,471 B2 | 5/2004 | Hill et al. |
| 6,736,835 B2 | 5/2004 | Pellegrino et al. |
| 6,738,663 B2 | 5/2004 | Schroeppel et al. |
| 6,749,598 B1 | 6/2004 | Keren et al. |
| 6,752,805 B2 | 6/2004 | Maguire et al. |
| 6,786,904 B2 | 9/2004 | Doscher et al. |
| 6,795,728 B2 | 9/2004 | Chomenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,916,656 B2 | 7/2005 | Walters et al. |
| 6,917,834 B2 | 7/2005 | Koblish et al. |
| 6,923,808 B2 | 8/2005 | Taimisto |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,949,097 B2 | 9/2005 | Stewart et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,149,574 B2 | 12/2006 | Yun et al. |
| 7,155,284 B1 | 12/2006 | Whitehurst et al. |
| 7,160,296 B2 | 1/2007 | Pearson et al. |
| 7,162,303 B2 | 1/2007 | Levin et al. |
| 7,191,015 B2 | 3/2007 | Lamson et al. |
| 7,221,979 B2 | 5/2007 | Zhou et al. |
| 7,373,204 B2 | 5/2008 | Gelfand et al. |
| 7,381,200 B2 | 6/2008 | Katoh et al. |
| 7,390,894 B2 | 6/2008 | Weinshilboum et al. |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,702,619 B2 | 4/2014 | Wang |
| 8,768,470 B2 | 7/2014 | Deem et al. |
| 8,888,773 B2 | 11/2014 | Chang et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel et al. |
| 9,014,821 B2 | 4/2015 | Wang |
| 9,022,948 B2 | 5/2015 | Wang |

(56) References Cited

U.S. PATENT DOCUMENTS

| | | |
|---|---|---|
| 9,119,600 B2 | 9/2015 | Richardson et al. |
| 9,168,094 B2 | 10/2015 | Lee et al. |
| 9,179,973 B2 | 11/2015 | Nabutovsky et al. |
| 9,186,212 B2 | 11/2015 | Nabutovsky et al. |
| 9,295,842 B2 | 3/2016 | Ghaffari et al. |
| 9,314,300 B2 | 4/2016 | Nabutovsky et al. |
| 9,375,154 B2 | 6/2016 | Wang |
| 9,427,283 B2 | 8/2016 | Nabutovsky et al. |
| 9,427,579 B2 | 8/2016 | Fain et al. |
| 9,554,850 B2 | 1/2017 | Lee et al. |
| 9,579,030 B2 | 2/2017 | Scheuermann et al. |
| 10,537,734 B2 | 1/2020 | Zarins |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Muller et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0116401 A1* | 6/2004 | Shah ............... A61K 31/444 514/183 |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0153379 A1 | 7/2005 | Hoon et al. |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |

(56) References Cited

U.S. PATENT DOCUMENTS

| | | |
|---|---|---|
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0128174 A1* | 6/2007 | Kleinsek ............... A61P 35/00 424/93.7 |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0057590 A1 | 3/2008 | Urdea et al. |
| 2008/0091255 A1 | 4/2008 | Caparso et al. |
| 2008/0140150 A1 | 6/2008 | Zhou et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0105605 A1 | 4/2009 | Abreu |
| 2010/0010567 A1 | 1/2010 | Deem et al. |
| 2010/0057150 A1 | 3/2010 | Demarais et al. |
| 2010/0069888 A1 | 3/2010 | Solomon |
| 2010/0086948 A1 | 4/2010 | Gold et al. |
| 2010/0087716 A1 | 4/2010 | Nashed |
| 2010/0114244 A1 | 5/2010 | Manda et al. |
| 2010/0137860 A1 | 6/2010 | Demarais et al. |
| 2010/0137952 A1 | 6/2010 | Demarais et al. |
| 2010/0166739 A1 | 7/2010 | Chancellor et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2010/0331833 A1 | 12/2010 | Maschke et al. |
| 2011/0060324 A1 | 3/2011 | Wu et al. |
| 2011/0086257 A1 | 4/2011 | Pitteloud et al. |
| 2011/0112400 A1 | 5/2011 | Emery et al. |
| 2011/0137298 A1 | 6/2011 | Nguyen et al. |
| 2011/0152759 A1 | 6/2011 | Clymer et al. |
| 2011/0160644 A1 | 6/2011 | Dacey, Jr. et al. |
| 2011/0178570 A1* | 7/2011 | Demarais ............ A61N 1/0551 607/44 |
| 2011/0184337 A1 | 7/2011 | Evans et al. |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0270120 A1 | 11/2011 | McFarlin et al. |
| 2011/0306851 A1 | 12/2011 | Wang |
| 2012/0029504 A1 | 2/2012 | Alfonzo et al. |
| 2012/0116383 A1 | 5/2012 | Mauch |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172680 A1* | 7/2012 | Gelfand .................. A61N 1/06 600/301 |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0296232 A1 | 11/2012 | Ng |
| 2012/0296329 A1 | 11/2012 | Ng |
| 2013/0085489 A1 | 4/2013 | Fain et al. |
| 2013/0123778 A1 | 5/2013 | Richardson et al. |
| 2013/0165764 A1 | 6/2013 | Scheuermann et al. |
| 2013/0172878 A1 | 7/2013 | Subramaniam et al. |
| 2013/0178750 A1 | 7/2013 | Sheehan et al. |
| 2013/0218029 A1 | 8/2013 | Cholette et al. |
| 2013/0237948 A1 | 9/2013 | Donders et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0018656 A1 | 1/2015 | Min et al. |
| 2015/0025524 A1 | 1/2015 | Nabutovsky |
| 2015/0112329 A1 | 4/2015 | Ng |
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |
| 2015/0289770 A1 | 10/2015 | Wang |
| 2015/0289929 A1 | 10/2015 | Toth et al. |
| 2015/0366609 A1 | 12/2015 | Richardson et al. |
| 2016/0000345 A1 | 1/2016 | Kobayashi et al. |
| 2016/0015452 A1 | 1/2016 | Nabutovsky et al. |
| 2016/0029960 A1 | 2/2016 | Toth et al. |
| 2016/0038028 A1 | 2/2016 | Buelna et al. |
| 2016/0081744 A1 | 3/2016 | Wang |
| 2016/0095652 A1 | 4/2016 | Lee et al. |
| 2016/0106498 A1 | 4/2016 | Highsmith et al. |
| 2016/0184010 A1 | 6/2016 | Nabutovsky et al. |
| 2016/0213262 A1 | 7/2016 | Ghaffari et al. |
| 2016/0213424 A1 | 7/2016 | Ghaffari et al. |
| 2016/0324572 A1 | 11/2016 | Gross et al. |
| 2016/0331451 A1 | 11/2016 | Nabutovsky et al. |
| 2016/0331453 A1 | 11/2016 | Fain et al. |

(56) References Cited

U.S. PATENT DOCUMENTS

| | | |
|---|---|---|
| 2016/0374568 A1 | 12/2016 | Wang |
| 2017/0215950 A1 | 8/2017 | Gross et al. |

FOREIGN PATENT DOCUMENTS

| | | |
|---|---|---|
| EP | 0811395 A2 | 12/1997 |
| EP | 1169976 | 1/2002 |
| EP | 2092957 A1 | 8/2009 |
| EP | 2316371 | 5/2011 |
| EP | 2594193 | 5/2013 |
| EP | 2613704 | 7/2013 |
| EP | 2747691 | 7/2014 |
| EP | 2852339 | 4/2015 |
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3011899 | 4/2016 |
| EP | 3028628 | 6/2016 |
| EP | 3089686 | 11/2016 |
| EP | 2709517 | 1/2017 |
| JP | H08504531 | 5/1996 |
| JP | H1071037 | 3/1998 |
| JP | 2001518808 | 10/2001 |
| JP | 2005278739 | 10/2005 |
| JP | 2008515544 | 5/2008 |
| JP | 2009539565 | 11/2009 |
| JP | 2010162163 | 7/2010 |
| JP | 2010533513 | 10/2010 |
| JP | 2011505929 | 3/2011 |
| WO | WO-1985001213 A1 | 3/1985 |
| WO | 2014091328 | 7/1989 |
| WO | WO-1991004725 A1 | 4/1991 |
| WO | WO-1992020291 A1 | 11/1992 |
| WO | WO-1993002740 A1 | 2/1993 |
| WO | WO-1993007803 A1 | 4/1993 |
| WO | WO-1994000188 A1 | 1/1994 |
| WO | WO-1994007446 A1 | 4/1994 |
| WO | WO-1994011057 A1 | 5/1994 |
| WO | WO-1995025472 A1 | 9/1995 |
| WO | WO-1995031142 A1 | 11/1995 |
| WO | WO-1995033514 A1 | 12/1995 |
| WO | WO-1996000039 A1 | 1/1996 |
| WO | WO-1996004957 A1 | 2/1996 |
| WO | WO-1996011723 A1 | 4/1996 |
| WO | WO-1997013463 A1 | 4/1997 |
| WO | WO-1997013550 A1 | 4/1997 |
| WO | WO-1997036548 A1 | 10/1997 |
| WO | WO-1997049453 A1 | 12/1997 |
| WO | WO-1998037926 A1 | 9/1998 |
| WO | WO-1998042403 A1 | 10/1998 |
| WO | WO-1998043700 A1 | 10/1998 |
| WO | WO-1998043701 A1 | 10/1998 |
| WO | WO-1998048888 A1 | 11/1998 |
| WO | 1999000060 | 1/1999 |
| WO | WO-1999000060 A1 | 1/1999 |
| WO | WO-1999033407 A1 | 7/1999 |
| WO | WO-1999051286 A1 | 10/1999 |
| WO | WO-1999052424 A1 | 10/1999 |
| WO | WO-2001022897 A1 | 4/2001 |
| WO | WO-2001026729 | 4/2001 |
| WO | WO-2001070114 A1 | 9/2001 |
| WO | WO-2002009808 | 2/2002 |
| WO | WO-2002026314 | 4/2002 |
| WO | WO-2002053207 | 7/2002 |
| WO | WO-2002070039 | 9/2002 |
| WO | WO-2002070047 | 9/2002 |
| WO | WO-2002085192 | 10/2002 |
| WO | WO-2002085448 | 10/2002 |
| WO | WO-2003018108 | 3/2003 |
| WO | WO-2003022167 | 3/2003 |
| WO | WO-2003028802 | 4/2003 |
| WO | WO-2003063692 | 8/2003 |
| WO | WO-2003071140 | 8/2003 |
| WO | WO-2003076008 | 9/2003 |
| WO | WO-2003/082080 | 10/2003 |
| WO | WO-2003082080 | 10/2003 |
| WO | WO-2003082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005/014100 | 2/2005 |
| WO | WO-2005/016165 | 2/2005 |
| WO | WO-2005/032646 | 4/2005 |
| WO | WO-2005030072 A1 | 4/2005 |
| WO | WO-2005041748 A2 | 5/2005 |
| WO | WO-2005/065284 | 7/2005 |
| WO | WO-2005/084389 A2 | 9/2005 |
| WO | WO-2005/097256 A2 | 10/2005 |
| WO | WO-2005/110528 A1 | 11/2005 |
| WO | WO-2005/123183 | 12/2005 |
| WO | WO-2006/007048 A2 | 1/2006 |
| WO | WO-2006/018528 A1 | 2/2006 |
| WO | WO-2006/022790 | 3/2006 |
| WO | WO-2006/031899 A2 | 3/2006 |
| WO | WO-2006041847 | 4/2006 |
| WO | WO-2006041881 A2 | 4/2006 |
| WO | WO-2006105121 A2 | 10/2006 |
| WO | WO-2007008954 A2 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | 2008003058 | 1/2008 |
| WO | WO-2008003058 | 1/2008 |
| WO | WO-2008049084 A2 | 4/2008 |
| WO | WO-2008061150 | 5/2008 |
| WO | WO-2008061152 | 5/2008 |
| WO | WO-2008070413 | 6/2008 |
| WO | WO-2010078175 A1 | 7/2010 |
| WO | 2011089935 | 7/2011 |
| WO | 2012024543 | 2/2012 |
| WO | 2012068471 | 5/2012 |
| WO | 2013030743 | 3/2013 |
| WO | 2013112844 | 8/2013 |
| WO | 2014012282 | 1/2014 |
| WO | 2014029355 | 2/2014 |
| WO | 2014059165 | 4/2014 |
| WO | 2014068577 | 5/2014 |
| WO | 2014091401 | 6/2014 |
| WO | 2014149550 | 9/2014 |
| WO | 2014149552 | 9/2014 |
| WO | 2014149553 | 9/2014 |
| WO | 2014149690 | 9/2014 |
| WO | 2014150425 | 9/2014 |
| WO | 2014150432 | 9/2014 |
| WO | 2014150441 | 9/2014 |
| WO | 2014150455 | 9/2014 |
| WO | 2014158708 | 10/2014 |
| WO | 2014158713 | 10/2014 |
| WO | 2014163990 | 10/2014 |
| WO | 2014179768 | 11/2014 |
| WO | 2014182946 | 11/2014 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Cline, 2000, vol. 12, No. 4, pp. 323-327.

(56) References Cited

OTHER PUBLICATIONS

Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. Vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.

(56) References Cited

OTHER PUBLICATIONS

Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011,2 pages, <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages, <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009.1 page, <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.
Badger, Emilio, "Cardiacafferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal ofthe American College of Cardiology, vol. 62, No. 3, 2013, 11 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).

(56) References Cited

OTHER PUBLICATIONS

Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al., "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future dor Renal Denervation With Better Controlled Trials." Pharma & Medtech Business Intelligence, Article# 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129:1440-1450.
Papademetriou, Vasilios et al., "Catheter-Based Renal Denervation for Resistant Hypertension: 12-Month Results ofthe EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, Dec. 16, 2008, pp. 1.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): pp. 754-758.
Alford, J. Winslow, M.D. and Paul D. Fadale, M.D., Evaluation of Postoperative Bupivacaine Infusion for Pain Management After

(56) References Cited

OTHER PUBLICATIONS

Anterior Cruciate Ligament Reconstruction, The Journal of Arthroscopic and Related Surgery, vol. 19, No. 8, Oct. 2003 Arthroscopy Association of North America, pp. 855-861.

Amersham Health. Hypaque-Cysto, 2003, 6 pages.

Andrews, B.T. et al., The use of surgical sympathectomy in the treatment of chronic renal pain. Br J Urol. 1997; 80: 6-10.

Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.

Archer, Steffen et al., Cell Reactions to Dielectrophoretic Manipulation, Mar. 1, 1999, Biochemical and Biophysical Research Communications, 1999 Academic Press, pp. 687-698.

Arentz, T. et al., Incidence of pulmonary vein stenosis 2 years after radiofrequency catheter ablation of refractory atrial fibrillation. European Heart Journal. 2003. 24; pp. 963-969.

Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.

Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.

Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.

Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.

Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.

Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.

Badyal, D. K., H. Lata and A.P. Dadhich, Animal Models of Hypertension and Effect of Drugs, Aug. 19, 2003, Indian Journal of Pharmacology 2003, vol. 35, pp. 349-362.

Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.

Balazs, Tibor, Development of Tissue Resistance to Toxic Effects of Chemicals, Jan. 26, 1974, Toxicology, 2 (1974), Elsevier/North-Holland, Amsterdam, pp. 247-255.

Barajas, L. Innervation of the renal cortex. Fex Proc. 1978;37:1192-201.

Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.

Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.

Bassett, C. Andrew L. et al., Augmentation of Bone Repair by Inductively Coupled Electromagnetic Fields, May 3, 1974, Science, vol. 184, pp. 575-577.

Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.

Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.

Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.

Bello-Reuss, E. et al., Acute unilateral renal denervation in rats with extracellular volume expansion, Departments of Medicine and Physiology, University of North Carolina School of Medicine. F26-F32 Jul. 1975.

Bello-Reuss, E. et al., Effect of renal sympathetic nerve stimulation on proximal water and sodium reabsorption, J Clin Invest, 1976;57:1104-1107.

Bello-Reuss, E. et al., Effects of Acute Unilateral Renal Denervation in the Rat, J Clin Invest, 1975;56:208-217.

Berde, C. et al., Local Anesthetics, Anesthesia, Chapter 13, 5th addition, Churchill-Livingston, Philadelphia 2000, pp. 491-521.

Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.

Bhandari, A. and Ellias, M., Loin pain hematuria syndrome: Pain control with RFA to the Splanchanic plexus, The Pain Clinic, 2000, vol. 12, No. 4, pp. 323-327.

Bhatt, Deepak L. et al., Rhabdomyolysis Due to Pulsed Electric Fields, May 11, 1989, Plastic and Reconstructive Surgery Jul. 1990, pp. 1-11.

Bichet, D., et al., Renal intracortical blood flow and renin secretion after denervation by 6-hydroxydopamine. Can J Physiol Pharmacol. 1982;60:184-92.

Bigler, D. et al., Tachyphylaxis during postoperative epidural analgesia—new insights, Apr. 15, 1987, Letter to the Editor, Acta Anaesthesiol Scand. 1987, vol. 31, pp. 664-665.

Binder, Allan et al., Pulsed Electromagnetic Field Therapy of Persistent Rotator Cuff Tendinitis, The Lancet, Saturday Mar. 31, 1984, The Lancet Ltd., pp. 695-698.

Black, M.D., Henry R., Resistant Hypertension 2004, presentation at Rush University Medical Center, Jul. 15, 2004, 40 pages.

Blad, B., et al., An Electrical Impedance index to Assess Electroporation in Tissue, Tissue and Organ (Therapy), 2001, Oslo, www.bl.uk<http://www.bl.uk> British Library, pp. 31-34.

Blair, M. L. et al., Sympathetic activation cannot fully account for increased plasma renin levels during water deprivation, Sep. 23, 1996, Am. J. Physiol., vol. 272, 1997, the American Physiological Society 1997, pp. R1197-R1203.

Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.

Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.

Bourge, R.C., Heart Failure Monitoring Devices: Rationale and Status 28 pages, Feb. 2001.

Braunwald, E., Heart Disease, A Textbook of Cardiovascular Medicine, 5th Ed., vol. 2, 1997, pp. 480-481, 824-825, 1184-1288 and 1923-1925, W.B. Saunders Company.

Bravo, E.L., et al., Renal denervation for resistant hypertension, American Journal of Kidney Diseases, 2009, 3 pgs.

Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.

Burkhoff, D., Interventional Device-Based Therapy for CHF Will Redefine Current Treatment Paradigms. Columbia University. 2004. 32 slides.

Burns, J. et al., Relationship between central sympathetic drive and magnetic resonance imaging-determined left ventricular mass in essential hypertension. Circulation. 2007;115:1999-2005.

(56) References Cited

OTHER PUBLICATIONS

Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment For Chronic Heart Failure: Electrical Modulation of Myocardial Contractility. Transcatheter Cardiovascular Therapeutics 2005, 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.

Cosman, E.R., Jr et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical therapy for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.

(56) References Cited

OTHER PUBLICATIONS

Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
Dibona, Gerald F., Sympathetic Nervous System and the Kidney in Hypertension, Current Opinion in Nephrology and Hypertension 2002, vol. 11,2002 Lippincott Williams & Wilkins, pp. 197-200.
Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
Dibona, Gerald, LL Sawin, Effect of renal denervation on dynamic autoregulation of renal blood flow, Feb. 12, 2004, AmJ Physiol Renal Physiol 286, pp. F1209-1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; dated Jan. 19, 2010, 4 pgs.
European Examination Report; European Patent Application No. 09156661.2; Applicant: Ardian, Inc.; dated Jan. 19, 2010, 6 pgs.
European Search Report; European Patent Application No. 05806045.0; Applicant: Ardian, Inc.; dated Sep. 22, 2009, 8 pgs.
European Search Report; European Patent Application No. 05811851.4; Applicant: Ardian, Inc.; dated Oct. 1, 2009, 7 pgs.
European Search Report; European Patent Application No. 06847926.0; Applicant: Ardian, Inc.; dated Feb. 10, 2010, 6 pgs.
European Search Report; European Patent Application No. 07757925.8; Applicant: Ardian, Inc.; dated Apr. 29, 2010, 9 pgs.
European Search Report; European Patent Application No. 07798341.9; Applicant: Ardian, Inc.; dated Aug. 4, 2011; 6 pgs.
European Search Report; European Patent Application No. 07799148.7; Applicant: Ardian, Inc.; dated Jul. 23, 2009, 6 pgs.
European Search Report; European Patent Application No. 07868755.5; Applicant: Ardian, Inc.; dated Jul. 28, 2010, 7 pgs.
European Search Report; European Patent Application No. 09156661.2; Applicant: Ardian, Inc.; dated Jul. 23, 2009, 6 pgs.
European Search Report; European Patent Application No. 09167937.3; Applicant: Ardian, Inc.; dated Nov. 11, 2009, 6 pgs.
European Search Report; European Patent Application No. 09168202.1; Applicant: Ardian, Inc.; dated Nov. 11, 2009, 5 pgs.
European Search Report; European Patent Application No. 09168204.7; Applicant: Ardian, Inc.; dated Nov. 19, 2009, 6 pgs.
Evelyn, K.A. et al., Effect of thoracolumbar sympathectomy on the clinical course of primary (essential) hypertension, Am J Med, 1960;28:188-221.
Ex parte Quayle Office Action; U.S. Appl. No. 11/144,173; dated May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; dated Jan. 29, 2009, 11 pgs.
Final Office Action; U.S. Appl. No. 11/266,993; dated Jan. 8, 2010, 7 pgs.

(56) References Cited

OTHER PUBLICATIONS

Final Office Action; U.S. Appl. No. 11/363,867; dated May 1, 2009, 8 pgs.
Final Office Action; U.S. Appl. No. 11/451,728; dated Jan. 13, 2009, 7 pgs.
Final Office Action; U.S. Appl. No. 11/599,649; dated Jan. 15, 2009, 10 pgs.
Final Office Action; U.S. Appl. No. 11/599,723; dated Apr. 5, 2010, 17 pgs.
Final Office Action; U.S. Appl. No. 11/599,890; dated Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages. Mar. 17, 2008.
Gaylor, D.C. et al., Significance of Cell Size and Tissue Structure in Electrical Trauma, Jan. 26, 1988, J.theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba<http:www.elsevier.com/locate/bba>.
Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update, pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104 (4): 771-786.
Higuchi, Yoshinori, M.D., Ph.D et al., Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.
Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.

(56) References Cited

OTHER PUBLICATIONS

Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, By Gender, B.C., 2001/2002, Graph, Chronic Disease Management, May 2003, British Columbia Ministry of Health Services, 1 page.
Implantable Neurostimulation Systems, Medtronic Neurological, http://medtronic.com/neuro/paintherapies/pain_treatment_ladder/pdf/implantable_brochure.pdf; 1999, 6 pages.
Implantable Pump—The Medtronic MiniMed 2007 Implantable Insulin Pump System, Medtronic MiniMed, 2006, 5 pgs.
International Search Report and Written Opinion for PCT/US2009/069334; Applicant: Ardian, Inc.; dated Mar. 1, 2010, 10 pgs.
International Search Report and Written Opinion, PCT/US05/35693, dated Mar. 8, 2006, Applicant: Ardian, Inc., 29 pgs.
International Search Report and Written Opinion, PCT/US05/35757, dated Dec. 27, 2006, Applicant: Ardian, Inc., 8 pgs.
International Search Report and Written Opinion, PCT/US06/36120, dated Jun. 25, 2008, Applicant: Ardian, Inc., 10 pgs.
International Search Report and Written Opinion, PCT/US06/41889, dated Oct. 20, 2008, Applicant: Ardian, Inc., 7 pgs.
International Search Report and Written Opinion, PCT/US06/48822, dated Aug. 15, 2008, Applicant: Ardian, Inc., 12 pgs.
International Search Report and Written Opinion, PCT/US07/63322, dated Mar. 3, 2008, Applicant: Ardian, Inc., 10 pgs.
International Search Report and Written Opinion, PCT/US07/63324, dated Oct. 10, 2008, Applicant: Ardian, Inc., 10 pgs.
International Search Report and Written Opinion, PCT/US07/66539, dated Jan. 28, 2008, Applicant: Ardian, Inc., 6 pgs.
International Search Report and Written Opinion, PCT/US07/70799, dated Jul. 2, 2008, Applicant: Ardian, Inc., 7 pgs.
International Search Report and Written Opinion, PCT/US07/72396, dated Aug. 27, 2008, Applicant: Ardian, Inc., 9 pgs.
International Search Report and Written Opinion, PCT/US07/84701, dated Aug. 21, 2008, Applicant: Ardian, Inc., 11 pgs.
International Search Report and Written Opinion, PCT/US07/84705, dated Jul. 28, 2008, Applicant: Ardian, Inc., 12 pgs.
International Search Report and Written Opinion, PCT/US07/84708, dated Aug. 11, 2008, Applicant: Ardian, Inc., 9 pgs.
International Search Report, PCT/US02/0039, dated Sep. 11, 2002, Applicant: Advanced Neuromodulation Systems, Inc.
International Search Report, PCT/US02/25712, dated Apr. 23, 2003, Applicant: Cyberonics, Inc.
International Search Report, PCT/US03/08014, dated Sep. 23, 2003, Applicant: The General Hospital Corporation.
International Search Report, PCT/US03/09764, dated Oct. 28, 2003, Applicant: CVRX, Inc.
International Search Report, PCT/US04/38498, dated Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, p. 052901-1-052901-4.
Joshi, R. P. et al., Improved energy model for membrane electroporation in biological cells subjected to electrical pulses, Apr. 9, 2002, Physical Review E, vol. 65, 041920-1,2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II): II-166-II-174.
Katholi, R.E. et al., Role of the renal nerves in the pathogenesis of one-kidney renal hypertension in the rat, Hypertension, 1981,3(4) 404-409.
Katholi, R.E., Renal nerves and hypertension: an update, Fed Proc., 1985, 44:2846-2850.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.

(56) References Cited

OTHER PUBLICATIONS

Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, SLEEP 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.
Lee, Raphael C. et al., Biophysical Injury Mechanisms in Electronic Shock Trauma, Annu. Rev. Biomed. Eng., 2000, vol. 2, Copyright ©2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee, Raphael C. et al., Membrane Biology and Biophysics, Chapter 25, Surgical Research, 2001 Academic Press, pp. 297-305.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.

Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.
Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.
Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.
Mancia, G Grassi, G Giannattasio, C Seravalle, G Sympathetic actrivation of pathogenesis of hypertension and progression of organ damage, Hypertension 1999, 34 (4 Pt?): 724-728.
Marenzi, Giancarlo, M.D et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
McCullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.

(56) References Cited

OTHER PUBLICATIONS

McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
McRobbie, D. and M.A. Foster, Thresholds for biological effects of time-varying magnetic fields, Dec. 16, 1983, Clin. Phys. Physiol. Meas. 1984, vol. 5, No. 2, 1984 the Institute of Physics, pp. 67-78.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis USA Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al., A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCl) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You at Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; dated Mar. 21, 2006, 14 pgs.
Non-Final Office Action; U.S. Appl. No. 11/129,765; dated May 18, 2007, 10 pgs.
Non-Final Office Action; U.S. Appl. No. 11/129,765; dated Sep. 10, 2007, 5 pgs.
Non-Final Office Action; U.S. Appl. No. 11/129,765; dated Oct. 6, 2006, 30 pgs.
Non-Final Office Action; U.S. Appl. No. 11/133,925; dated Oct. 8, 2008, 41 pgs.
Non-Final Office Action; U.S. Appl. No. 11/144,173; dated Apr. 5, 2007, 33 pgs.
Non-Final Office Action; U.S. Appl. No. 11/144,173; dated Sep. 10, 2007, 5 pgs.
Non-Final Office Action; U.S. Appl. No. 11/144,298; dated Oct. 29, 2009, 8 pgs.
Non-Final Office Action; U.S. Appl. No. 11/144,298; dated Apr. 5, 2007, 33 pgs.
Non-Final Office Action; U.S. Appl. No. 11/144,298; dated Sep. 10, 2007, 5 pgs.
Non-Final Office Action; U.S. Appl. No. 11/144,298; dated Dec. 29, 2008, 7 pgs.
Non-Final Office Action; U.S. Appl. No. 11/145,122; dated Apr. 11, 2007, 33 pgs.
Non-Final Office Action; U.S. Appl. No. 11/145,122; dated Sep. 10, 2007, 5 pgs.
Non-Final Office Action; U.S. Appl. No. 11/189,563; dated May 28, 2009, 5 pgs.
Non-Final Office Action; U.S. Appl. No. 11/233,814; dated Jun. 17, 2008, 12 pgs.
Non-Final Office Action; U.S. Appl. No. 11/252,462; dated Feb. 22, 2010, 6 pgs.
Non-Final Office Action; U.S. Appl. No. 11/266,993; dated Jul. 8, 2009, 5 pgs.
Non-Final Office Action; U.S. Appl. No. 11/266,993; dated Dec. 30, 2008, 7 pgs.
Non-Final Office Action; U.S. Appl. No. 11/363,867; dated Sep. 25, 2008, 10 pgs.
Non-Final Office Action; U.S. Appl. No. 11/368,553; dated May 18, 2010, 4 pgs.
Non-Final Office Action; U.S. Appl. No. 11/368,553; dated Oct. 7, 2009, 5 pgs.
Non-Final Office Action; U.S. Appl. No. 11/368,809; dated Dec. 3, 2009, 4 pgs.
Non-Final Office Action; U.S. Appl. No. 11/368,949; dated Jun. 11, 2010, 6 pgs.
Non-Final Office Action; U.S. Appl. No. 11/368,971; dated Aug. 24, 2010, 9 pgs.
Non-Final Office Action; U.S. Appl. No. 11/451,728; dated Jun. 12, 2008, 41 pgs.
Non-Final Office Action; U.S. Appl. No. 11/451,728; dated Jul. 2, 2009, 5 pgs.
Non-Final Office Action; U.S. Appl. No. 11/451,728; dated Dec. 28, 2009, 7 pgs.
Non-Final Office Action; U.S. Appl. No. 11/504,117; dated Mar. 31, 2009, 10 pgs.
Non-Final Office Action; U.S. Appl. No. 11/599,649; dated Mar. 30, 2009, 10 pgs.
Non-Final Office Action; U.S. Appl. No. 11/599,649; dated Jun. 23, 2008, 9 pgs.
Non-Final Office Action; U.S. Appl. No. 11/599,723; dated Jun. 26, 2009, 17 pgs.
Non-Final Office Action; U.S. Appl. No. 11/599,723; dated Oct. 15, 2010, 16 pgs.
Non-Final Office Action; U.S. Appl. No. 11/599,882; dated Jul. 6, 2009, 13 pgs.
Non-Final Office Action; U.S. Appl. No. 11/688,178; dated Jun. 28, 2010, 5 pgs.
Non-Final Office Action; U.S. Appl. No. 11/840,142; dated Apr. 3, 2009, 13 pgs.
Non-Final Office Action; U.S. Appl. No. 12/567,521; dated Sep. 3, 2010, 9 pgs.
Non-Final Office Action; U.S. Appl. No. 12/616,708; dated Sep. 16, 2010, 10 pgs.
Non-Final Office Action; U.S. Appl. No. 12/725,375; dated Oct. 12, 2010, 14 pgs.
Nozawa, T. et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G et al., Blood pressure regulation in end-stage renal disease and anephric man, Circ Res Suppl., 1975, 36 & 37: 145-152.

(56) References Cited

OTHER PUBLICATIONS

Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al., The Histologic Effects of Pulsed and Continuous Radiofrequency Lesions at 42 C to Rat Dorsal Root Ganglion and Sciatic Nerve, SPINE, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal orThoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11 (1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.

(56) References Cited

OTHER PUBLICATIONS

Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al., Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . . An Implantable Bolus Infusion Pump for the Neurosciences, FRP, Apr. 2005, 3 pages.
Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006).
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H., Surgical treatment of hypertension, Am J Med 1948, 4:744-759.
Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.
Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.
Steffen, W. et al., Catheter-delivered high intensity, low frequency ultrasound induces vasodilation in vivo, European Heart Journal. 1994. 15; pp. 369-376.
Steg, PG et al., Pulsed ultraviolet laser irradiation produces endothelium-independent relaxation of vascular smooth muscle, Circulation: Journal of the American Heart Association. 1989. pp. 189-197.
Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.
Strojek, K. et al., Lowering of microalbuminuria in diabetic patients by a sympathicoplegic agent: novel approach to prevent progression of diabetic nephropathy? J Am Soc Nephrol. 2001;12:602-5.
Summary, Critical Reviews in Biomedical Engineering, vol. 17, Issue 5, 1989, pp. 515-529.
Sung, Duk Hyun, M.D. et al., Phenol Block of Peripheral Nerve Conduction: Titrating for Optimum Effect, Jun. 27, 2000, Arch. Phys. Med. Rehabil. Vol. 82, May 2001, pp. 671-676.
Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Terashima, Mitsuyasu et al. Feasibility and Safety of a Novel CryoPlasty™ System. Poster. 1 page, Mar. 15, 2002.
Thatipelli et al., CT Angiography of Renal Artery Anatomy for Evaluating Embolic Protection Devices, Journal of Vascular and Interventional Radiology, Jul. 2007, pp. 842-846.
The Antihypertensive and Lipid-Lowering Treatment to Prevent Heart Attack Trial, ALLHAT Research Group, JAMA, 2002, vol. 288, pp. 2981-2997.

(56) References Cited

OTHER PUBLICATIONS

Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.
Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A et al., Extrinsic Innervation of the Canine Superior Vena Cava, Pulmonary, Portal and Renal Veins, Angiology—Journal of Vascular Diseases, Aug. 1984, pp. 486-493.
Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.
Van Antwerp, Bill and Poonam Gulati, Protein Delivery from Mechanical Devices Challenges and Opportunities, Medtronic presentation, 19 pages, Jul. 2003.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vonend, O. et al., Moxonidine treatment of hypertensive patients with advanced renal failure. J Hypertens. 2003;21:1709-17.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.

Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S et al., A limited renal injury may cause a permanent form of neurogenic hypertension. Am J Hypertens. 1998;11:723-8.
Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.
Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.
Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.
Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.
Zanchetti, A. et al., Neural Control of the Kidney-Are There Reno-Renal Reflexes?, Clin. and Exper. Hyper. Theory and Practice, A6 (1&2), 1984, Marcel Dekker, Inc. 1984, pp. 275-286.
Zanchetti, A. et al., Practice Guidelines for Primary Care Physicians: 2003 ESH/ESC Hypertension Guidelines, Journal of Hypertension, vol. 21, No. 10, 2003, pp. 1779-1786.
Zanchetti, A.S., Neural regulation of renin release: Experimental evidence and clinical implications in arterial hypertension, Circulation, 1977, 56(5) 691-698.
Zimmermann, Ulrich, Electrical Breakdown, Electropermeabilization and Electrofusion, Rev. Physiol. Biochem. Pharmacol., vol. 105, Springer-Verlag 1986, pp. 175-256.
Zoccali, C. et al., Plasma norepinephrine predicts survival and incident cardiovascular events in patients with end-stage renal disease. Circulation. 2002;105:1354-9.
Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

(56) References Cited

OTHER PUBLICATIONS

Zundert, Jan Van, M.D. FIPP and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.
Abruzzo, Provvidenza et al., "Oxidative stress in the denervated muscle," Free Radical Research, vol. 44, No. 5, 2010, 563-576.
Amsellem S. et al., "Cubilin is Essential for Albumin Reabsorption in the Renal Proximal Tubule," J Am Soc Nephril, vol. 21, 2010,1859-1867.
Andres, Vicente, "Control of vascular cell pro;iferation and migration by cyclin-dependent kinase signalling: new perspectives and therapeutic potential," Cardiovascular Research, vol. 63, 2004, 11 pages.
Ankri, R. et al., "In-vivo Tumor detection using diffusion reflection measurements of targeted gold nanorods—a quantitative study," Biophotonics, 2012, 11 pages.
Bengatta, S. et al., "MMP9 and SCF Protect from Apoptosis in Acute Kidney Injury," J Am Soc Nephril, vol. 20, 2009, 787-797.
Bhattacharya, S. et al. "Role of p38 Protein Kinase in the Ligand-independent Ubiquitination and Down-regulation of the IFNAR1 Chain of Type I Interferon Receptor," The Journal of Biological Chemistry, vol. 286 No 25, 2011,22069-22076.
Bisoffi, M. et al., "Detection of viral bioagents using a shear horizontal surface acoustic wave biosensor," Biosensors and Bioelectronics, vol. 23, 2008, 7 pages.
Centi et al., "Strategies for electrochemical detection in immunochemistry," Bioanalysis, vol. 1. No. 7, 2009, 21 pages.
Dange, M. et al., "Each Conserved Active Site Tyr in the Three Subunits of Human Isocitrate Dehydrogenase Has a Different Function," The Journal of Biological Chemistry, vol. 285, No. 27, 2010, 6 pages.
Darisipudi, M. et al., "Dual Blockade of the Homeostatic Chemokine CXCL 12 and the Proinflammatory Chemokine CCL2 Has Addictive Protective Effects on Diabetic Kidney Disease," The American Journal of Pathology, vol. 179, No. 1, 2011, 9 pages.
Dhruvajyoti, Roy et al., ""Seeing and Counting" Individual antigens Captured on a Microarrayed Soit with Force-Based Atomic Force Microscopy," Anal. Chem. vol. 82, 2010 6 pages.
Dikow, Ralf et al., "In Renal Transplants With Delayed Graft Function Chemokines and Chemokine Receptor Expression Predict Long-Term Allograft Function, "Transplantation, vol. 90, 2010, 71-776.
Dinish, U. et al., "Highly sensitive SERS detection of cancer proteins in low sample volume using hollow core photonic crystal fiber," Biosens, Bioelecton, 2012, 6 pages.
Dorr et al., "Soluble fms-Like Tyrosine Kinase-1 and Endothelial Adhesion Molecules (Intercellular Cell Adhesion Molecule-1 and Vascular Cell Adhesion Molecule-1) as Predictive Markers for Blood Pressure Reduction After Renal Sympathetic Denervation." Hypertension, 2014, 63, pp. 984-990.
Ford, M. et al., "Expression of fibroblast growth factors and their receptors in rat glomeruli," Kidney International, vol. 51, 1997, 10 pages.
Fragiadaki, Maria et al., "Interstitial fibrosis is associated with increased COL1A2 transcription in AA-injured renal tubular epithelial cells in vivo," Matrix Biology, vol. 30, 2011, 396-403.
Frostick, S. et al., "Schwann Cells, Neurotrophic Factors, and Peripheral Nerve Regeneration," Microsurgery, vol. 18, 1998, 9 pages.
Gaikwad, A. et al., "Epigenetic changes and alteration of Fbn1 and Col3A1 gene expression under hyperglycaemic and hyperinsulinaemic conditions," Biochem. J., vol. 432, 2010, 10 pages.
Green, H., et al., "Development of ERK Activity Sensor, an in vitro, FRET-based sensor of Extracellulat Regulated Kinase activity," BMC Chemical Biology, vol. 5, No. 1 ,2005, 8 pages.
Grishman, Ellen et al., "Toll-like receptors, the NLRP3 inflammasome, and interleukin-1β in the development and progression of type 1 diabetes," Pediatric Research, vol. 71, No. 6, 2012, 7 pages.
Heberlein, Annemarie et al., BDNF plasma levels decrease during benzodiazepine withdrawal in patients suffering from comorbidity of depressive disorder and benzodiazepine dependence, Psychopharmacology, vol. 209, 2010, 3 pages.
Hervas, M. et al., "Electrochemical immunosensing on board microfluidic chip platforms," Trends in Analytical Chemistry, vol. 31, 2012, 20 pages.
Higgins, J, et al., "Gene Expression in the Normal Adult Human Kidney Assessed by Complementary DNA Microarray," Molecular Biology of the Cell, vol. 15, 2004, 649-656.
Hirst, E., "Bond-rupture immunosensors—A review," Biosensors and Bioelectronics, vol. 23, 2008, 10 pages.
Horke, S. et al., "Paraoxonase-2 Reduces Oxidative Stress in Vascular Cells and Decreases Endoplasmic Reticulum Stress-Induced Caspase Activation," Circulation, vol. 115, 2007, 11 pages.
Ihling, C. et al., "Endothelin-1 and Endothelin Converting Enzyme-1 in Human Atherosclerosis—Novel Targets for Pharmacotherapy in Atherosclerosis," Current Vascular Pharmacology, vol. 2, 2004, 10 pages.
Jacobs, C. et al.," Review: Carbon nanotube based electrochemical sensors for biomolecules," Analytical Chimica Acta, vol. 662, 2010, 23 pages.
Jin, Xinghua et al., "Delineation of apoptotic genes for synergistic apoptosis of lexatumumab and anthracyclines in human renal cell carcinoma cells by polymerase chain reaction array," Anti-Cancer Drugs, vol. 23, No. 4, 2012, 10 pages.
Johnson, B. et al., "Biosensing using dynamic-mode cantilever sensors: A review," Biosensors and Bioelectronics, vol. 32, 2012, 18 pages.
Kasuno, Kenji et al., "Clinical Application of Urinary Redox Regulating Protein," Thioredoxin, Rinsho Byori, vol. 59, 2011, 189-195.
Kerr, Heather et al., "Complement-mediated injury and protection of enforhelium: Lessons from atypical haemolytic uraemic syndrome," Immunobiology, vol. 217, 2012, 195-203.
Kinoshita, Yukiko et al., "Angiotensin II type I receptor blockade suppresses glomerular renin-angiotensin system activation, oxidative stress, and progressive glomerular injury in rat anti-glomerular basement membrane glomerulonephritis," Translational Research, vol. 158, No. 4, 2011, 15 pages.
Klosterhalfen, B. et al., "Influence of Heat Shock Protein 70 and Metallothionein Induction by Zinc-bis-(DL-Hydrogenaspartate) on the Release of Inflammatory Mediators in a Porcine Model of Recurrent Endotoxemia." Biochemical Pharmacology, vol. 52, 1996, 1201-1210.
Kopp, "Endothelin in the Control of Renal Sympathetic Nerve Activity," Contrib Nephrol. Basel, Karger, vol. 172, 2011, 107-119.
Kopp, Ulla C. et al., "Impaired Interaction Between Efferent and Afferent Renal Nerve Activity in SHR Involves Increased Activation of α2-Adrenoceptors," vol. 57, 2011, 640-647.
Kourtzelis, L., et al., "Complement anaphylatoxin C5a contributes to hemodialysis-associated thrombosis," Blood, 116, No. 4, 2010 9 pages.
Krukoff, Teresa L. et al., "Effects of renal denervation and reinnervation on ganglionic gene expression of neurotransmitter proteins and c-fos in rat," Molecular Brain Research, vol. 19, 1993, 6 pages.
Lan, Hui Yao, Transforming growth factor-β/Smad signalling in diabetic nephropathy, Clinical and Experimental Pharmacology and Physiology, vol. 39, 2012, 731-738.
Lantero, A. et al., "Transforming Growth Factor-β in Normal Nociceptive Processing and Pathological Pain Models," Mol Neurobiol, vol. 45, 2012, 76-86.
Lechner, Stefan et al., "Regulation of neuronal ion channels via P2Y receptors," Purinergic Signalling, vol. 1, 2004, 31-41.
Lee, Y. et al., "Fibromodulin Suppresses Nuclear Factor-κB Activity by Inducing the Delayed Degradation of IKBA via a JNK—dependent Pathway Coupled to Fibroblast Apoptosis," The Journal of Biological Chemistry, vol. 286, No. 8, 2011, 9 pages.
Leguillon-Buffello, D. et al., "An Alternative Quantitative Acoustical and Electrical Method for Detection of Cell Adhesion Process in Real-Time," Biotechnology and Bioengineering, vol. 108, No. 4, 2011, 16 pages.

(56) References Cited

OTHER PUBLICATIONS

Leonard, M., et al., "Reoxygenation-specific activation of the antioxidant transcription factor Nrf2 mediates cytoprotective gene expression in ischemia-reperfusion injury," The FASEB Journal, vol. 20, 2006, 3 pages.
Liang, W. et al., "A novel microfluidic immunoassay system based on electrochemical immunosensors: An application for the detection of NT-proBNP in whole blood," Biosensors and Bioelectronics, vol. 31, 2012, 6 pages.
Liu, Bin et al., "Role of cyclooxygenase-1-mediated prostacyclin synthesis in endothelium-dependent vasoconstrictor activity of porcine interlobular renal arteries," Am J Physiol Renal Physiol, vol. 302, 2012, F1133-F1140.
Liu, Y. et al., "BID Binds to Replication Protein A and Stimulates ATR Function following Replicative Stress," Molecular and Cellular Biology, vol. 31, No. 21, 2011, 12 pages.
Liu, Yanxin et al., "A novel SNP of the ATP1A1 gene is associated with heat tolerance traits in dairy cows," vol. 38, 2011, 83-88.
Liu, Ying et al., "Induction of KLF4 in response to heat stress," Cell Stress & Champerones, vol. 11, No. 4, 2006, 379-389.
Liu, Yong et al., "Renal Medullary MicroRNAs in Dahl Salt-Sensitive Rats: miR-29b Regulates Several Collagens and Related Genes," Hypertension, vol. 55, 2010, 974-982.
Lloyd-Burton, S. et al., "SPARC-Like 1 (SC1) is a Diversely Expressed and Developmentally Regulated Matricellular Protein That Does Not Compensate for the Absence of SPARC in the CNS," The Journal of Comparative Neurology: Research in Systems Neuroscience, vol. 520, 2012, 2575-2590.
Lo, Denise et al., "Chemokines and their Receptors in Human Renal Allotransplantation," Transplantation, Author manuscript; available in PMC, 2012, 14 pages.
Longley, C. D. et al., "Proportions of Renal and Splenic Postganglionic Sympathetic Populations Containing Galanin and Dopamine Beta Hydroxylase," Neuroscience, vol. 55, No. 1, 1993, 9 pages.
Lu, X. et al., "The Role of Heat Shock Protein (HSP) in Atherosclerosis: Pathophysiology and Clinical Opportunities," Current Medicinal Chemistry, vol. 17, 2010, 957-973.
Luo, Lin, "Gene expression profiles of laser-captured adjacent neuronal subtypes," Nature Medicine, vol. 5, No. 1, 1999, 6 pages.
Ma, Frank, et al., "TGF-β1-activated kinase-1 regulated inflammation and fibrosis in the obstructed kidney," Am J. Physiol Renal Physiol, vol. 300, 2011, 12 pages.
Maeshima, A. et al., "Activin A: Autocrine Regulator of Kidney Development and Repair," Endocrine Journal, vol. 55, No. 1, 2008 9 pages.
Maity, Tapan et al., "Distinct, Gene Specific Effect of Heat Shock on Heat Shock Factor-1 Recruitment and Gene Expression of CXC Chemokine Genes," Cytokine, Author manuscript, available in PMC, 2012, 14 pages.
Mas, Valeria et al., "Gene Expression Patterns in Deceased Donor Kidneys Developing Delayed Graft Function After Kidney Transplantation," Transplantation, vol. 85, No. 4, 2008, 10 pages.
Mazanowska, O et al. "Imbalance of Metallaproteinase/Tissue Inhibitors of Metalloproteinase System in Renal Transplant Recipients With Chronic Allograft Injury." Transplantation Proceedings, vol. 43, 2011, 4 pages.
Messina, G., et al., "Microfluidic immunosensor design for the quantification of interleukin-6 in human serum samples," Analytical Biochemistry, vol. 380, 2008, 6 pages.
Metters, J. et al., "New directions in screen printed elctroanalytical sensors: an overview of recent developments," Analyst, vol. 136, 2011, 10 pages.
Musial K., et al., "Heat shock proteins in chronic kidney disease," Journal of the International Pediatric Nephrology Association, 2010, 9 pages.
Nakaya, R. et al., "Identification of proteins that may directly interact with human RPA," J. Biochem, vol. 148, No. 5, 2010, 9 pages.
Nath, N. et al., "Evanescent wave fibre optic sensor for detection of L. donovani specific antibodies in sera of kala azar patients," Biosensors & Bioelectronics, 1996, 8 pages.
Obeidat, Motaz A., et al., "Post-transplant nuclear renal scans correlate with renal injury biomarkers and early allograft outcomes," Nephrol Dial Transplant, vol. 26, 2011, 8 pages.
Orellana G. et al., "New Trends in Fiber-Optic Chemical and Biological Sensors," Current Analytical Chemistry, vol. 4, 2008, 23 pages.
Pache, G. et al., "Upregulation of Id-1 via BMP-2 receptors induces reactive oxygen species in podocytes," Am J Physiol Renal Physiol, vol. 291, 2006, 9 pages.
Panini, N. et al., "Integrated microfluidoc systems with an immunosensor modified with carbon nanotubes for detection of prostate specific antigen (PSA) in human serum samples," Biosensors and Bioelectronics, vol. 23, 2008, 7 pages.
Paulis, L. et al., "Novel therapeutic targets for hypertension," Nature Reviews: Cardiology, vol. 7, 2010, 11 pages.
Pereira, Rui et al., "Neutrophil and monocyte activation in chronic kidney disease patients under hemodialysis and its relationship with resistance to recombinant human erythropoietin and to the hemodialysis procedure," Hemodialysis International, vol. 14, 2010, 7 pages.
Ransom, Richard F. et al., "Differential proteomic analysis of proteins induced by gluecocorticoids in cultured murine podocytes," Kidney International, vol. 67, 2005, 1275-1285.
Reich, Heather N. et al., "Molecular Markers of Injury in Kidney Biopsy Specimens of Patients with Lupus Nephritis," The Journal of Molecular Diagnostics, vol. 13, No. 2, 2011, 9 pages.
Romanenko, Alina et al., "p16$^{INK4A}$ and p15$^{INK4B}$ Gene Alteration Associated with Oxidative Stress in Renal Cell Carcinomas After the Chernobyl Accident (Pilot Study)," Diagnostic Molecular Pathology, vol. 11, No. 3, 2002, 163-169.
Ruotsalainen, V. et al., "Nephrin is specifically located at the slit diaphragm of glomerular podocytes," Proc. Natl. Acad. Sci. USA, vol. 96, 1999, 6 pages.
Rusling, J. et al., "Measurement of biomarker proteins for point-of-care early detection and monitoring of cancer," Analyst, Author manuscript, available in PMC, 2010, 31 pages.
Rusnati, M. et al., "Exploiting Surface Plasmon Resonance (SPR) Technology for the Identification of Fibroblast Growth Factor-2 (FGF2) Antagonists Endowed with Antiangiogenic Activity," Sensors, vol. 9, 2009, 33 pages.
Sadik, O. et al., "Status of biomolecular recognition using electrochemical techniques," Biosensors and Bioelectronics, vol. 24, 2009, 17 pages.
Saito, S. et al., "Analysis of glial cell line-derived neurotrophic factor-inducible zinc finger protein 1 expression in human diseased kidney," Human Pathology, col. 42, 2011, 11 pages.
Sataranatarajan, K. et al., "Regulation of Elongation Phase of mRNA Translation in Diabetic Nephropathy," The American Journal of Pathology, vol. 171, No. 6, 2007, 10 pages.
Sigdel, Tara K. et al., "Shotgun Proteomics Identifies Proteins Specific for Acute Renal Transplant Rejection," Proteomics Clin Appl. Author manuscript; available in PMC 2010, 27 pages.
Snigdha, Shikha et al., "Caspase-3 activation as a bifurcation point between plasticity and cell death," Neurosci Bull, vol. 28, No. 1, 2012, 11 pages.
Soleimani, M., "Dietary fructose, salt absorption and hypertension in metabolic syndrome: towards a new paradigm," Acta Physiol, vol. 201, 2011, 55-62.
Sonna, L. et al., "Molecular Biology of Thermoregulation Invited Review: Effects of heat and cold stress on mammalian gene expression," J Appl Physiol, vol. 92, No. 1725, 2002, 17-42.
Struckmann, Kirsten et al., "Impaired Expression of the Cell Cycle Regulator BTG2 is Common in Clear Cell Renal Cell Carcinoma," Cancer Res, vol. 64, 2004, 1632-1638.
Su, Y. et al., "Chromatic immunoassay based on polydiacetylene vesicles," Colloids and Surfaces B: Biointerfaces, vol. 38, 2004, 5 pages.
Sun, A. et al., "Sensitive label-free electrochemical immunoassay based on a redox matrix of gold nanoparticles/Azure 1/multi-wall carbon nanotubes composite," Biochemical Engineering Journal, vol. 57, 2011, 6 pages.

(56) References Cited

OTHER PUBLICATIONS

Sun, Dong et al., "Thrombospondin-1 Short Hairpin RNA Suppresses Tubulointerstitial Fibrosis in the Kidney of Ureteral Obstruction by Ameliorating Peritubular Capillary Injury," Kidney Blood Press Res, vol. 35, 2012, 6 pages.
Tiniakos, D. et al, "Ontogeny of intrinsic innervation in the human kidney," Anat Embryol, vol. 209, 2004, 7 pages.
Todorov, Vladimir et al., "Differential Regulation of Cathepsin B and Prorenin Gene Expression in Renal Juxtaglomerular Cells," Kidney Blood Press Res, vol. 24, 2001, 4 pages.
Trimarchi, Hernan et al., "Proteinuria: an ignored marker of inflammation and cardiovascular disease in chronic hemodialysis," International Journal of Nephrology and Renovascular Disease, vol. 5, 2012, 7 pages.
Vivekanandan, A. et al., "Urine Glycoprotein Profile Reveals Novel Markers for Chronic Kidney Disease," International Journal of Proteomics, 2011, 18 pages.
Waalkes et al., "Fibronectin 1 mRNA expression correlates with advanced disease in renal cancer," Cancer, vol. 10, 2010, 6 pages.
Wang, Bao-Ying et al., Hepatotoxicity and gene expression downregulation of CYP isozymes caused by Yenal ischemia/reperfusion in the rat, Experimental and Toxicologic Pathology 61 (2009) 169-176.
Wong, Dona L. et al., "Adrenergic Responses To Stress: Transcriptional and Post-Transcriptional Changes," Ann N Y Acad Sci. Author manuscript; available in PMC, 2009, 10 pages.
Wu, Huiling et al., "TLR4 activation mediates kidney ischemia/reperfusion injury," The Journal of Clinical Investigation, vol. 117, No. 10, 2007, 2847-2859.
Xie, Chaoqin, "Ablation of Transient Receptor Potential Vanilloid 1 Abolishes Endothelin-lnduced Increases in Afferent Renal Nerve Activity: Mechanisms and Functional Significance," Hypertension, vol. 54, 2009, 1298-1305.
Xie, Chaoqin, Interdependent Regulation of Afferent Renal Nerve Activity and Renal Function: Role of Transient Receptor Potential Vanilloid Type 1, Neurokinin 1, and Calcitonin Gene-Related Peptide Receptors, The Journal of Pharmacology and Experimental Therapeutics, vol. 325, No. 3, 7 pages.
Yoshino, Jun et al., "Leukemia Inhibitory Factor is Involved in Tubular Regeneration after Experimental Acute Renal Failure," J Am Soc Nephrol, vol. 14, 2003, 3090-3101.
Yuan, B. et al., "Gene expression reveals vulnerability to oxidative stress and interstitial fibrosis of renal outer medulla to nonhypertensive elevations of ANG II," Am J. Physiol Regul Integr Comp Physiol, vol. 284, 2003, 12 pages.
Zager, Richard et al., "Acute unilateral ischemic renal injury induces progressive renal inflammation, lipid accumulation, histone modification, and "end-stage" kidney disease," Am J Physiol Renal Physiol, vol. 301, 2011, 12 pages.
Zeisberg, Michael, "Bone morphogenic protein-7 and the kidney: current concepts and open questions," Nephrol Dial Transplant, vol. 21, 2006, 6 pages.
Zerega, Barbara et al., "Expression of NRL/NGAL (neu-related lipocalin/neutrophil gelatinase-associated lipocalin) during mammalian embryonic development and in Inflammation." European Journal of Cell Biology, vol. 79, 2000 8 pages.
Zhang, Weiru et al. "Interleukin 6 Underlies Angiotensin II—Induced Hypertension and Chronic Renal Damage," Hypertension, vol. 59, 2012, 136-144.
Zhao, Hongcheng et al., "Activation of the Transcription Factor Oct-1 in Response to DNA Damage," Cancer Res, vol. 60, 2000, 6 pages.
Staal, S.S., et al., "A Prefilled, Ready-to-Use, Electrophoresis-Based Lab-on-a-Chip Device for Monitoring Ions in Blood and Urine." 14th International Conference on Miniaturized Systems for Chemistry and Life Sciences, Oct. 3-7, 2010, Groningen, The Netherlands. 3 pages.
Rusling, James F., "Nanomaterials-Based Electrochemical Immunosensors for Proteins." The Chemical Record, 12 (1), Feb. 2012. 13 pages.
Yanase, Yuhki, et al., "Development of an Optical Fiber SPR Sensor for Living Cell Activation." Biosensors and Bioelectronics, 25 (5), Jan. 15, 2010. 16 pages.
Chinushi et al., "Blood Pressure and Autonomic Responses to Electrical Stimulation of the Renal Arterial Nerves Before and After Ablation of the Renal Artery." Hypertension, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
Extended European Search Report for Application No. 17208077.2, dated Jun. 4, 2018, 11 pages.
Examination Report from Canada Application No. 2,865,242, dated Aug. 13, 2021, 3 pages.
International Preliminary Report on Patentability from PCT App. No. PCT/US2013/030041, dated Sep. 9, 2014, 12 pages.
Wisniewski, Jack R., "Mass Spectrometry-Based Proteomics, Principles, Perspectives, and Challenges", Arch Pathol Lab Med—vol. 132, Oct. 2008, 4 pages.
"Relative Quantitation Using Comparative CT Getting Started Guide", Applied Biosystems 7300/7500/7500 Fast Real-Time PCR System, 2006 (Applicant points out, in accordance with MPEP 609.04(a), that the year of publication, 2006, is sufficiently earlier than the effective U.S. filing date, so that the particular month of publication is not in issue), 120 pages.

\* cited by examiner

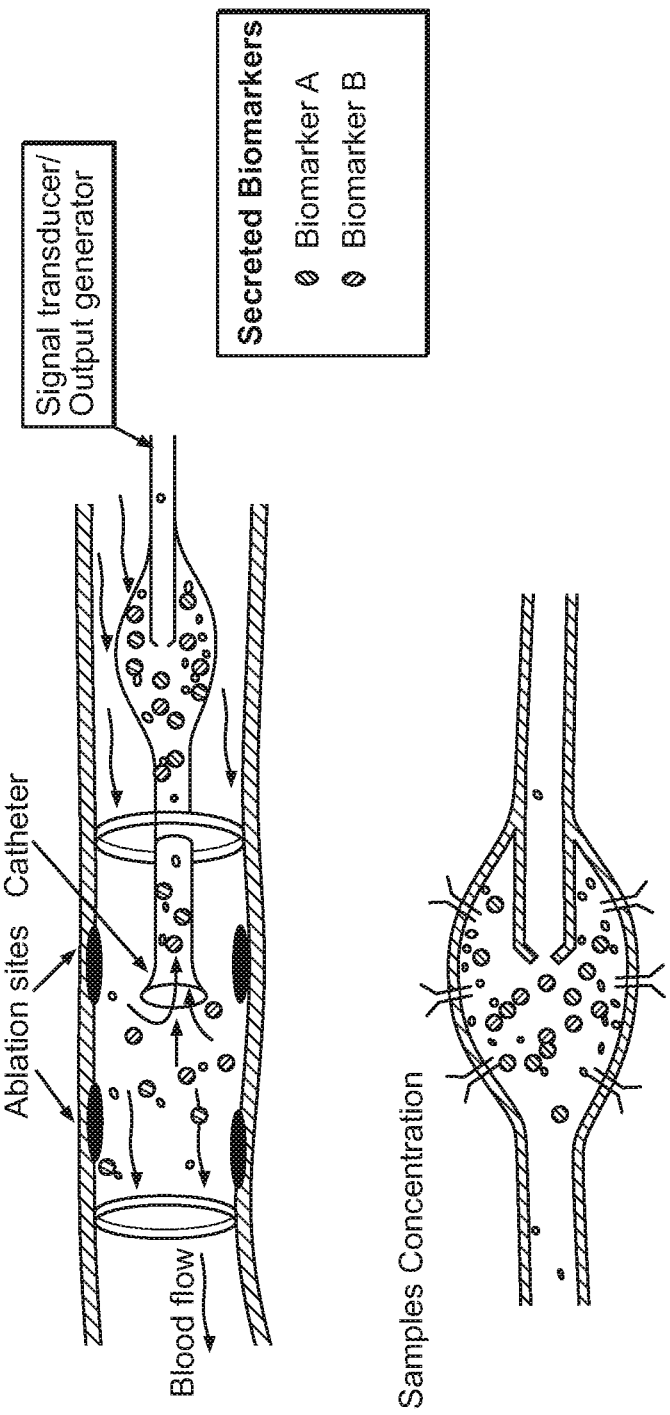
FIG. 9A Sample Collection pre/ post Ablation
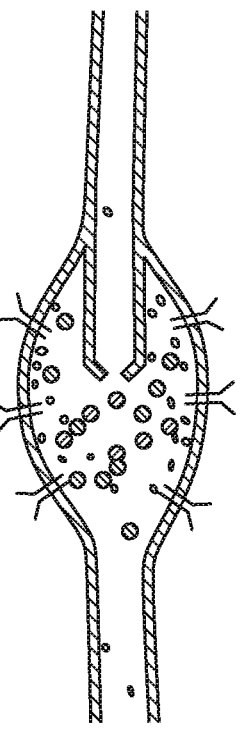
FIG. 9B Samples Concentration
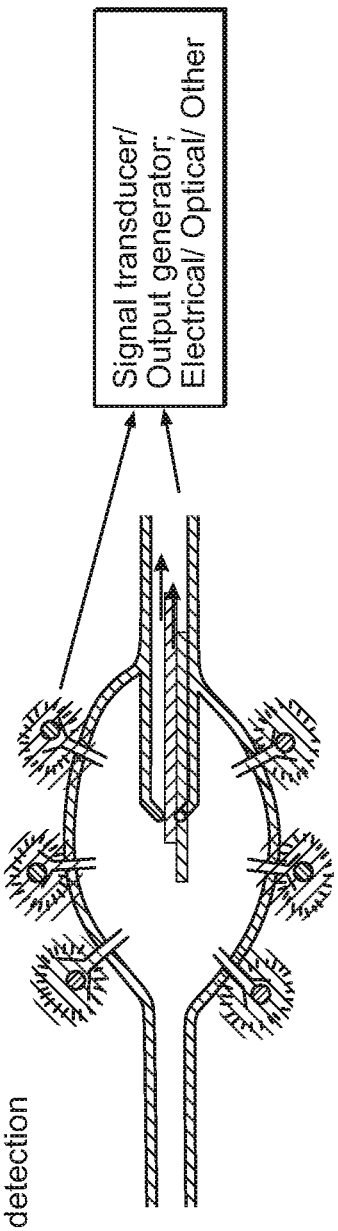
FIG. 9C Signal detection

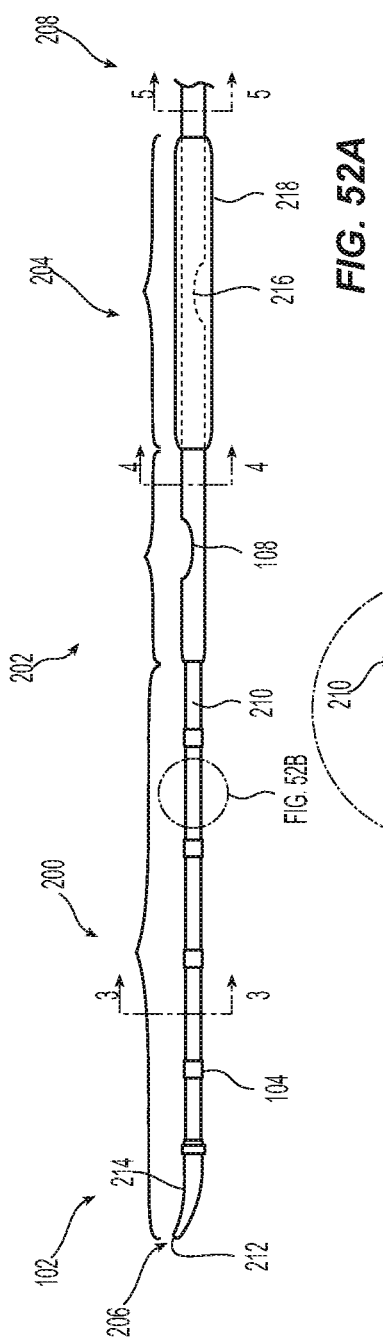
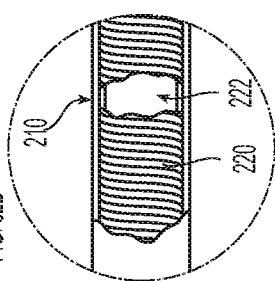
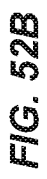
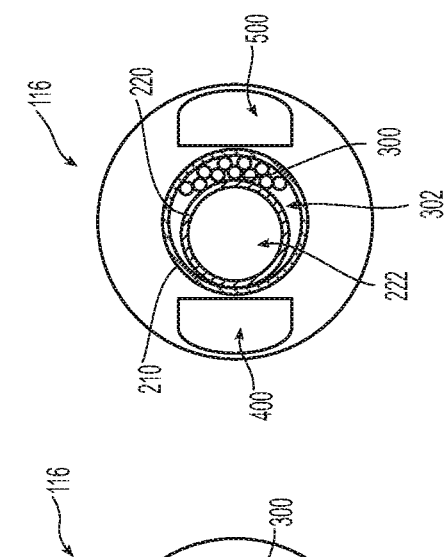
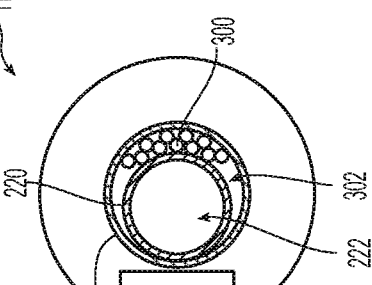
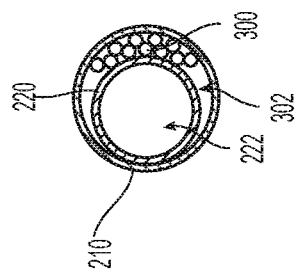

MONITORING OF NEUROMODULATION USING BIOMARKERS

CROSS-REFERENCE TO RELATED APPLICATIONS

This application is a Continuation of and claims the benefit of U.S. patent application Ser. No. 15/296,925, filed Oct. 18, 2016, now U.S. Pat. No. 10,368,791, which is a Continuation of and claims the benefit of U.S. patent application Ser. No. 13/791,681, filed Mar. 8, 2013, now U.S. Pat. No. 9,510,777, which claims priority to U.S. Provisional Patent Application No. 61/608,625, filed Mar. 8, 2012, U.S. Provisional Patent No. 61/608,626, filed Mar. 8, 2012, and U.S. Provisional Patent Application No. 61/746,528, filed Dec. 27, 2012.

All of the foregoing applications are incorporated herein by reference in their entireties. Further, components and features of embodiments disclosed in the applications incorporated by reference may be combined with various components and features disclosed and claimed in the present application.

ADDITIONAL APPLICATION(S) INCORPORATED BY REFERENCE

The following application is also incorporated herein by reference in its entirety:

U.S. patent application Ser. No. 13/791,751, entitled "BIOMARKER SAMPLING IN THE CONTEXT OF NEUROMODULATION DEVICES, SYSTEMS, AND METHODS," filed Mar. 8, 2013, now U.S. Pat. No. 9,597,018.

As such, components and features of embodiments disclosed in this application may be combined with various components and features disclosed in the present application.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF DRAWINGS

FIGS. 9A-C: Representative embodiment of protein target biomarker detection method and device.

FIG. 52A-B: Enlarged side view illustrating a neuromodulation and sampling assembly of the treatment device of FIG. 51 configured in accordance with an embodiment of the present technology. B. Further enlarged cut-away view of a portion of the neuromodulation and sampling assembly of (A) in accordance with an embodiment of the present technology.

FIG. 53: Cross-sectional end view taken along lines 2-2 in FIG. 52A.

FIG. 54: Cross-sectional end view taken along lines 3-3 in FIG. 52A.

FIG. 55: Cross-sectional end view taken along lines 4-4 in FIG. 52A.

DETAILED DESCRIPTION

Figure 1:
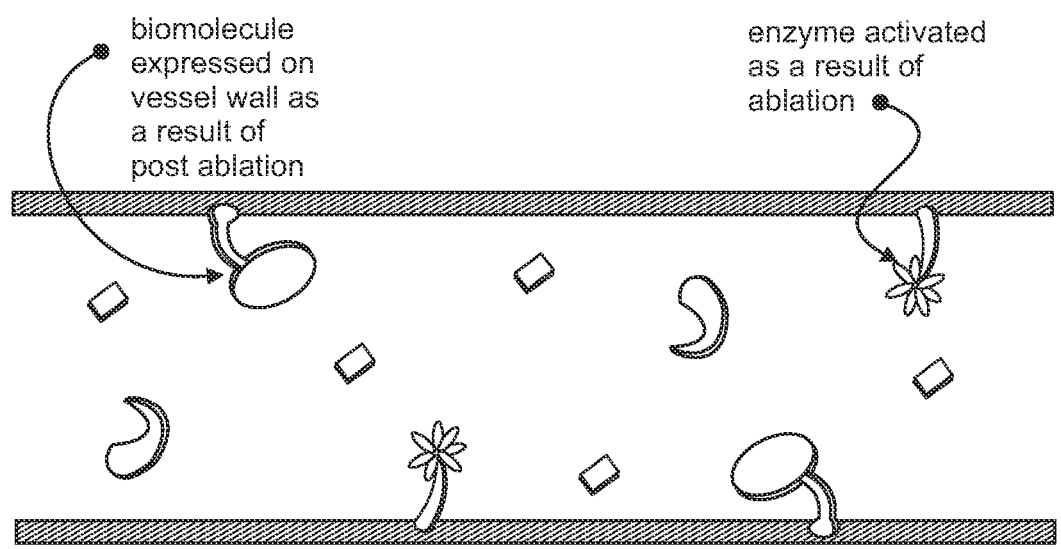
FIG. 1: Illustration of potential target biomarkers for rapid monitoring of renal neuromodulation: artery wall proteins, secreted proteins, enzymes activated as a result of denervation, and secreted small molecules.

The present technology is directed to methods, systems, devices, compositions, and kits for monitoring neuromodulation efficacy by detecting changes in the level or activity of one or more target biomarkers, as well as methods, systems, compositions, and kits for determining biomarker activity in a patient. Specific details of several embodiments of the technology are described below with reference to FIGS. 1-56D. Although many of the embodiments are described below with respect to methods, systems, devices, compositions, and kits for monitoring renal neuromodulation efficacy, other applications (e.g., monitoring nerve activity in the absence of neuromodulation) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-56D.

Several current methods for neuromodulation would benefit from a process for rapid evaluation of success of the procedure. Examples of neuromodulation methods that may benefit from rapid evaluation methods include renal denervation, for example to treat clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, osteoporosis, and sudden death.

Efficacy of many current renal neuromodulation methods is evaluated after the procedure has been completed by monitoring blood pressure, but statistically meaningful changes in blood pressure may not be observed until about 2 weeks, 4 weeks, 3 months, 6 months, or more after completion. In the absence of real-time or at least relatively contemporaneous feedback (e.g., less than about 30 minutes), physicians may miss nerves (i.e., under ablate) with unconventional nerve anatomy or, alternatively, err on the side of over-ablation.

Disclosed herein are several embodiments of methods and processes for monitoring neuromodulation efficacy by detecting changes in the level or activity of one or more target biomarkers associated with neuromodulation, as well as methods and processes of performing neuromodulation that incorporate monitoring of neuromodulation efficacy based on changes in level or activity of one or more target biomarkers. In contrast with many conventional approaches, the disclosed methods are expected to allow for real-time or relatively contemporaneous monitoring of neuromodulation efficacy. In certain embodiments, these methods and processes are used to monitor the efficacy of renal neuromodulation. Also provided herein are methods of treating hypertension in a subject in need thereof using renal neuromodulation, wherein the methods include steps for monitoring the efficacy of the neuromodulation procedure by detecting changes in the level or activity of one or more target biomarkers associated with neuromodulation. Further provided herein are devices, compositions, and kits for use in conjunction with the disclosed methods.

"Neuromodulation" is the partial or complete incapacitation or effective disruption of one or more nerves. Such incapacitation or disruption can be long term (e.g., permanent or for periods of months or years) or short term (e.g., for periods of minutes, hours, days, or weeks). "Renal neuromodulation" is the partial or complete incapacitation or effective disruption of the nerves of the kidneys, including nerves terminating in the kidneys or in structures closely associated with the kidneys. Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity.

Several embodiments of methods for monitoring neuromodulation efficacy by detecting changes in the level or activity of one or more target biomarkers in accordance with the present technology are described herein. In certain embodiments, these methods can be used to determine whether a neuromodulation procedure was successful, i.e., whether the procedure resulted in partial or complete incapacitation or effective disruption of one or more target nerves. In certain embodiments, these methods include (a) determining a baseline level or activity of one or more target biomarkers; (b) performing the neuromodulation procedure; (c) determining a post-neuromodulation level or activity for the target biomarker(s); and (d) comparing the post-neuromodulation level or activity to the baseline level or activity, wherein the neuromodulation procedure is classified as successful if the post-neuromodulation level or activity differs significantly from the baseline level or activity. In certain embodiments, a significant difference in level or activity means a difference of 1% or greater, for example 2% or greater, 3% or greater, 4% or greater, 5% or greater, 10% or greater, 20% or greater, or 50% or greater. In other embodiments, a significant difference in level or activity means a difference of 2-fold or greater, for example 3-fold or greater, 4-fold or greater, or 5-fold or greater. In other embodiments, these methods include (a) performing the neuromodulation procedure; (b) determining a post-neuromodulation level or activity for one or more target biomarkers; and (c) comparing the post-neuromodulation level or activity to a pre-determined threshold level or activity, wherein the neuromodulation procedure is classified as successful if the post-neuromodulation level or activity is greater than the pre-determined threshold level or activity. In still other embodiments, these methods include (a) performing the neuromodulation procedure; (b) determining a post-neuromodulation level or activity for one or more target biomarkers; and (c) comparing the post-neuromodulation level or activity to a pre-determined range of level or activity, wherein the neuromodulation procedure is classified as successful if the post-neuromodulation level or activity falls within the pre-determined range of level or activity. In certain embodiments, post-neuromodulation target biomarker level or activity is determined in an acute timeframe, e.g., within 30 minutes or less following denervation, thereby allowing neuromodulation efficacy to be assessed while a subject is still catheterized. In other embodiments, however, post-neuromodulation target biomarker level or activity may be measured in a chronic timeframe, e.g., within several hours, days, weeks, or months following denervation. In certain embodiments, the methods provided herein include (a) determining a baseline level or activity of one or more target biomarkers, (b) at least partially inhibiting sympathetic neural activity in a renal nerve of the subject via a neuromodulation assembly (discussed in more detail below), (c) determining a post-neuromodulation level or activity for the target biomarker(s), and (d) comparing the post-neuromodulation level or activity to the baseline level or activity, wherein the neuromodulation procedure is classified as successful if the post-neuromodulation level or activity differs significantly from the baseline level or activity.

Also described herein are several embodiments of methods for determining biomarker activity in a patient in accordance with the present technology. In certain of these embodiments, these methods include (a) transluminally positioning an energy delivery element of a catheter within a target blood vessel of a patient and adjacent to target neural fibers, (b) at least partially ablating the target neural fibers via the energy delivery element, (c) capturing a plurality of at least one type of biomarker in a capture compartment of the catheter, wherein the biomarker is secreted as a result of the ablation procedure, (d) sequestering the plurality of the at least one type of biomarker in the capture compartment to concentrate the biomarker, (e) binding the biomarker to at least one immobilized capture agent disposed on an inner surface of the capture compartment, and (f) detecting a concentration of the biomarker, wherein the concentration corresponds, at least in part, to a degree of ablation of the target neural fibers.

Target biomarker(s) for use in conjunction with the methods disclosed herein may be any biomolecule that exhibits a quantitative and detectable change in level or activity following neuromodulation in a desired manner. In certain embodiments, target biomarkers may be proteins or fragments thereof. In these embodiments, a change in protein level may refer to a change in expression (as measured by mRNA or protein level) or secretion. In other embodiments, target biomarkers may be small molecules, peptides, or other non-protein compounds. Provided in certain embodiments are compositions and kits comprising one or more target biomarkers for use in the methods disclosed herein.

In those embodiments that utilize protein target biomarkers, the target biomarkers may be one or more proteins implicated in a cell death, apoptosis, metabolic modulation, oxidative stress, or neuro-endothelial cross-talk pathway, or proteins involved in neuromodulation, hormone modulation, neuronal stress response, neuronal regeneration, endothelial vasodilation or vasoconstriction, modulation of efferent and afferent sympathetic activation, or regulation of catecholamine production. Specific classes of proteins that may be utilized as target biomarkers in conjunction with the methods disclosed herein include but are not limited to endothelins, neurotrophins, vasoconstrictive proteins, cell surface receptors, heatshock proteins or modified heatshock proteins, secreted inflammatory cytokines or chemokines, and proteins from the renin-angiotensin system. Protein target biomarkers for use in the present methods may be cell surface proteins, secreted proteins, or intracellular proteins. In certain of these embodiments, the protein can be a cell surface receptor expressed on a vessel wall, a secreted protein that exhibits increased or decreased secretion levels post-ablation, and/or an enzyme that exhibits increased or decreased activity post-ablation (see, e.g., FIG. 1).

In those embodiments that utilize non-protein target biomarkers, the target biomarkers may be small molecules such as catecholamines or other neurotransmitters (particularly those associated with sympathetic nervous activity) such as NE, neuropeptide Y (NPY) epinephrine, or dopamine, secreted hormonal or other soluble endocrine molecules, or secreted metabolites or cellular debris.

In certain embodiments of the methods disclosed herein, a change in target biomarker level or activity occurs at or near a neuromodulation site (e.g., at or near an ablation site). In these embodiments, the change can be measured at or near the neuromodulation site or in a biological sample obtained from at or near the neuromodulation site. For example, where neuromodulation is carried out at or near the kidney (e.g., in the renal artery), changes in target biomarker level or activity may be measured in a biological sample obtained from at or near the kidney. A "biological sample" as used herein may refer to any bodily fluid (e.g., blood, plasma, urine, etc.) or tissue that may contain one or more target biomarkers. Therefore, a biological sample obtained from at or near the kidney may be blood or tissue from the renal arteries, renal veins, or elsewhere in the renal system. A target biomarker associated with renal neuromodulation may exhibit changes in expression or activity at any or all of these locations. Alternatively or in addition to locally measurable changes in level or activity, in certain embodiments the target biomarkers may exhibit changes in level or activity at locations remote to the neuromodulation site. In these embodiments, target biomarker collection may take place systemically, for example by collecting a blood or urine sample. In certain embodiments, local target biomarker collection may be preferred to systemic collection because it provides a higher concentration of target biomarker and may allow for more rapid or accurate results than systemic collection. In other embodiments, there may be no preference between local and systemic collection, or systemic collection may be preferred, for example due to ease of collection.

Figure 2:
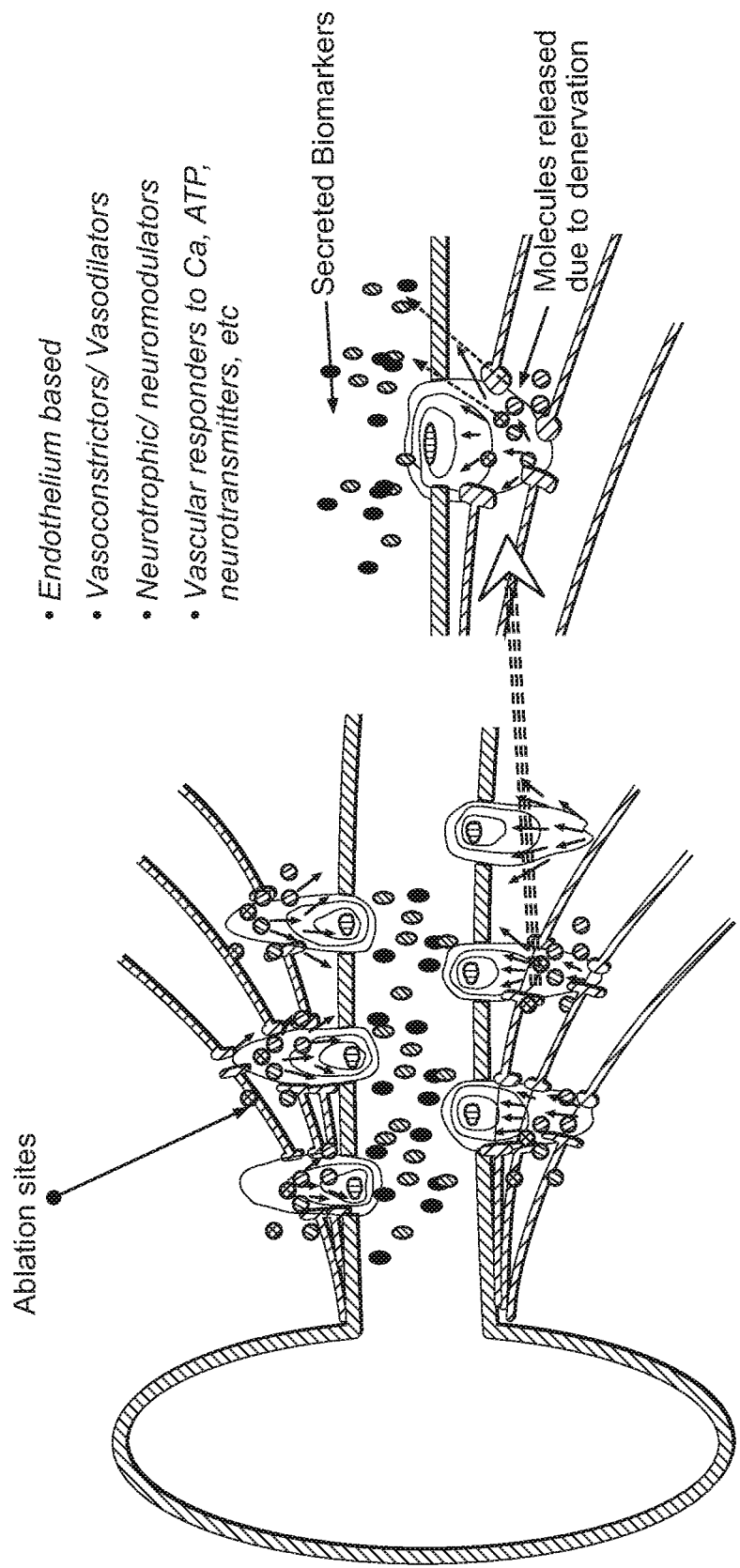
FIG. 2: Illustration of target biomarkers exhibiting changes in level or activity as a result of vascular-neuronal cross-talk.
Figure 3:
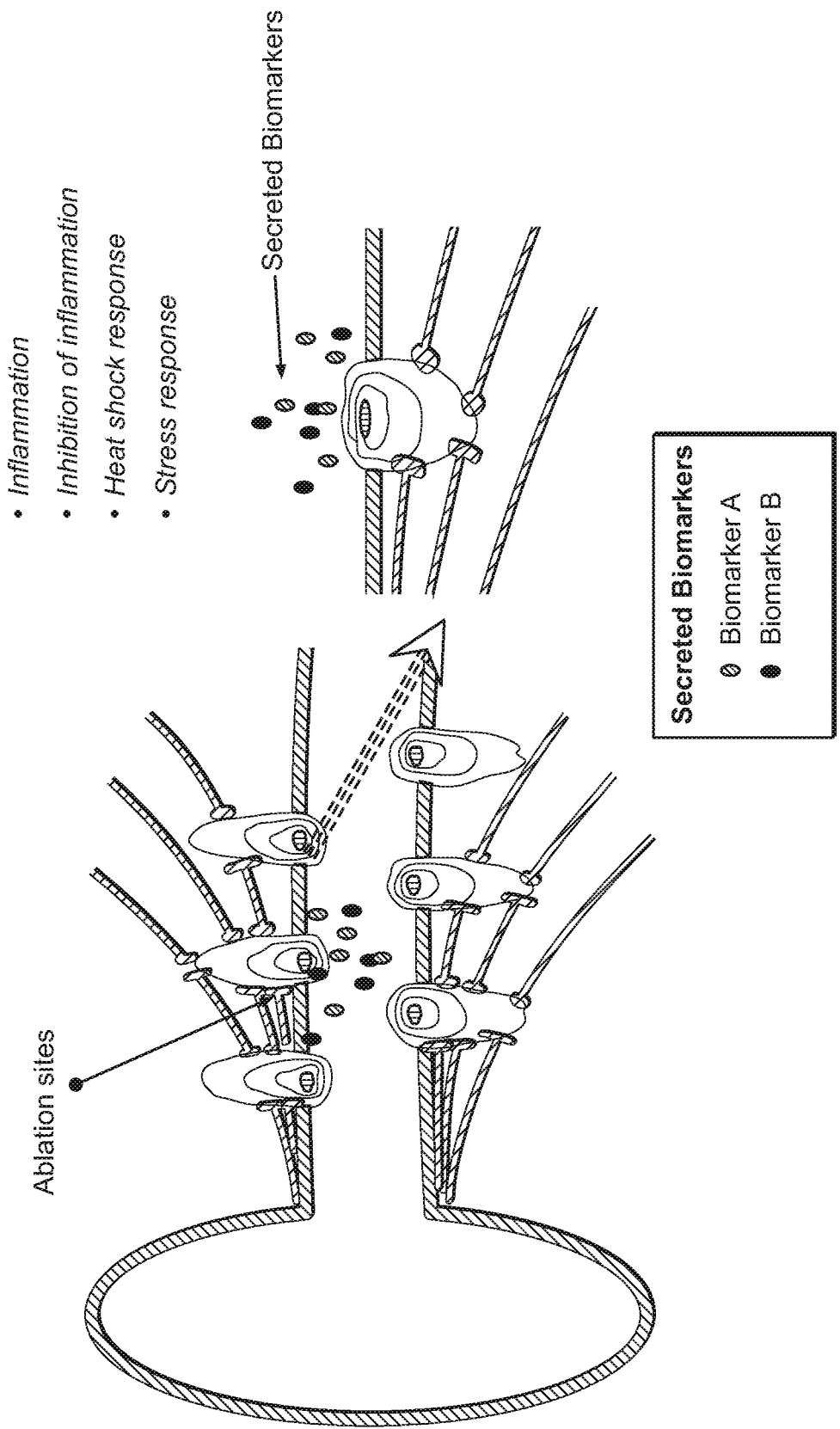
FIG. 3: Illustration of target biomarkers exhibiting changes in level or activity as a surrogate response to neuromodulation (e.g., as a response to RF).

Target biomarkers for use in the methods disclosed herein may exhibit a change in level or activity that correlates with nerve ablation and/or NE levels, for example nerve ablation and/or NE levels in the kidney. In certain embodiments, changes in the level or activity of a target biomarker may be a direct result of neuromodulation, e.g., a direct response to neuronal damage. In certain of these embodiments, the target biomarker may exhibit changes in activity or level as a result of vascular-neuronal cross-talk (see, e.g., FIG. 2). For example, the target biomarker may be an endothelium-based target biomarker, vasoconstrictor, vasodilator, neuromodulator, neurotrophic factor, catecholamine, or vascular responder to signaling molecules such as ATP, neurotransmitters, or calcium that exhibits increased or decreased levels as a direct result of neuromodulation. Changes in the level or activity of a target biomarker may be indicative of a synaptic discharge of substances such as small molecules (e.g., calcium) or neurotransmitters as a result of axonal damage, axonal stress, or axotectomy. For example, sympathetic denervation might result in discharge of NE, NPY, or dopamine reserves at the synaptic ends in the kidney, resulting in a burst that can be collected and detected from renal arterial or venous blood or elsewhere such as in systemic blood or urine. In other embodiments, changes in the level or activity of a target biomarker may be an indirect/surrogate response to the neuromodulation procedure (see, e.g., FIG. 3). For example, a target biomarker may be a protein such as an inflammatory or anti-inflammatory pathway, heat shock response pathway, or stress response pathway protein that exhibits a change in level or activity in response to RF exposure or changes in temperature at or near an ablation site.

In certain embodiments of the methods disclosed herein, neuromodulation efficacy is monitored by detecting changes in the level or activity of a single target biomarker. In other embodiments, efficacy is monitored by detecting changes in the level or activity of two or more target biomarkers. In certain of these embodiments, neuromodulation is classified as successful if each of the target biomarkers exhibits a change in level or activity. In other embodiments, neuromodulation is classified as successful if a threshold number or a specific subset or combination of target biomarkers exhibits a change in level or activity. In those embodiments that utilize two or more target biomarkers, the target biomarkers may be all proteins, all non-proteins, or a combination of proteins and non-proteins.

In certain embodiments of the methods disclosed herein, baseline level or activity of a target biomarker is derived from the subject undergoing neuromodulation. For example, target biomarker level or activity may be measured in the subject at one or more timepoints before neuromodulation. The baseline value may represent target biomarker level or activity at a specific timepoint before neuromodulation, or it may represent an average level or activity at two or more timepoints before neuromodulation. In certain preferred embodiments, a baseline value is based on target biomarker level or activity immediately before neuromodulation (i.e., after the subject has already been catheterized). Alternatively, a baseline value for a particular target biomarker may be derived from a standard value for that target biomarker across the population as a whole or across a particular subpopulation. In certain embodiments, the baseline level or activity of a target biomarker is determined using the same method that is subsequently used to determine the post-neuromodulation level or activity of the target biomarker. In certain embodiments, changes in target biomarker level or activity are calculated based on the difference between baseline level or activity and post-neuromodulation level or activity. For example, the differential (delta) in target biomarker expression levels can be the difference between target biomarker expression at a specific timepoint pre- and post-neuromodulation.

Target biomarkers for use in the methods disclosed herein may exhibit a two-fold or greater change in level or activity in response to neuromodulation. For example, a target biomarker may be a protein that exhibits a two-fold or greater increase or decrease in expression or secretion following neuromodulation. In certain of these embodiments, a target biomarker exhibits a three-fold or greater, five-fold or greater, or ten-fold or greater change in level or activity in response to neuromodulation.

In certain embodiments, target biomarkers for use in the methods disclosed herein exhibit a change in level or activity within a predetermined timeframe post-neuromodulation. In certain embodiments, the methods provided herein allow for real-time or relatively contemporaneous monitoring of neuromodulation efficacy. Accordingly, certain target biomarkers for use in the methods disclosed herein may exhibit a change in level or activity at the time of neuromodulation or relatively contemporaneous to neuromodulation. For example, in certain embodiments a target biomarker exhibits a change in level or activity within 1 minute, 2 minutes, 5 minutes, 10 minutes, 15 minutes, or 30 minutes of neuromodulation. Accordingly, in certain embodiments, post-neuromodulation level or activity for a target biomarker is determined during neuromodulation or relatively contemporaneous to neuromodulation, i.e., within 1 minute, 2 minutes, 5 minutes, 10 minutes, 15 minutes, or 30 minutes of neuromodulation. In preferred embodiments, post-neuromodulation level or activity for a target biomarker is determined in an acute timeframe, i.e., while the subject is still catheterized and/or under anesthesia. Alternatively or in addition to a change in level or activity at the time of neuromodulation or relatively contemporaneous to neuromodulation, a target biomarker may exhibit a change in level or activity at a later timepoint (e.g., at a chronic timepoint). For example, in certain embodiments a target biomarker exhibits a change in level or activity within 2 hours, 4 hours, 6 hours, 8 hours, 12 hours, 24 hours, 48 hours, 72 hours, 7 days, 14 days, one month, two months, four months, or one year of neuromodulation. Accordingly, in certain embodiments, post-neuromodulation level or activity for a target biomarker is determined 2 hours or more after neuromodulation, i.e., within 2 hours, 4 hours, 6 hours, 8 hours, 12 hours, 24 hours, 48 hours, 72 hours, 7 days, 14 days, one month, two months, four months, or one year of neuromodulation. In certain embodiments, changes in target biomarker level or activity at these later timepoints can be used to assess or classify a subject's response to neuromodulation. The resultant information can be used to develop predictive models for determining whether neuromodulation is likely to be effective in a particular subject or subpopulation.

The methods disclosed herein may be used to monitor the efficacy of neuromodulation carried out using a variety of suitable techniques. The neuromodulation, for example, may be electrically-induced, thermally-induced, chemically-induced, or induced in another suitable manner or combination of manners at one or more suitable treatment locations during a treatment procedure. For example, neuromodulation may be carried out by delivering monopolar or bipolar radio frequency (RF) energy, microwave energy, laser light or optical energy, magnetic, ultrasound energy (e.g., intravascularly delivered ultrasound, extracorporeal ultrasound, high frequency ultrasound (HIFU)), direct heat energy, and/or cryotherapeutic energy to target tissue at a treatment location to induce one or more desired effects at the treatment location. A treatment location may be a location proximate to one or more nerves being neuromodulated. In some embodiments, the treatment location is in or near a vessel or other body lumen. For example, a treatment location for renal neuromodulation may be at or near the renal artery. In certain embodiments, the identity of the target biomarkers may vary depending on the neuromodulation method being used. For example, neuromodulation using RF energy may result in changes in the level or activity of a different set of target biomarkers than cryotherapy. In other embodiments, a specific target biomarker or set of target biomarkers may be effective for monitoring efficacy across a range of neuromodulation techniques.

In certain embodiments, changes in target biomarker level or activity can be used in the prognosis of co-morbidities that are directly or indirectly benefited by neuromodulation. In other embodiments, changes in target biomarker level or activity can be used to predict a subject's response to neuromodulation.

Determination of baseline and/or post-neuromodulation target biomarker level or activity may be carried out using any previously known method and/or methods disclosed herein. In some embodiments, for example, determination of target biomarker level or activity utilizes a detection method that produces results in an acute timeframe following neuromodulation. Where a target biomarker is a secreted or cell surface biomolecule, determination of target biomarker level or activity may utilize one or more capture or detection agents. Where a target biomarker is an intracellular biomolecule, determination of target biomarker level or activity may utilize imaging/spectroscopy techniques that allow level or activity to be assessed in a non-invasive manner. In other embodiments, the level or activity of an intracellular target biomarker may require tissue sampling.

Figure 4:
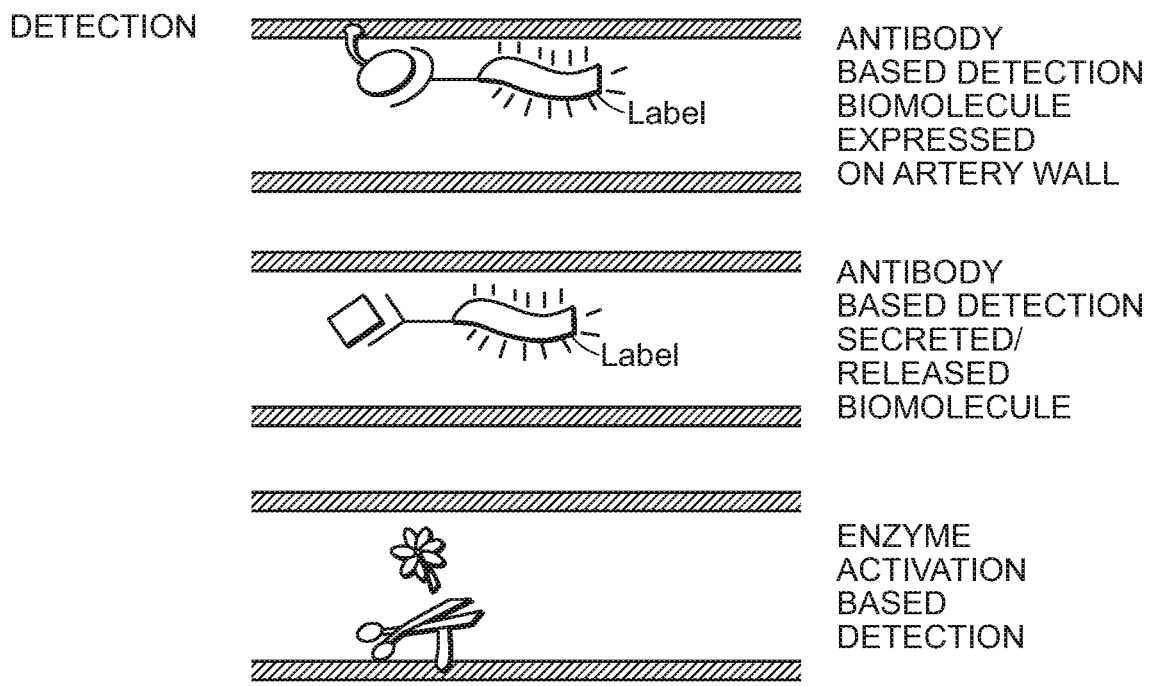
FIG. 4: Examples of target biomarker detection methods: antibody-based detection of artery wall proteins (upper panel), antibody-based detection of secreted proteins (middle panel), and activity-based detection of enzyme activity (lower panel).

In certain embodiments, determination of baseline or post-neuromodulation level of a target biomarker may be carried out using one or more capture agents that specifically bind the target biomarker, such as an antibody or an epitope-binding fragment thereof (see, e.g., FIG. 4; labeled antibody binding artery wall (upper panel) or secreted (lower panel) target biomarker), a ligand for the target biomarker, a receptor for which the target biomarker is a ligand, a nucleic acid complementary to an mRNA sequence encoding the target biomarker, or any other agent that specifically binds a target biomarker. In these embodiments, the target biomarker is detected based on binding to the capture agent.

Determination of baseline or post-neuromodulation activity of a target biomarker may be carried out using a detection agent that has a functional interaction with the target biomarker, such as a substrate for the target biomarker or an enzyme or catalytic antibody for which the target biomarker is a substrate (see, e.g., FIG. 4; scissors represent enzymatic detection agent capable of cleaving target biomarker). In these embodiments, target biomarker activity is detected based on presence of a specific function (e.g., substrate conversion). Alternatively, determination of target biomarker activity may be carried out using a capture agent specific for an enzymatic product or by-product of the target biomarker.

Capture or detection agents for use in determining the activity of a target biomarker may be in solution, or they may be immobilized on a surface such as a bead, resin, or one or more surfaces of a neuromodulation or other treatment device, a component thereof, or a separate capture device. Examples of suitable resins include, for example, hydrophobic resins, cation/anion exchange resins (e.g., carboxymethyl, sulfopropyl/diethylamine), immobilized metal affinity chromatography (IMAC) resins, and polar chromatographic resins (e.g., silica gel). In those embodiments that utilize a surface such as a bead or resin, all capture agents on the surface may be specific for a single target biomarker. Alternatively, capture or detection agents for multiple target biomarkers may be present on a single surface, allowing for simultaneous detection and analysis of multiple target biomarkers. In those embodiments wherein capture or detection agents are immobilized on one or more surfaces of a treatment device, a component thereof, or a separate capture device, the capture or detection agents may be on the outside of the device, i.e., in direct contact with arterial blood or the artery wall. In other embodiments, the capture or detection agents may be on an internal surface, such as the interior of a catheter or a capture compartment.

Figure 5:
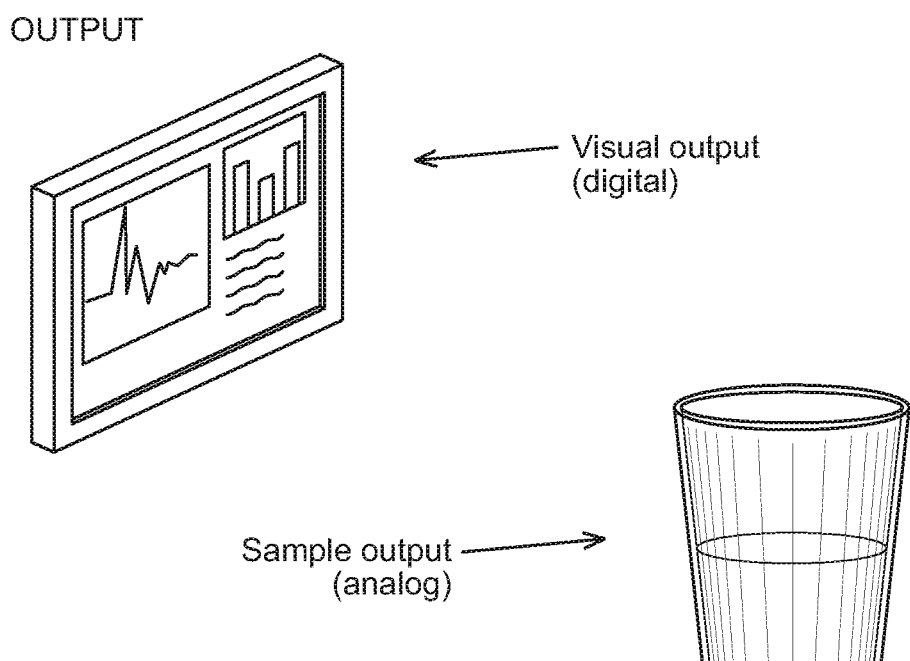
FIG. 5: Illustrative digital and analog outputs for displaying a detectable signal generated by the interaction of a target biomarker with a capture or detection agent.

In certain embodiments, binding of a target biomarker to a capture agent and/or interaction of the target biomarker with a detection agent results in a quantifiable signal. This quantifiable signal may be, for example, a colorimetric, fluorescent, heat, energy, or electric signal. In certain embodiments, this signal may be transduced to an external visual output device (see, e.g., FIG. 5). In certain embodiments, a capture or detection agent may be labeled, such as for example with an enzymatic or radioactive label. A capture or detection agent may be a binding substrate for a secondary capture agent, such as a labeled antibody.

Figure 6:
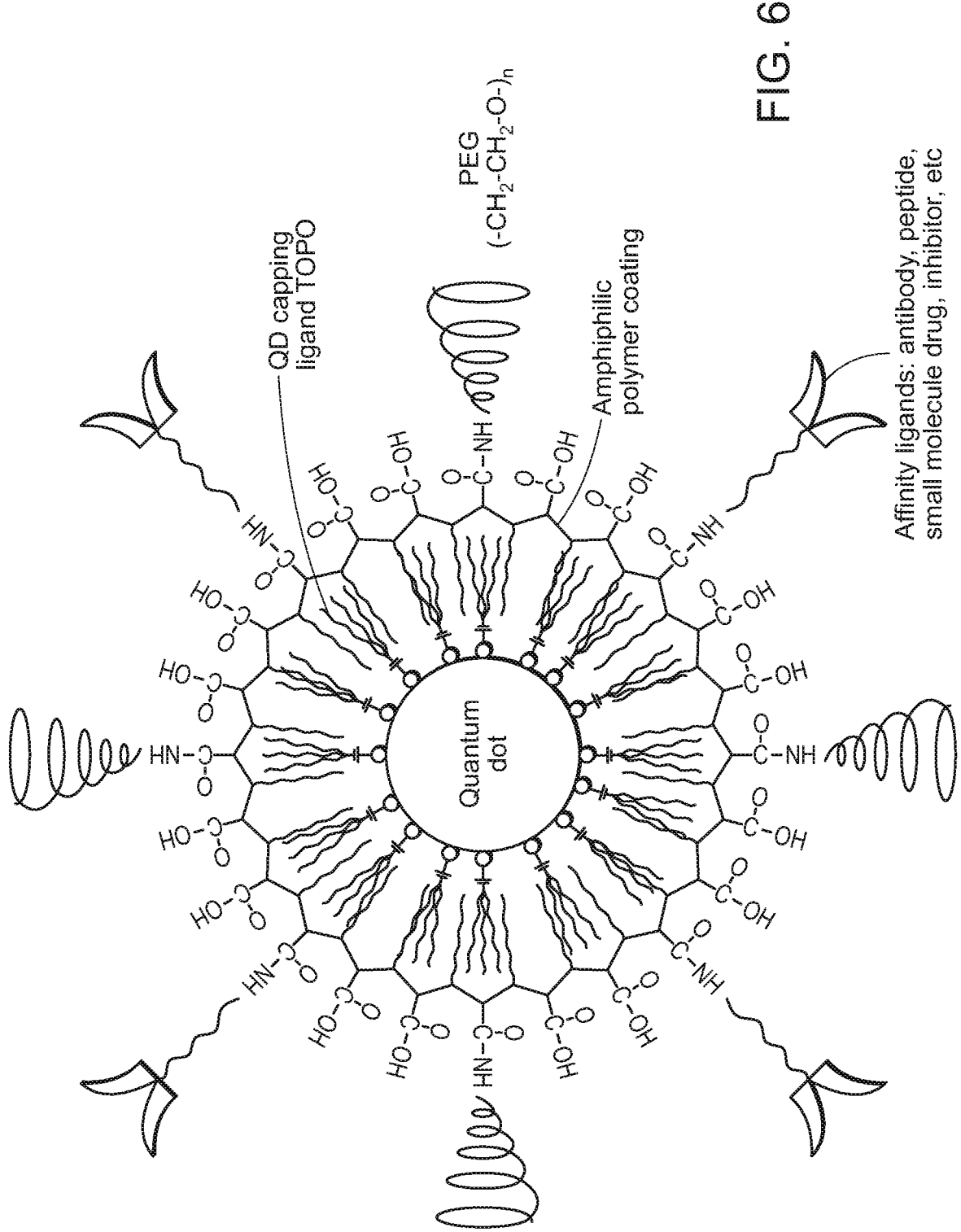
FIG. 6: Quantum dot system for generation of a detectable signal following binding of a target biomarker to an affinity ligand capture agent.

In certain embodiments, binding of a target biomarker to a capture agent results in a signal that which can be transduced to an external monitoring device. For example, binding of a target biomarker to a capture or detection agent may be detected using a high sensitivity fluorescence technique such as a resonance energy transfer method (e.g., Forster resonance energy transfer, bioluminescence resonance energy transfer, or surface plasmon resonance energy transfer). FIG. 6 illustrates a quantum dot embodiment for generating a signal based on binding of a target biomolecule to an affinity ligand capture agent (e.g., an antibody, peptide, small molecule drug, or inhibitor). Quantum dots are nanometer sized semiconductor crystals that fluoresce when excited with the proper frequency of light (see, e.g., Xing Nat Protoc 2:1152 (2007)). The emitted light is tuned by the size of the nanocrystal, and excitation frequencies range from near IR to UV. Dynamic visualization through skin has been demonstrated in animals using near IR radiation.

Figure 7:
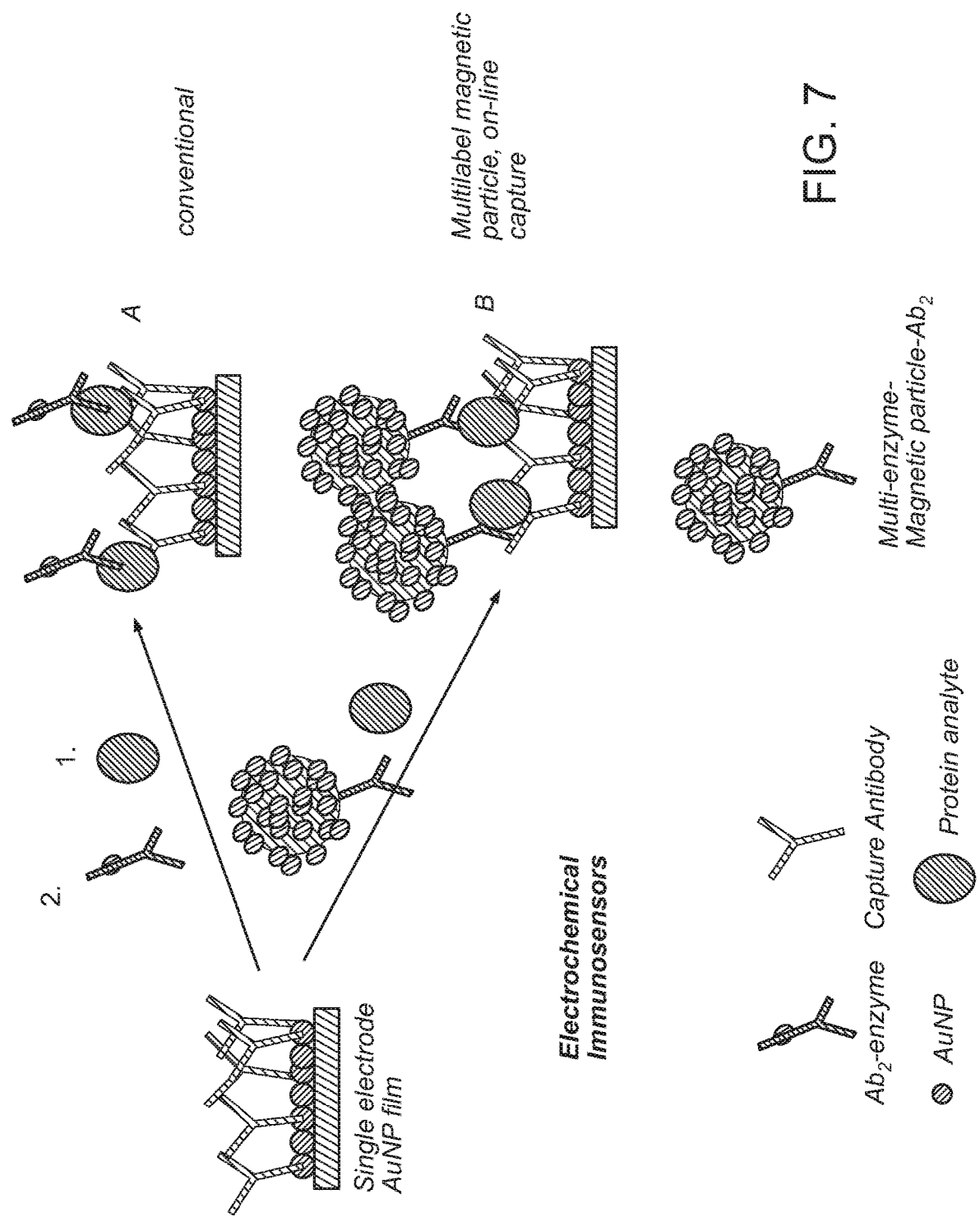
FIG. 7: Illustration of representative electrochemical immunosensor protocols.

In certain embodiments of the methods disclosed herein, determination of baseline and/or post-neuromodulation target biomarker level or activity is carried out using any immunoassay-based method. For example, target biomarker levels may be determined using an electrochemical immunosensor (see, e.g., FIG. 7), which provides concentration-dependent signaling (see, e.g., Centi Bioanalysis 1:1271 (2009); Rusling Analyst 135:2496 (2010)). Antibodies for use in an immunoassay-based determination of target biomarker level or activity may be labeled or unlabeled.

Determination of baseline and/or post-neuromodulation target biomarker level or activity may take place in vivo in some embodiments. For example, the determination may be carried out using the same device that is used to carry out neuromodulation or a component attached to the treatment device. Alternatively, determination of biomarker level or activity may be carried out using a separate device. In certain of these embodiments, the separate device can be delivered to the neuromodulation site via the same catheter used to deliver the treatment device. In other embodiments, however, determination of baseline and/or post-neuromodulation target biomarker level or activity takes place ex vivo.

Figure 8:
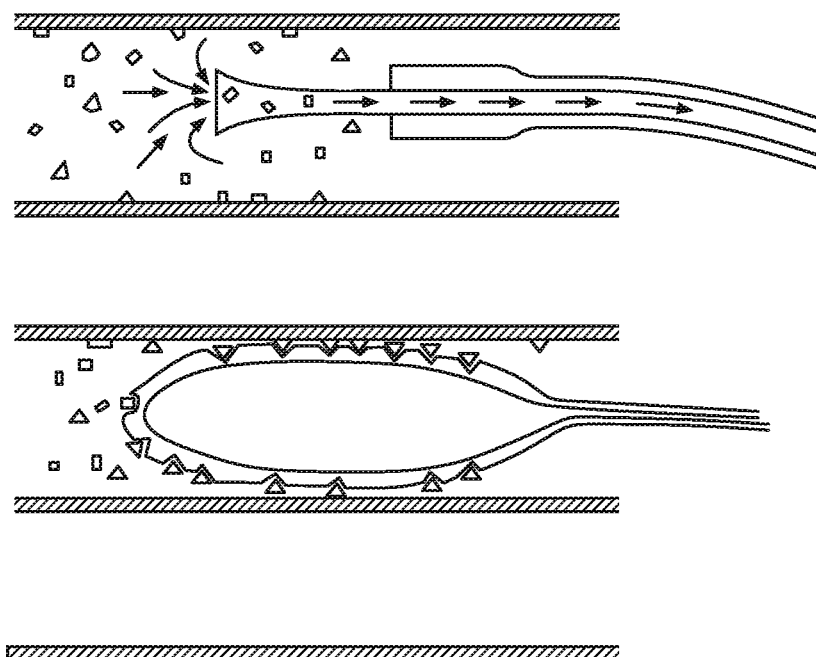
FIG. 8: Illustrative target biomarker capture methods: (a) removal from neuromodulation site and sequestration in a capture compartment for analysis in vivo or ex vivo (upper panel) and (b) balloon-based/semi-permeable filtering device with antibody based/immuno-electrochemical technology embedded within for capture and analysis in vivo or ex vivo (lower panel).

In some embodiments, the interaction between a target biomarker and a capture or detection agent takes place at or near the neuromodulation site, e.g., near the renal artery. In certain of these embodiments, a target biomarker binds to a capture or detection agent in the bloodstream or at the surface of the arterial wall. In these embodiments, the capture or detection agent may be in solution (i.e., in the bloodstream) or immobilized to a surface that is in contact with the bloodstream and/or arterial wall. For example, a device or component thereof in which a capture or detection agent is integrated may be a balloon coated with one or more detection molecules that inflates to touch the ablated artery wall (see, e.g., FIG. 8, lower panel). Captured target biomarkers may be detected in vivo, or the balloon-based device may be removed for target biomarker detection ex vivo.

In other embodiments, however, the interaction between a target biomarker and a capture or detection agent can take place away from the neuromodulation site. For example, target biomarkers may be removed from a neuromodulation site and sequestered in a capture compartment (see, e.g., FIG. 8, upper panel). In those embodiments that utilize a capture compartment, the capture compartment may be located in vivo or ex vivo. In certain of these embodiments, the capture compartment may be located in vivo initially, then removed from the body for analysis (i.e., removed from the body prior to contact with capture or detection agents). In certain embodiments, a target biomarker may be contacted with capture or detection agents inside the capture compartment. In other embodiments, exposure to capture or detection agents may take place after a biological sample has been removed from the capture compartment. In certain embodiments, target biomarkers may be concentrated prior to or simultaneous with exposure to capture or detection agents. In those embodiments that utilize a capture compartment, concentration may be carried out within the capture compartment or after the biological sample has been removed from the capture compartment. In certain embodiments, concentration of target biomarkers may be carried out using one or more filters integrated into the capture device or capture compartment. For example, a first filter at the distal end of a capture compartment may be selected such that it allows passage of the target biomarker into the capture compartment while preventing passage of other biomolecules. A second filter at a proximal end of the capture component may be selected such it prevents passage of the target biomarker out of the capture compartment while allowing blood to flow out of the capture compartment. Through the use of one or more filters, a target biomarker may be concentrated within the capture compartment. Alternatively or in addition to the use of filters, one or more additional steps may be taken to concentrate target biomarkers in the capture compartment or after removal from the capture compartment. For example, target biomarkers may be concentrated using beads.

A representative embodiment of a target biomarker detection method and device is set forth in FIG. 9. In this embodiment, a blood sample containing secreted target biomarkers A and B is captured from near the ablation sites using a catheter based capture device (FIG. 9A), as will be described in more detail below. This capture step results in sequestration of the target biomarkers in a capture compartment wherein the biomarkers are concentrated. The target biomarkers bind to one or more immobilized capture agents on the inner surface of the capture compartment (FIG. 9B). Binding of the target biomarkers to the immobilized capture agents results in a signal that is transduced to an ex vivo device via an output generator (FIG. 9C). Examples of devices for carrying out these and other embodiments are described in more detail below with reference to FIGS. 51-56D.

Figure 10:
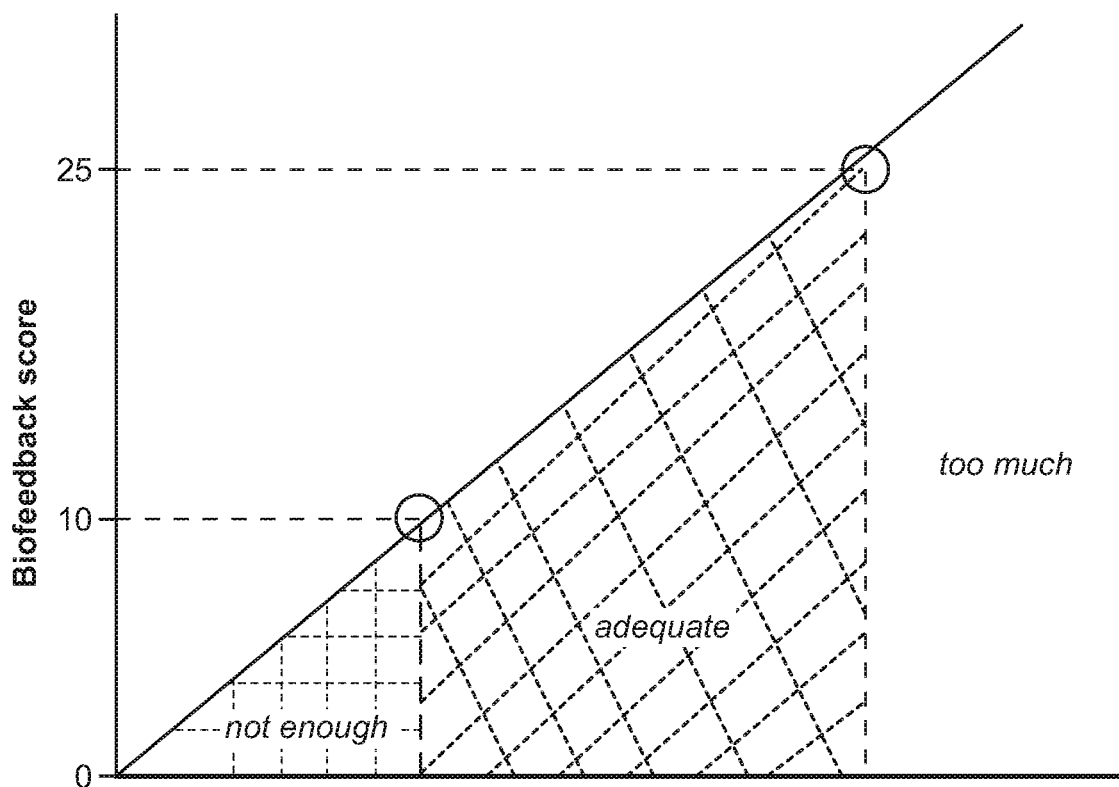
FIG. 10: Illustration of biofeedback score for determining the likelihood of success of a renal neuromodulation procedure.

In certain embodiments, the methods provided herein produce a biofeedback score indicating to a practitioner the likelihood that a neuromodulation procedure was successful. For example, a biofeedback score falling within a certain range indicates that the procedure was likely successful, while a score falling outside this range indicates that the procedure was unsuccessful (see, e.g., FIG. 10). In other embodiments, the methods provided herein provide a binary "yes or no" indicator of the success of a neuromodulation procedure. In these embodiments, a specific threshold increase or decrease in the level or activity of a target biomarker or set of target biomarkers indicates the neuromodulation procedure was successful. In certain of these embodiments, the specific threshold change indicates that the neuromodulation procedure was successful with a specific confidence interval (e.g., 95% or greater, 97% or greater, or 99% or greater). In some embodiments, information regarding changes in the level or activity of a target biomarker may be combined with one or more additional parameters such as temperature, nerve signaling data, or impedance in assessing neuromodulation efficacy. Further, efficacy may be evaluated based on a combination of all parameters, with changes in target biomarker level or activity simply functioning as one of the parameters.

For example, as disclosed in Example 1 below, a set of candidate protein target biomarkers was screened in vivo to identify proteins exhibiting a change in expression level in renal tissue at various timepoints following ablation. This resulted in the identification of a set of secreted, cell surface, and intracellular protein target biomarkers that showed increased or decreased expression levels at 10 minutes, 24 hours, and 7 days post-ablation.

Examples of secreted protein target biomarkers that were upregulated within 10 minutes of ablation include brain-derived neurotrophic factor (BDNF), calcitonin-related polypeptide beta (CALCB, CGRP), CD40L ligand (CD40L, CD40LG), clusterin (CLU), endothelin-3 (EDN3), interleukin 10 (IL-10), and kalakrein B1 (KLKB1). Examples of cell surface protein target biomarkers that were upregulated within 10 minutes of ablation include selectin E (SELE) and DnaJ (Hsp40) homolog superfamily A member 4 (DNAJA4). Examples of intracellular protein target biomarkers that were upregulated within 10 minutes of ablation include BTG2 family member 2 (BTG2), DNAJA4, DnaJ (Hsp40) homolog superfamily B member 1 (DNAJB1), FBJ murine osteosarcoma viral oncogene homolog (FOS), heat shock 27 kDa protein 1 (HSPB1), heat shock 60 kDa protein 1 (HSPD1), and heat shock 105 kDa/110 kDa protein 1 (HSPH1).

Examples of secreted protein target biomarkers that were upregulated within 24 hours of ablation include bone morphogenetic protein 7 (BMP7), IL-10, tumor necrosis factor receptor superfamily member 1B (TNFRSF1B), and leukemia inhibitor factor (LIF). Examples of cell surface protein target biomarkers that were upregulated within 24 hours of ablation include ATPase/Na/K transporting alpha 1 polypeptide (ATP1A1), endothelin receptor type B (ETB, EDNRB), integrin alpha M (ITGAM, CD11b), solute carrier family 2 (facilitated glucose/fructose transporter) member 5 (SLC2A5/GLUT5), SELE, Toll-like receptor 4 (TLR4), and TNFRSF1B. Examples of surface protein target biomarkers that were downregulated within 24 hours of ablation include melanocortin 2 receptor (MC2R). Examples of intracellular protein target biomarkers that were upregulated within 24 hours of ablation include heme oxygenase (decycling) 1 (HMOX-1), heat shock 70 kDa protein 5 (HSPA5), HSPD1, HSPH1, ATP1A1, and superoxide dismutase 2 (SOD2).

Examples of secreted protein target biomarkers that were upregulated within 7 days of ablation include natriuretic peptide B (BNP), CD40L, CLU, Fas ligand (FASLG), IL-10, TNFRSF1B, and LIF. Examples of secreted protein target biomarkers that were downregulated within 7 days of ablation include neurotrophin 3 (NTF3). Examples of cell surface protein target biomarkers that were upregulated within 7 days of ablation include ATP1A1, EDNRB, ITGAM, purinergic receptor P2Y G-protein coupled 12 (P2RY12), SELE, SLC2A5/GLUT5, Toll-like receptor 3 (TLR3), TLR4, Toll-like receptor 7 (TLR7), and TNFRSF1B. Examples of cell surface protein target biomarkers that were downregulated within 7 days of ablation include adrenergic alpha 2B receptor (ADRA2b). Examples of intracellular protein target biomarkers that were upregulated within 7 days of ablation include CDKN2B (p15), HMOX-1, heat shock 70 kDa protein 14 (HSPA14), ATP1A1, and HSPD1. Examples of intracellular protein target biomarkers that were downregulated within 7 days of ablation include CDKN1B (p27).

As disclosed in Example 2 below, a set of candidate protein target biomarkers was screened in vitro to identify proteins exhibiting a change in expression or secretion level at 1, 5, and 10 minutes after exposure to heat, inflammation, or a combination thereof. This resulted in the identification of a set of protein target biomarkers that showed increased expression or secretion levels at 1, 5, or 10 minutes post-ablation. Examples of protein target biomarkers that exhibited an increase in expression include caspase 10 (CASP10), CCL13 (MCP4), CCND1, CD70, alpha B crystalline (CRYAB), CPS1, DNAJB1, DNAJB11, heat shock 70 kDa protein 1A (HSPA1A), heat shock 70 kDa protein 1B (HSPA1B), heat shock protein B6 (HSPB6), IL-10, KIT, lymphotoxin alpha (LTA), myosin light chain kinase 3 (MYLK3), NODAL, NPY1R, POU1F1, and TCP-1-alpha (TCP1). Examples of protein target biomarkers that exhibited an increase in secretion include actin, cytoplasmic (ACTA2), S100 calcium binding protein A6 (CACY/2A9), cofilin-1 (CFL1), protein cTAGE-2 (CTAG1A1/CTAG21), L-lactate dehydrogenase (LDHA), transmembrane protein 141 (MGC141/TMEM141), N-alpha-acetyltransferase 20 (NAA20/NAT5), nucleoside diphosphate kinase B (NM23B), phytanoyl-CoA deoxygenase, peroxisomal (PAHX/PHYH1), prefoldin subunit 1 (PFDN1), serine/threonine protein kinase (PLK-2), tubulin alpha-1B-chain (TUBA1B), and vimentin (VIM).

As further disclosed in Example 2, a set of candidate protein target biomarkers was screened by treating a set of neuronal cells with heat, inflammation, or a combination thereof, then treating a set of endothelial cells with the neuronal cell secretome, i.e., conditioned media from the heat/inflammation treated neuronal cells. This conditioned media contains neuronal protein and non-protein stress factors that exhibit increased secretion after heat/inflammation treatment. Alternatively, the endothelial cells were treated directly with recombinant factors including neurotropic factor or angiogenic growth factors (e.g., BDNF, FGF5). Examples of protein target biomarkers that exhibited an increase in expression in the second set of cells include synuclein alpha (SNCA), BDNF, ciliary neurotrophic factor (CNTF), fibroblast growth factor 2 (basic) (FGF2), glial cell-derived factor 2 (basic) (GDNF), beta nerve growth factor 2 (NGF2), neurotrophin-3 (NTF3), PF4, EDN2, ACE2, interferon gamma (IFN-γ), artemin (ARTN), LIF, cerebellin 1 precursor (CBLN1), neuregulin 1 (NRG1), neuregulin 2 (NRG2), neuregulin 4 (NRG4), persephin (PSPN), NTF4, and transforming growth factor alpha (TGFA).

As disclosed in Example 3 below, an additional set of protein and non-protein candidate target biomarkers will be screened in vivo to identify potential target biomarkers exhibiting a change in renal arterial or venous blood levels at various timepoints following ablation. As set forth in Example 3, an initial evaluation using this screen was carried out using NE and CFL1. Additional candidate target biomarkers that may be evaluated in this screen include NPY, DBN, $Ca^{2+}$, renin, dopamine beta-hydroxylase (DBH), angiotensin (AGT), endothelin 1, 2, and 3, neurotensin (NTS), and amyloid beta (A4) precursor protein (APP).

In certain embodiments, the methods disclosed herein utilize one or more of the target biomarkers listed above from the in vivo and in vitro studies to evaluate the efficacy of renal neuromodulation. Provided herein in certain embodiments are compositions comprising capture or detection agents specific to one or more of these target biomarkers, as well as kits, panels, and arrays comprising such capture or detection agents.

The following examples are provided to better illustrate the disclosed technology and are not to be interpreted as limiting the scope of the technology. To the extent that specific materials are mentioned, it is merely for purposes of illustration and is not intended to limit the technology. It will be understood that many variations can be made in the procedures herein described while still remaining within the bounds of the present technology. It is the intention of the inventors that such variations are included within the scope of the technology.

EXAMPLES

Example 1: In Vivo Target Biomarker Screening (Porcine Renal Tissue)

Gene expression studies were conducted in renal artery tissue samples from domestic swine to identify candidate target biomarkers that exhibit a change in expression level at various time points after renal denervation/ablation.

Animals were broken into three groups of three animals each: naïve (no treatment), sham (catheterized but not ablated), and treated (subject to ablation at 65° C. and 90 seconds using a spiral ablation catheter device). Left and right renal arteries and surrounding tissue samples were obtained by sampling tissue in the area of ablation at 10 minutes ("day 0"), 7 days, or 24 hours post-treatment. Slices from the center of ablation sites were removed for histopathological analysis, and the ablation sites were cleaned up by removing any non-ablated tissue and pooled. Tissue was maintained during the dissection process using RNALater.

Pooled tissue samples were weighed and mixed under frozen conditions, and then added to round-bottomed tubes containing 2× stainless steel beads (5 mm diameter) at room temperature. 900 μL QIAzol lysis reagent was added to each tube, and the tissue was macerated using the TissueLyser II Adaptor Set with disruption at 30 Hz (3×2 minutes) to release RNA. An additional 300 μL of lysis buffer was added to each tube, and the disruption cycle was repeated (1×2 minutes at 30 Hz). Lysates were transferred to new Eppendorf tubes for mRNA isolation.

120 μl gDNA Eliminator Solution was added to each lysate sample, and tubes were shaken vigorously for 15 seconds. 180 μL of chloroform was added, and tubes were again shaken vigorously for 15 seconds. After 2-3 minutes at room temperature, tubes containing homogenate were centrifuged at 12,000×g for 15 minutes at 4° C. The centrifuge was warmed to room temperature, and the upper aqueous phase was transferred to a new Eppendorf tube. An equal volume of 70% ethanol was added to each tube with thorough mixing, and 700 μL of each sample was transferred to an RNeasy Mini spin column in a 2 mL collection tube. Samples were centrifuged for 15 seconds at >8000×g (>10,000 rpm) at room temperature and flow-thru was discarded. The ethanol mixing and RNeasy centrifugation steps were repeated until all sample was used up. 700 μL of Buffer RWT was added to each spin column, followed by centrifugation for 15 seconds at >8,000×g (>10,000 rpm) to wash the membrane. Flow-thru was discarded, and 500 μL Buffer RPE was added each spin column, followed by centrifugation for 15 seconds at >8,000×g (>10,000 rpm). Flow thru was discarded, and 500 μl Buffer RPE was again added to each spin column, followed by centrifugation for 2 minutes at >8,000×g (>10,000 rpm) to wash the membrane. RNeasy spin columns were placed in a new 2 mL collection tube and centrifuged at full speed for 1 minute. The spin column was placed in a new 1.5 mL collection tube, 50 μL RNase free water was added directly to the spin column membrane, and RNA eluted was eluted by centrifugation for 1 minute at >8,000×g (>10,000 rpm). This step was repeated using another 50 μL of RNase free water. To ensure significance, A260 readings were verified to be greater than 0.15. An absorbance of 1 unit at 260 nm corresponds to 44 μg of mRNA per mL (A260=1=44 μg/mL) at neutral pH.

ABI High Capacity cDNA kits were used to convert mRNA to cDNA for quantitative real-time PCR (qPCR). PCR was performed in optical 384-well plates, freshly prepared on the Eppendorf epMotion liquid handler. Final reaction volume was 20 μL (4 μL Taqman Assay+mixture of 6 μL cDNA (3 ng)+10 μL Universal Master Mix with UNG). Assays were performed to include+RT (reverse transcriptase) samples and, when appropriate, a-RT control. Endogenous controls (×2) were run in triplicate and animal samples were run only once for screening purposes. The real-time PCR protocol included an initial step of 50° C. (2 minutes) to activate the DNA polymerase, denaturation by a hot start at 95° C. for 10 minutes, and 40 cycles of a two-step program (denaturation at 95° C. for 15 seconds for primer annealing/extension at 60° C. for 1 minute). Fluorescence data was collected at 60° C. Fluorescence was quantified with the ABI PRISM 7900HT, and the resultant data was analyzed using SDS RQ Manager (1.2.1) Software (Sequence Detection System Software, Applied Biosystems). Each candidate target biomarker was checked, and threshold and baseline was adjusted to produce (in Δ Rn versus Cycle) an amplification curve of the type suggested by Applied Biosystems in their "Relative Quantification Using Comparative Ct Getting Started Guide." A calibrator was selected for calculation of the RQ (relative quantification). The calibrator was based on an average of 6× figures from the three naïve animals, left & right arteries, resulting in a numerical result of 1 for the naïve RQ. For calculation of the RQ for the standard deviation (SD) of the naïves, any other experimental animal was used as a calibrator (generally the first animal for Day 0 treated). RQ averages of animals (×3) in the same treatment group were calculated for each point and for each candidate target biomarker individually, and plotted in bar graphs.

Figure 11:
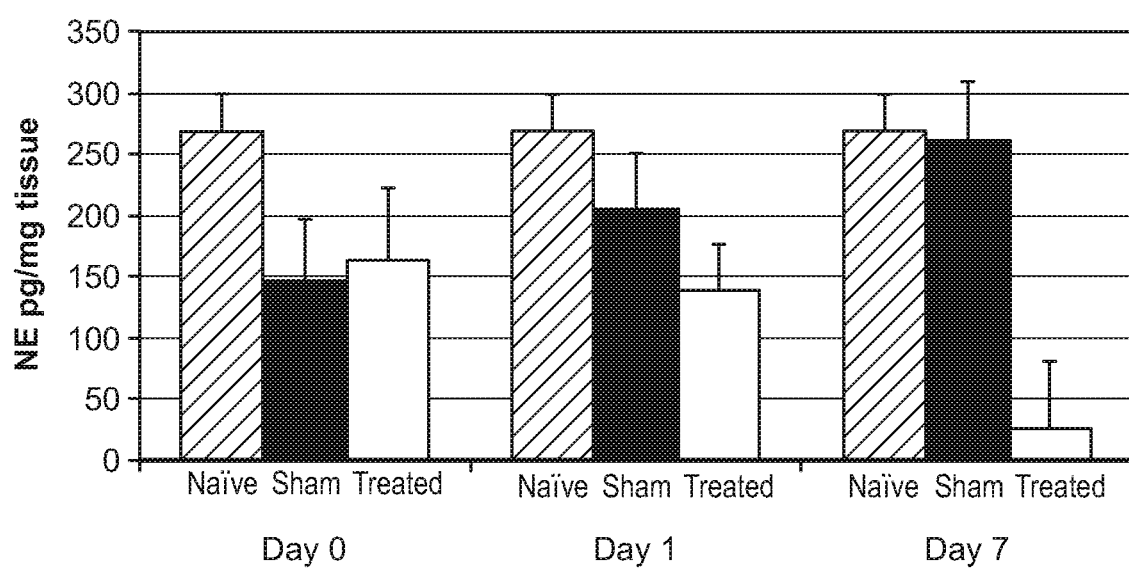
FIG. 11: Average kidney NE levels post-ablation.

Renal NE and dopamine (DBN) levels in naïve, sham, and test animals were evaluated at 10 minutes, 24 hours, and 7 days. Average kidney NE production post-ablation is shown in FIG. 11. Candidate genes were evaluated for their ability to provide a graded response that correlates with NE production.

The initial screen was carried out using the 70 candidate target biomarkers set forth in Table 1. Shaded genes exhibited an increase or decrease in expression within 10 minutes, 24 hours, and/or 7 days of ablation. Preferred target biomarkers are those exhibiting at least a two-fold change in expression within 10 minutes of ablation. From the initial screen, this group included the genes BDNF, CALCB, CD40L, CLU, EDN3, IL-10, KLKB1, SELE, DNAJA4, BTG2, DNAJB1, FOS, HSPB1, HSPD1, and HSPH1. Of these, the most preferred biomarkers are the secreted proteins BDNF, CALCB, CD40L, CLU, EDN3, IL-10, and KLKB1. Additional screens may be carried out to evaluate candidate target biomarker expression at later time periods (e.g., 1 month, 6 months, or one year post-ablation) in order to validate efficacy as long-term target biomarkers and durability of changes in expression.

TABLE 1

Figure 12:
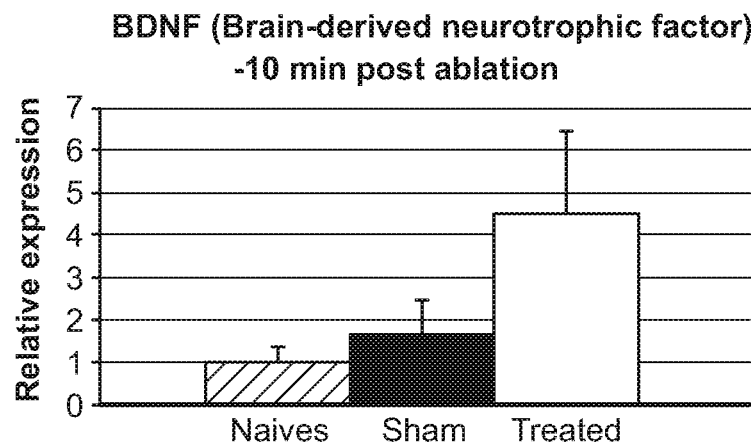
FIG. 12: Upregulation of BDNF 10 minutes post-ablation in endothelial cells.
Figure 13:
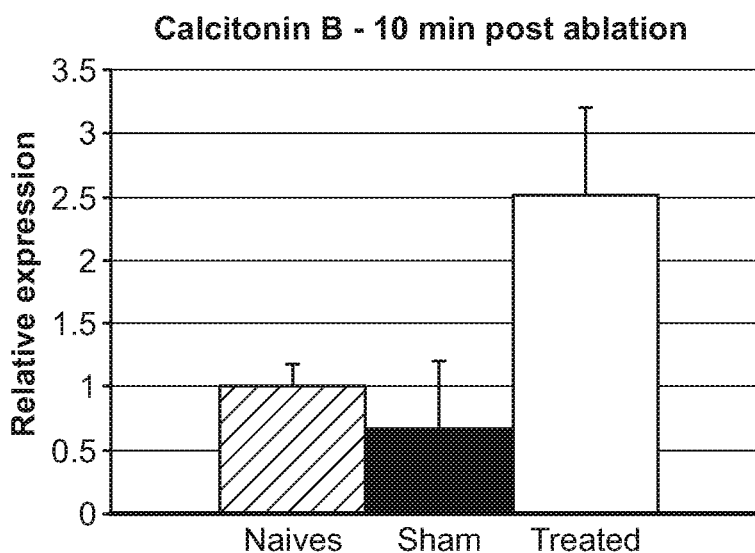
FIG. 13: Upregulation of CALCB 10 minutes post-ablation in endothelial cells.
Figure 14:
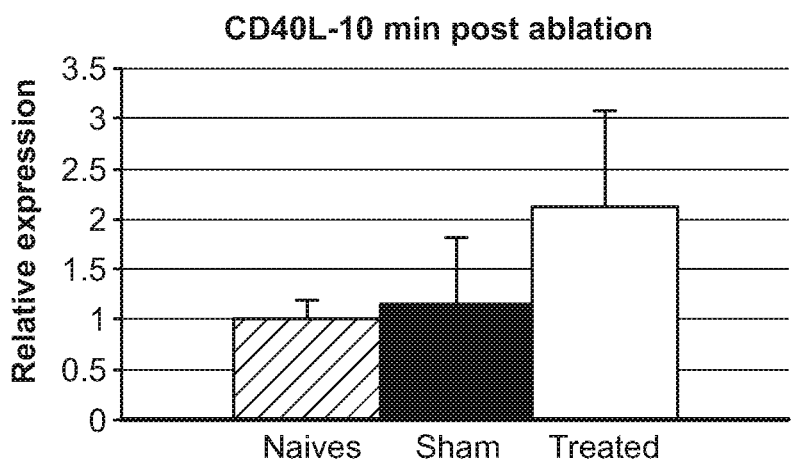
FIG. 14: Upregulation of CD40L 10 minutes post-ablation in endothelial cells.
Figure 15:
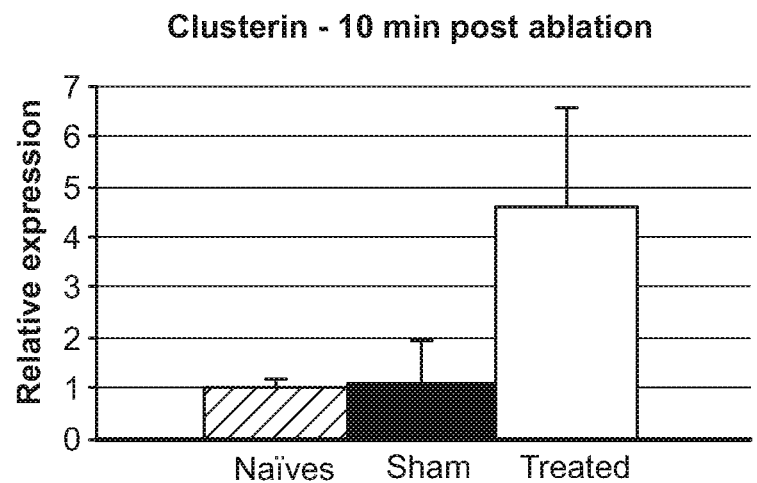
FIG. 15: Upregulation of CLU 10 minutes post-ablation in endothelial cells.
Figure 16:
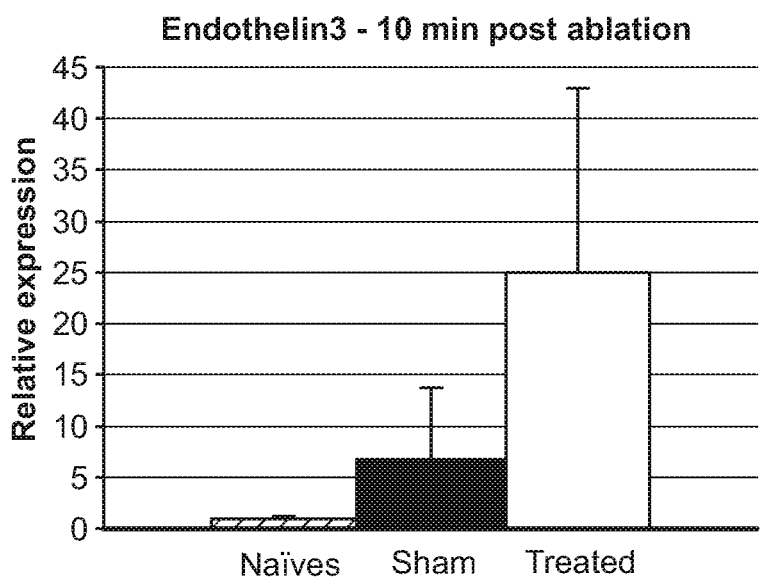
FIG. 16: Upregulation of EDN310 minutes post-ablation in endothelial cells.
Figure 17:
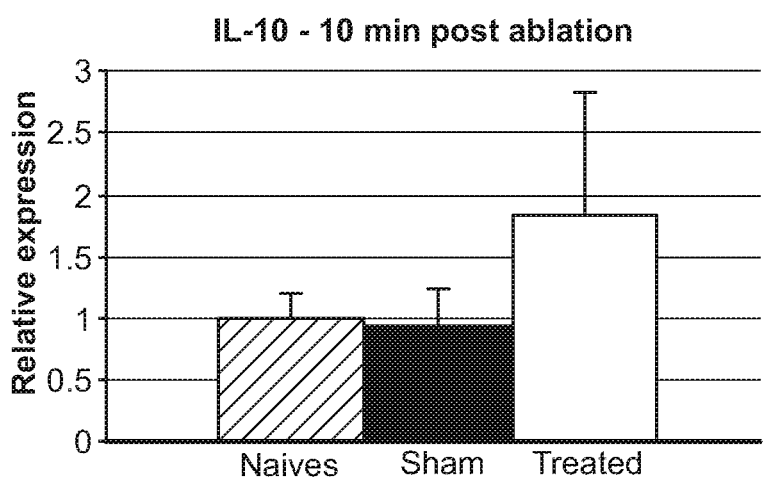
FIG. 17: Upregulation of IL-10 10 minutes post-ablation in endothelial cells.
Figure 18:
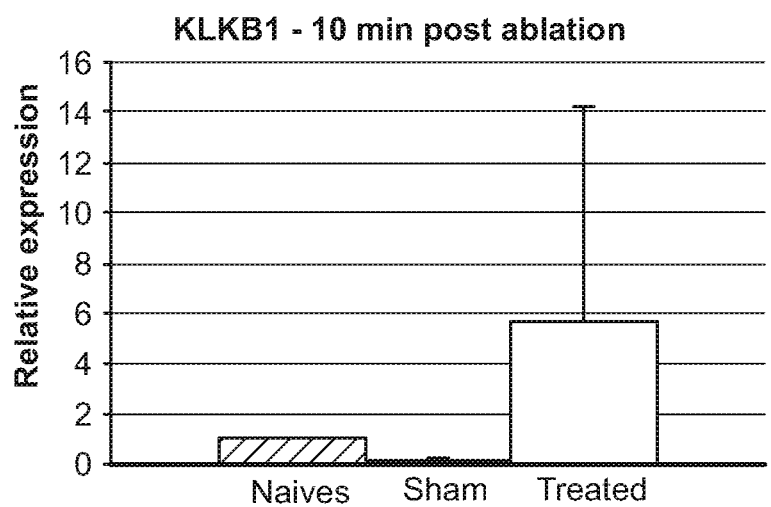
FIG. 18: Upregulation of KLKB1 10 minutes post-ablation in endothelial cells.

| Gene (Reference) | Location | Result | Gene Product Function/Description |
|---|---|---|---|
| BDNF (Frostick Microsurgery 18: 397 (1998); Heberlein Psychopharmacology (Berl) 209: 213 (2010)) | Secreted | Upregulated 10 minutes post-ablation (FIG. 12) | Promotes survival and differentiation of selected neuronal populations of the peripheral and central nervous system, participates in axonal growth and pathfinding and in modulation of dendritic growth and morphology |
| CALCB (Xie Hypertension 54: 1298 (2009); Xie J Pharmacol Exp Ther 325: 751 (2008)) | Secreted | Upregulated 10 minutes post-ablation (FIG. 13) | Potent vasodilator and hypotensor, potential neurotransmitter or neuromodulator role |
| CD40L (Jin Anticancer Drugs 23: 445 (2012)) | Secreted | Upregulated 10 minutes post-ablation (FIG. 14) Upregulated 7 days post-ablation | Pro-inflammatory and immunoregulatory functions |
| CLU (Lu Curr Med Chem 17: 957 (2010)) | Secreted | Upregulated 10 minutes post-ablation (FIG. 15) Upregulated 7 days post-ablation | Secreted chaperone (heatshock protein) |
| EDN3 (Paulis Nat Rev Cardiol 7: 431 (2010)) | Secreted | Upregulated 10 minutes post-ablation (FIG. 16) | Potent vasoconstrictive peptide |
| IL-10 (Zager Am J Physiol Renal Physiol 301: F1334 (2011); Lu Curr Med Chem 17: 957 (2010)) | Secreted | Upregulated 10 minutes post-ablation (FIG. 17) Upregulated 24 hours post-ablation Upregulated 7 days post-ablation | Anti-inflammatory cytokine with pleiotropic effects in immunoregulation and inflammation, inhibits synthesis of various cytokines including IFN-γ, IL-2, IL-3, TNF, and GM-CSF produced by activated macrophages and helper T-cells |
| KLKB1 (Paulis Nat Rev Cardiol 7: 431 (2010)) | Secreted | Upregulated 10 minutes post-ablation (FIG. 18) | Participates in surface-dependent activation coagulation, fibrinolysis, and inflammation, may play a role in the renin-angiotensin system by converting prorenin to renin (vasoconstriction) |

TABLE 1-continued

Figure 19:
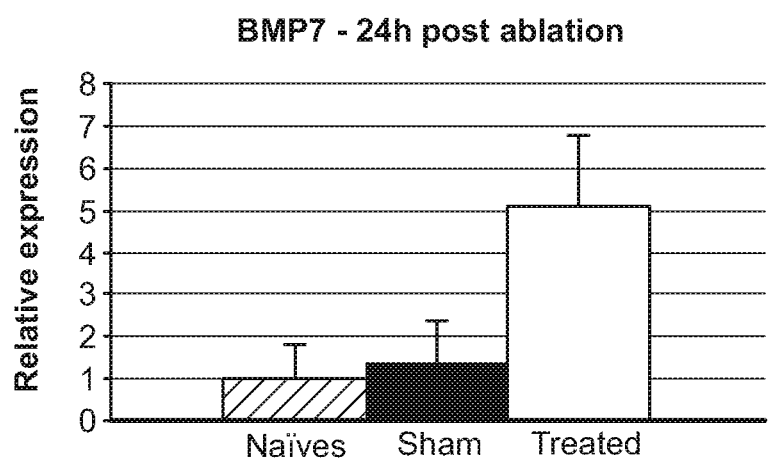
FIG. 19: Upregulation of BMP7 24 hours post-ablation in endothelial cells.
Figure 20:
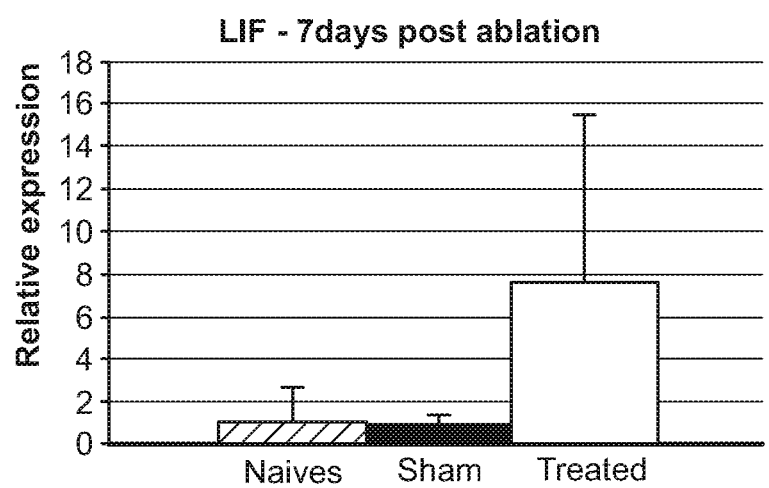
FIG. 20: Upregulation of LIF 7 days post-ablation in endothelial cells.

| Gene (Reference) | Location | Result | Gene Product Function/Description |
|---|---|---|---|
| SELE (Sonna J Appl Physiol 92: 1725 (2002)) | Surface | Upregulated 10 minutes post-ablation Upregulated 24 hours post-ablation Upregulated 7 days post-ablation | Endothelial cell adhesion molecular/inflammation |
| DNAJA4 (Sonna J Appl Physiol 92: 1725 (2002)) | Intracellular/ Surface | Upregulated 10 minutes post-ablation | Protein folding and heat response |
| BTG2 (Struckmann Cancer Res 64: 1632 (2004)) | Intracellular | Upregulated 10 minutes post-ablation | Anti-proliferative, regulator of neuron differentiation, transcriptional co-factor |
| DNAJB1 (Lu Curr Med Chem 17: 957 (2010)) | Intracellular | Upregulated 10 minutes post-ablation | Interacts with Hsp70, stimulates ATPase activity |
| FOS (Sonna J Appl Physiol 92: 1725 (2002)) | Intracellular | Upregulated 10 minutes post-ablation | Apoptosis, regulation of cell proliferation, differentiation, and transformation |
| HSPB1 (Lu Curr Med Chem 17: 957 (2010)) | Intracellular | Upregulated 10 minutes post-ablation | Stress resistance, actin organization |
| HSPD1 (Lu Curr Med Chem 17: 957 (2010)) | Intracellular | Upregulated 10 minutes post-ablation Upregulated 24 hours post-ablation Upregulated 7 days post-ablation | Chaperonin, involved in folding of mitochondrial matrix proteins |
| HSPH1 (Lu Curr Med Chem 17: 957 (2010)) | Intracellular | Upregulated 10 minutes post-ablation Upregulated 24 hours post-ablation | Prevents aggregation of denatured proteins under severe stress |
| BMP7 (Zeisberg Nephrol Dial Transplant 21: 568 (2006)) | Secreted | Upregulated 24 hours post-ablation (FIG. 19) | Member of TGFβ superfamily |
| LIF (Yoshino J Am Soc Nephrol 14: 3090 (2003)) | Secreted | Upregulated 24 hours post-ablation Upregulated 7 days post-ablation (FIG. 20) | Pleiotropic cytokine involved in nephrogenesis and ECM repair |
| ATP1A1 (Liu Mol Biol Rep 38: 83 (2011)) | Intracellular/ Surface | Upregulated 24 hours post-ablation Upregulated 7 days post-ablation | Establishes and maintains electrochemical gradients of $Na^+$ and $K^+$ across plasma membrane |
| EDNRB (Paulis Nat Rev Cardiol 7: 431 (2010)) | Surface | Upregulated 24 hours post-ablation Upregulated 7 days post-ablation | Involved in vasoconstriction, vasodilation, and cell proliferation |
| ITGAM (Pereira Hemodial Int 14: 295 (2010)) | Surface | Upregulated 24 hours post-ablation Upregulated 7 days post-ablation | Mediates inflammation and adhesion |
| MC2R (Paulis Nat Rev Cardiol 7: 431 (2010)) | Surface | Downregulated 24 hours post-ablation | Involved in energy homeostasis, inflammation, immunomodulation, and temperature control |
| SLC2A5/GLUT5 (Soleimani Acta Physiol (Oxf) 201: 55 (2011)) | Surface | Upregulated 24 hours post-ablation Upregulated 7 days post-ablation | Fructose transporter |
| TLR4 (Lu Curr Med Chem 17: 957 (2010)) | Surface | Upregulated 24 hours post-ablation Upregulated 7 days post-ablation | Pattern recognition receptor, involved in inflammation |
| TNFRSF1B (Mas Transplantation 85: 626 (2008)) | Secreted/ Surface | Upregulated 24 hours post-ablation Upregulated 7 days post-ablation | Involved in recruitment of anti-apoptotic proteins |
| HMOX1 (Sonna J Appl Physiol 92: 1725 (2002)) | Intracellular | Upregulated 24 hours post-ablation Upregulated 7 days post-ablation | Catalyzes degradation of heme, active during physiological stress |
| HSPA5 (SABiosciences $RT_2$ Profiler PCR Array Human Neurotoxicity platform) | Intracellular | Upregulated 24 hours post-ablation | Facilitates assembly of multimeric protein complexes in ER |
| SOD2 (SABiosciences $RT_2$ Profiler PCR Array Human Neurotoxicity platform) | Intracellular | Upregulated 24 hours post-ablation | Destroys superoxide anion radicals |

TABLE 1-continued

Figure 21:
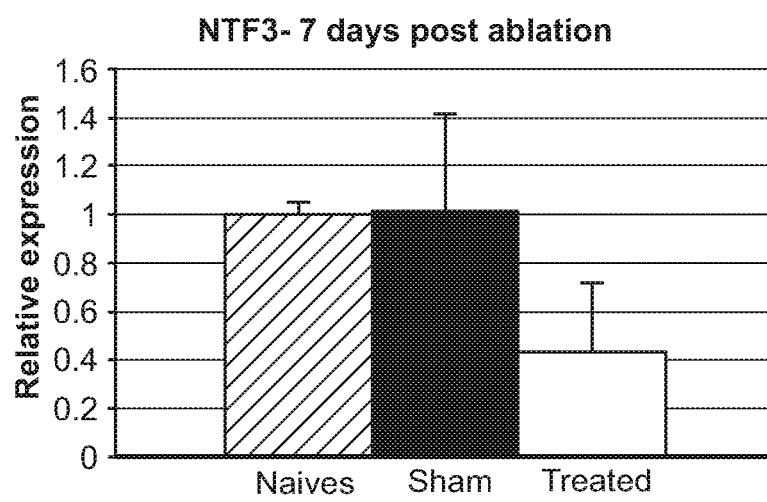
FIG. 21: Downregulation of NTF3 7 days post-ablation in endothelial cells.

| Gene (Reference) | Location | Result | Gene Product Function/Description |
|---|---|---|---|
| BNP (Paulis Nat Rev Cardiol 7: 431 (2010)) | Secreted | Upregulated 7 days post-ablation | Involved in natriuresis, diuresis, vasorelaxation, renin inhibition, and aldosterone secretion |
| FASLG (SABiosciences RT$_2$ Profiler PCR Array Human Neurotoxicity platform) | Secreted | Upregulated 7 days post-ablation | Triggers apoptosis |
| NTF3 (Frostick Microsurgery 18: 397 (1998)) | Secreted | Downregulated 7 days post-ablation (FIG. 21) | Neurotrophic growth factor, controls neuron survival and differentiation |
| ADRA2B (Kopp Hypertension 57: 640 (2011)) | Surface | Downregulated 7 days post-ablation | Involved in regulation of neurotransmitter release from sympathetic nerves and adrenergic neurons in the CNS |
| P2RY12 (Lechner Purinergic Signal 1: 31 (2004)) | Surface | Upregulated 7 days post-ablation | Diverse physiological roles including platelet aggregation, muscle contraction, and neurotransmission |
| TLR3 (Musial Pediatr Nephrol 26: 1031 (2011)) | Surface | Upregulated 7 days post-ablation | Activation of innate immunity and inflammation |
| TLR7 (Musial Pediatr Nephrol 26: 1031 (2011)) | Surface | Upregulated 7 days post-ablation | Activation of innate immunity and inflammation |
| Cyclin-dependent kinase inhibitor 2B (CDKN2B, p15) (Romanenko Diagn Mol Pathol 11: 163 (2002)) | Intracellular | Upregulated 7 days post-ablation | Potent inhibitor of cell cycle G1 progression, potent effector of TGFβ-induced cell cycle arrest |
| Cyclin-dependent kinase inhibitor 1B (CDKN1B, p27, Kip1) (Andres Cardiovasc Res 63: 11 (2004)) | Intracellular | Downregulated 7 days post-ablation | |
| Heat shock 70 kDa protein 14 (HSPA14) | Intracellular | Upregulated 7 days post-ablation | |
| Angiotensin 1 converting enzyme (ACE) (Frostick Microsurgery 18: 397 (1998); Paulis Nat Rev Cardiol 7: 431 (2010)) | Surface | | |
| Actin alpha 2 (ACTA2) (Yuan Am J Physiol Regul Integr Comp Physiol 284: R1219 (2003)) | Intracellular | | |
| Activin A receptor type IIB (ACVR2B) (Pache Am J Physiol Renal Physiol 291: F654 (2006)) | Surface | | |
| Angiotensin II receptor type 2 (AGTR2) (Paulis Nat Rev Cardiol 7: 431 (2010)) | Surface | | |
| Agouti signaling protein (ASIP) (Sonna J Appl Physiol 92: 1725 (2002)) | Secreted | | |
| Arginine vasopressin (AVP) (Paulis Nat Rev Cardiol 7: 431 (2010)) | Secreted | | |
| Arginine vasopressin receptor 2 (AVPR2) (Paulis Nat Rev Cardiol 7: 431 (2010)) | Surface | | |
| Bradykinin receptor B2 (BDKRB2) (Paulis Nat Rev Cardiol 7: 431 (2010)) | Surface | | |
| Caspase 3 apoptosis-related cysteine peptidase (CASP3) (Singdha Neurosci Bull 28: 14 (2012)) | Intracellular | | |
| Chloride intracellular channel 1 (CLIC1) (SABiosciences RT$_2$ Profiler PCR Array Human Hypertension platform) | Surface/ intracellular | | |
| Cytochrome P450 family 2 subfamily E polypeptide 1 (CYP2E1) (Wang Exp Toxicol Pathol 61: 169 (2009)) | Surface | | |
| DnaJ/Hsp40 homolog subfamily C member 3 (DNAJC3) (Sonna J Appl Physiol 92: 1725 (2002)) | Intracellular | | |

TABLE 1-continued

| Gene (Reference) | Location | Result | Gene Product Function/Description |
|---|---|---|---|
| Endothelin converting enzyme 1 (ECE1) (Ihling Curr Vasc Pharmacol 2: 249 (2004)) | Surface | | |
| Endothelin 1 (EDN1) (Paulis Nat Rev Cardiol 7: 431 (2010)) | Secreted | | |
| Endothelin receptor type A (EDNRA) (Paulis Nat Rev Cardiol 7: 431 (2010)) | Surface | | |
| Guanylate cyclase 1 soluble alpha 3 (GUCY1A3) (SABiosciences $RT_2$ Profiler PCR Array Human Hypertension platform) | Intracellular | | |
| Heat shock 70 kDa protein 6 (HSP70B) (HSPA6) (Sonna J Appl Physiol 92: 1725 (2002)) | Intracellular | | |
| Interferon (alpha, beta, and omega) receptor 1 (IFNAR1) (Bhattacharya J Biol Chem 286: 22069 (2011)) | Surface | | |
| Integrin alpha V vitronectin receptor (ITGAV) (SABiosciences $RT_2$ Profiler PCR Array Human Endothelial Cell Biology platform) | Surface | | |
| Potassium large conductance calcium-activated channel subfamily M alpha member 1 (KCNMA1) (SABiosciences $RT_2$ Profiler PCR Array Human Hypertension platform) | Surface | | |
| Kruppel-like factor 4 (KLF4) (Liu Cell Stress Chaperones 11: 379 (2006)) | Intracellular | | |
| Kininogen 1 (KNG1) (Paulis Nat Rev Cardiol 7: 431 (2010)) | Secreted | | |
| Neuropeptide Y (NPY) (Krukoff Mol Brain Res 19: 287 (1993)) | Secreted | | |
| Phenylethanolamine-N-methyltransferase noradrenalin (PNMT) (Wong Ann NY Acad Sci 1148: 249 (2008)) | Intracellular | | |
| Paraoxanase 2 (PON2) (Horke Circulation 115: 2055 (2007)) | Surface | | |
| Prostaglandin D2 synthase 21 kDa (brain) (PTGDS) (Vivekanandan-Giri Int J Proteomics 2011: 214715 (2011)) | Intracellular/ secreted | | |
| Solute carrier family 22 organic cation transporter 1-OCT1 (SLC22A1) (Zhao Cancer Res 60: 6276 (2000)) | Surface | | |
| SRA stem-loop interacting RNA binding protein (SLIRP) (Lu Curr Med Chem 17: 957 (2010)) | Intracellular | | |
| Superoxide dismutase 1, soluble (SOD1) (Sonna J Appl Physiol 92: 1725 (2002)) | Intracellular | | |
| Thrombomodulin (THBD) (SABiosciences $RT_2$ Profiler PCR Array Human Endothelial Cell Biology platform) | Surface | | |
| Transient receptor potential cation channel subfamily V member 1 (TRPV1) (Xie Hypertension 54: 1298 (2009)) | Surface | | |
| Vascular cell adhesion molecule 1 (VCAM1) (SABiosciences $RT_2$ Profiler PCR Array Human Endothelial Cell Biology platform) | Surface | | |

TABLE 1-continued

| Gene (Reference) | Location | Result | Gene Product Function/Description |
|---|---|---|---|
| Von Willebrand factor (vWF) (SABiosciences RT$_2$ Profiler PCR Array Human Endothelial Cell Biology platform) | Secreted | | |

Additional screens will be carried out using genes associated with nerves in the renal pelvis, wherein a high percentage are afferent. Examples of such genes are set forth in Table 2.

TABLE 2

| Gene (Reference) | Location |
|---|---|
| Gamma 2 actin (ACTG2) (Higgins Mol Cell Biol 15: 649 (2004)) | Intracellular |
| Caveolin 1 (Cav1) (Higgins Mol Cell Biol 15: 649 (2004)) | Surface |
| Calponin 1 (CNN1) (Higgins Mol Cell Biol 15: 649 (2004)) | Intracellular |
| Actin binding protein 280 (FLNA) (Higgins Mol Cell Biol 15: 649 (2004)) | Intracellular |
| Glutathione peroxidase 2 (GPX2) (Higgins Mol Cell Biol 15: 649 (2004)) | Intracellular |
| Myosin light polypeptide kinase (MYLK) (Higgins Mol Cell Biol 15: 649 (2004)) | |
| c-AMP protein kinase A (PRKACA) (Kopp Contrib Nephrol 172: 107 (2011)) | Intracellular |
| Prostate stem cell antigen (PSCA) (Higgins Mol Cell Biol 15: 649 (2004)) | Surface |
| Prostaglandin E$_2$ (PTGER2) (Kopp Contrib Nephrol 172: 107 (2011)) | Surface |
| EP4 receptor (PTGER4) (Kopp Contrib Nephrol 172: 107 (2011)) | Surface |
| Cyclooxygenase 2 (COX-2) (PTGS2) (Kopp Contrib Nephrol 172: 107 (2011)) | Surface |
| Tachykinin 1 precursor (TAC1) (Kopp Contrib Nephrol 172: 107 (2011)) | Secreted |
| Tachykinin receptor 1 (TACR1-NK1) (Xie Hypertension 54: 1298 (2009)) | Surface |
| TP63 (Higgins Mol Cell Biol 15: 649 (2004)) | Intracellular |
| Tropomyosin 2 (TPM2) (Higgins Mol Cell Biol 15: 649 (2004)) | |
| Uroplakin 1B (Upk1B) (Higgins Mol Cell Biol 15: 649 (2004)) | Surface |
| Upk3A (Higgins Mol Cell Biol 15: 649 (2004)) | Surface |

Screens will also be carried out using various neuronal genes that are not necessarily associated with kidney afferent nerves. Examples of such genes are set forth in Table 3.

TABLE 3

| Gene (Reference) | Location |
|---|---|
| Annexin V (ANXA5) (Luo Nat Med 5: 17 (1999)) | Intracellular |
| Calcitonin gene-related polypeptide alpha (CGRP/CALCA) (Luo Nat Med 5: 17 (1999)) | Secreted |
| Fatty acid binding protein, brain (FABP7) (Luo Nat Med 5: 17 (1999)) | Intracellular |
| Neurofilament, heavy polypeptide (NEFH) (Luo Nat Med 5: 17 (1999)) | Intracellular |
| Neurofilament, heavy polypeptide (NEFL) (Luo Nat Med 5: 17 (1999)) | Intracellular |
| Phospholipase C delta 4 (PLCD4) | Surface/ |

TABLE 3-continued

| Gene (Reference) | Location |
|---|---|
| (Luo Nat Med 5: 17 (1999)) | intracellular |
| Na N sodium voltage-gated channel (SCN11A) (Luo Nat Med 5: 17 (1999)) | Surface |
| Beta 1 subunit of voltage gated Na channels (SCN1B) (Luo Nat Med 5: 17 (1999)) | Surface |

Additional screens will be carried out using a variety of secreted, surface, and intracellular genes. Examples of genes that may be included in such screens include those set forth in Table 4.

TABLE 4

| Gene (Reference) | Location |
|---|---|
| Actinin alpha 4 (ACTN4) (Higgins Mol Biol Cell 15: 649 (2004)) | Intracellular |
| Activin A receptor type IIA (ACVR2A) (Maeshima Endocr J 55: 1 (2008)) | Surface |
| Aldolase B fructose-biphosphate (ALDOB) (Higgins Mol Biol Cell 15: 649 (2004)) | Intracellular |
| Biglycan (BGN) (Wu J Clin Invest 117: 2847 (2007)) | Secreted |
| Complement 5 (C5) (Kerr Immunobiol 217: 195 (2012)) | Secreted |
| MCP-1 (CCL2) (Darisipudi Am J Pathol 179: 116 (2011)) | Secreted |
| Chemokine (C-C motif) ligand 5 (CCL5) (Lo Transplantation 91: 70 (2011)) | Secreted |
| Chemokine (C-C motif) receptor 1 (CCR1) (Dikow Transplantation 90: 771 (2010)) | Surface |
| Ciliary neurotrophic factor (CNTF) (Ransom Kidney Int 67: 1275 (2005)) | Intracellular |
| Collagen type 1 alpha 1 (Col1A1) (Reich J Mol Diagn 13: 143 (2011)) | Secreted |
| Collagen type 1 alpha 2 (Col1A2) (Fragiadaki Matrix Biol 30: 396 (2011)) | Secreted |
| Collagen type 5 alpha 2 (Col5A2) (Liu Hypertension 55: 974 (2010)) | Secreted |
| C reactive protein (CRP) (Trimarchi Int J Nephrol Renovasc Dis 5: 1 (2012)) | Secreted |
| Connective tissue growth factor (CTGF/CNN2) (Lan Clin Exp Pharmacol Physiol (epub Dec. 28, 2011)) | Secreted |
| Cathepsin B (CTSB) (Todorov Kidney Blood Press Res 24: 75 (2001)) | Intracellular |
| Cubilin (CUBN) (Amsellem J Am Soc Nephrol 21: 1859 (2010)) | Surface |
| CXCL5 (Maity Cytokine 54: 61 (2011)) | Secreted |
| Tissue factor (LOC396677) (F3) (Kourtzelis Blood 116: 631 (2010)) | Surface |
| Fibrillin 1 (FBN1) (Gaikwad Biochem J 432: 333 (2010)) | Secreted |
| Ficolin (collagen/fibrinogen domain containing) 3 (FCN3) (Higgins Mol Biol Cell 15: 649 (2004)) | Secreted |
| Fibroblast growth factor receptor 2 (FGFR2) (Ford Kidney Int 51: 1729 (1997)) | Secreted/ surface |
| Fibromodulin (FMOD) (Lee J Biol Chem 286: 6414 (2011)) | Secreted |
| Fibronectin (FN1) (Waalkes BMC Cancer 10: 503 (2010)) | Secreted |

TABLE 4-continued

| Gene (Reference) | Location |
|---|---|
| Fucosyltransferase 6 (FUT6) (Higgins Mol Biol Cell 15: 649 (2004)) | Intracellular |
| Glial cell line-derived neurotrophic factor (GDNF) (Saito Hum Pathol 42: 848 (2011)) | Secreted |
| Cybb, NOX2 (Gp91-phox) (Kinoshita Transl Res 158: 235 (2011)) | Surface |
| Glutathione S-transferase A2 (GSTA2) (Leonard FASEB J 20: 2624 (2006)) | Intracellular |
| GST Yb-1 protein (GSTM1-1) (Abruzzo Free Radic Res 44: 563 (2010)) | Intracellular |
| Glutathione S-transferase mu 2 (GSTM2-LOC780435) (Yuan Am J Physiol Regul Integr Comp 284: R1219 (2003)) | Intracellular |
| Glutathione S-transferase alpha (GSTA1) (GST-α) (Obeidat Nephrol Dial Transplant 26: 3038 (2011)) | Intracellular |
| Isocitrate dehydrogenase 3 NAD beta (IDH3B) (Dange J Biol Chem 285: 20520 (2010)) | Intracellular |
| Interleukin 1b (IL1b) (Grishman Pediatr Res (epub Feb. 15, 2012)) | Secreted |
| Interleukin 6 (IL-6) (Zhang Hypertension 59: 136 (2012)) | Secreted |
| CXCL8 (IL8) (Maity Cytokine 54: 61 (2011)) | Secreted |
| Inducible nitric oxide synthase (iNOS (NOS2)) (Ma Am J Physiol Renal Physiol 300: F1410 (2011)) | Intracellular |
| Ketohexokinase (fructokinase) (KHK) (Higgins Mol Biol Cell 15: 649 (2004)) | Intracellular |
| Lamini beta 1 (LAMB1) (Sataranatarajan Am J Pathol 171: 1733 (2007)) | Secreted |
| Lipocalin 2 (NGAL) (LCN) (Zerega Eur J Cell Biol 79: 165 (2000)) | Secreted |
| Maltase-glucoamylase (MGAM) (Higgins Mol Biol Cell 15: 649 (2004)) | Surface |
| Matrix metallopeptidase 2 (MMP2) (Mazanowska Transplant Proc 43: 3000 (2011)) | Secreted |
| Matrix metallopeptidase 9 (MMP9) (Begatta J Am Soc Nephrol 20: 787 (2009)) | Secreted |
| Metallothionein (MT1A) (Klosterhalfen Biochem Pharmacol 52: 1201(1996)) | Intracellular |
| Neuronal nitric oxide synthase 1 (nNOS (NOS1)) (Zheng Am J Physiol Heart Circ Physiol 301: H2402 (2011)) | Surface |
| Prostaglandin E synthase 2 (PTGES2) (Kopp Hypertension 57: 640 (2011)) | Surface |
| Prostaglandin endoperoxide synthase 1 (COX-1) (PTGS1) (Liu Am J Physiol Renal Physiol (epub Feb. 1, 2012)) | Intracellular |
| Replication protein A1 (RPA-1) (Liu Mol Cell Biol 31: 4298 (2011)) | Intracellular |
| Replication protein A2 (RPA-2) (Nakaya J Biochem 148: 539 (2010)) | Intracellular |
| Shingosine-1-phosphate receptor 1 (S1PR1/EDG1) (Higgins Mol Biol Cell 15: 649 (2004)) | Surface |
| Serpin peptidase inhibitor clade F (SerpinF1) (Sigdel Proteomics Clin Appl 4: 32 (2010)) | Secreted |
| Secreted acidic cystein-rich glycoprotein (osteonectin) (SPARC) (Lloyd-Burton J Comp Neurol (epub Dec. 15, 2011)) | Secreted |
| Transforming growth factor beta 1 (TGFB1) (Lantero Mol Neurobiol 45: 76 (2012)) | Secreted |
| Transforming growth factor beta 2 (TGFB2) (Lantero Mol Neurobiol 45: 76 (2012)) | Secreted |
| Tyrosine hydroxylase (TH) (Rothmond Anat Embryol (Berl) 209: 41 (2004)) | Intracellular |
| Thrombospondin 1 (THBS1) (Sun Kidney Blood Press Res 35: 35 (2012)) | Intracellular |
| Tight junction protein (TJP1 (ZO-1)) (Higgins Mol Biol Cell 15: 649 (2004)) | Surface |
| Thioredoxin (TXN) (Kasuno Rinsho Byori 59: 189 (2011)) | Intracellular/secreted |
| Vascular endothelial growth factor A (VEGFA) (Chade F1000 Med Rep (epub Jan. 3, 2012)) | Secreted |
| SMAD family member 6 (SMAD6 (MADH6)) (Higgins Mol Biol Cell 15: 649 (2004)) | Intracellular |
| Galanin prepropeptide (GAL) (Longley Neuroscience 55: 253 (1993)) | Secreted |
| Nephrin (NPHS1) (Ruotsalainen Proc Natl Acad Sci USA 96: 7962 (1999)) | Surface |

Additional screens may be carried out to evaluate changes in various non-protein candidate biomarkers such as NE, DBN, or other catecholamines in renal tissue.

Example 2: In Vitro Target Biomarker Screening (Human)

Additional candidate target biomarkers were evaluated through in vitro screening of human vascular and neuronal cells. Target biomarkers were identified based on changes in expression and/or secretion levels in response to experimental conditions that imitate heat-based stress to neuronal and vascular cells, thereby mimicking in vivo intervention. Specifically, cells were exposed to inflammatory stimulation and/or heat to simulate arterial RF ablation and SNS denervation in vivo.

Figure 22:
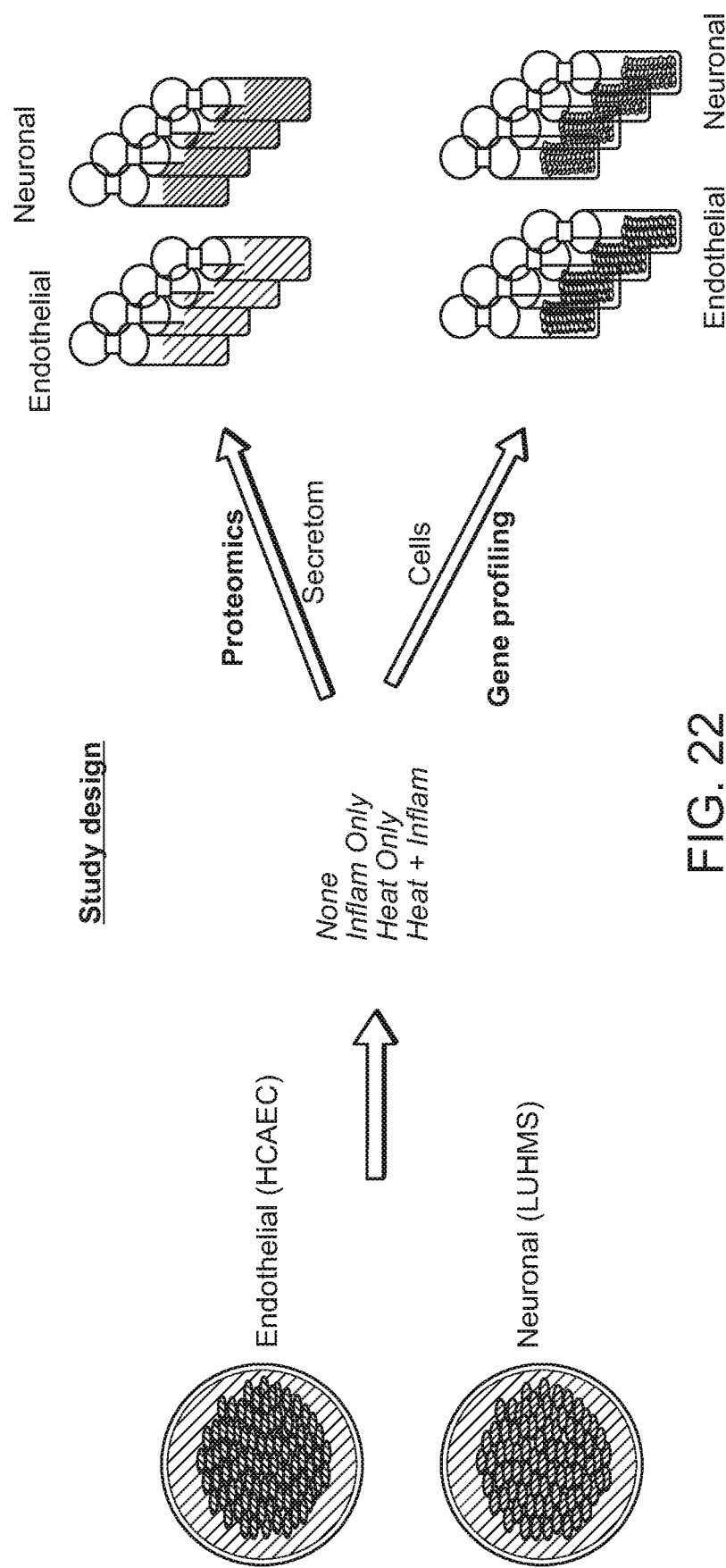
FIG. 22: General protocol for human in vitro gene expression/secretomics experiment.
Figure 23:
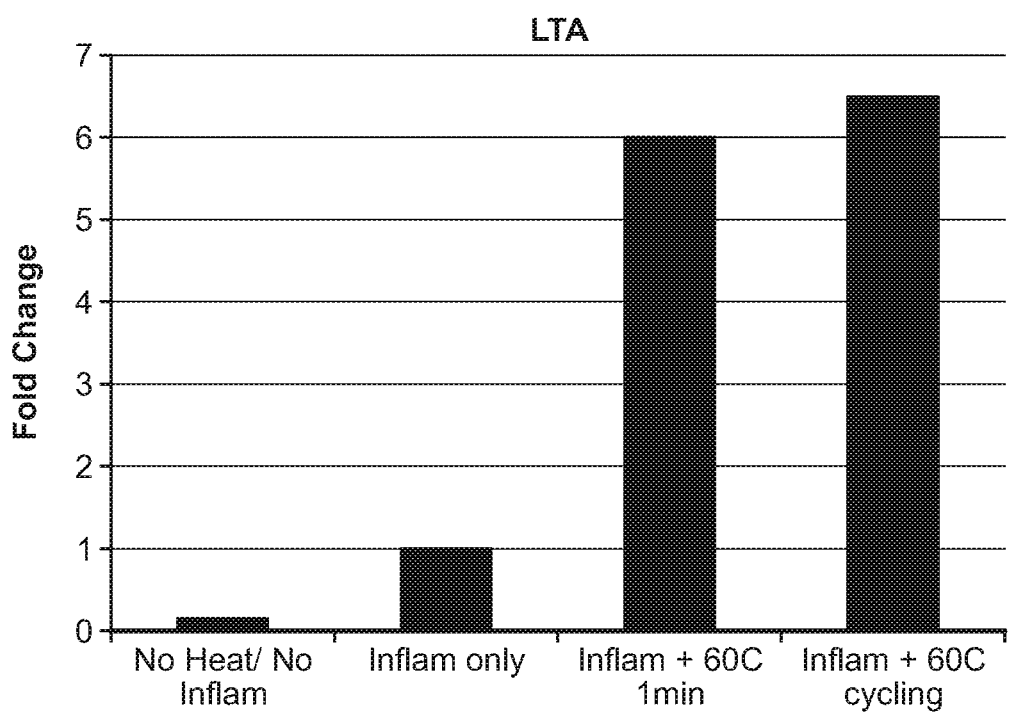
FIG. 23: Upregulation of LTA in response to inflammation/heat in endothelial cells.
Figure 24:
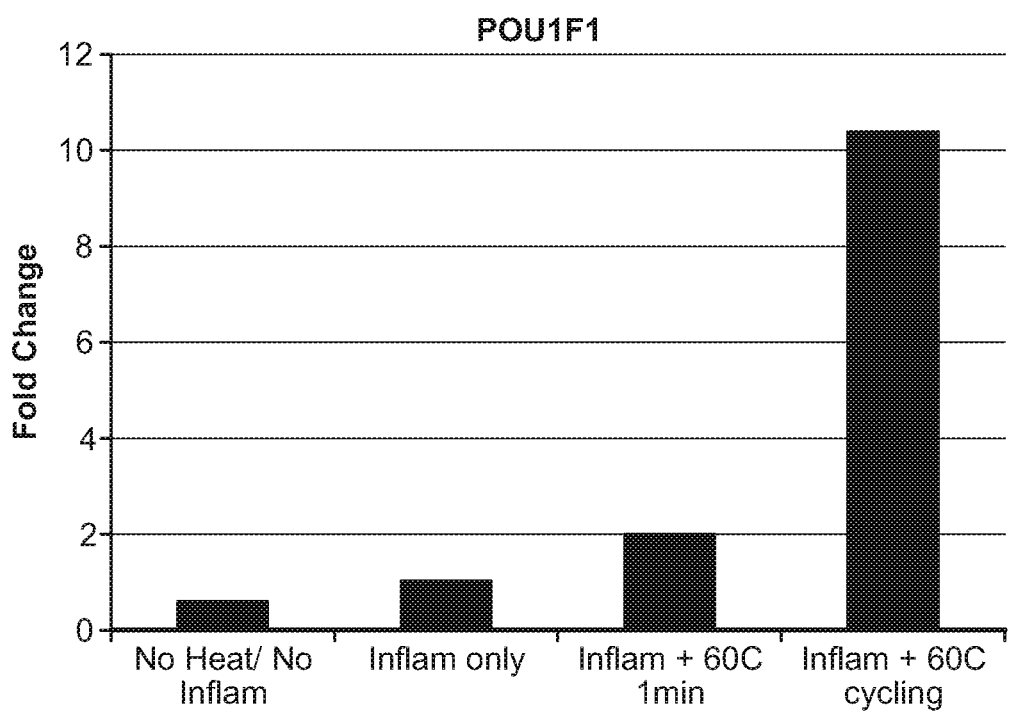
FIG. 24: Upregulation of POU1F1 in response to inflammation/heat in endothelial cells.
Figure 25:
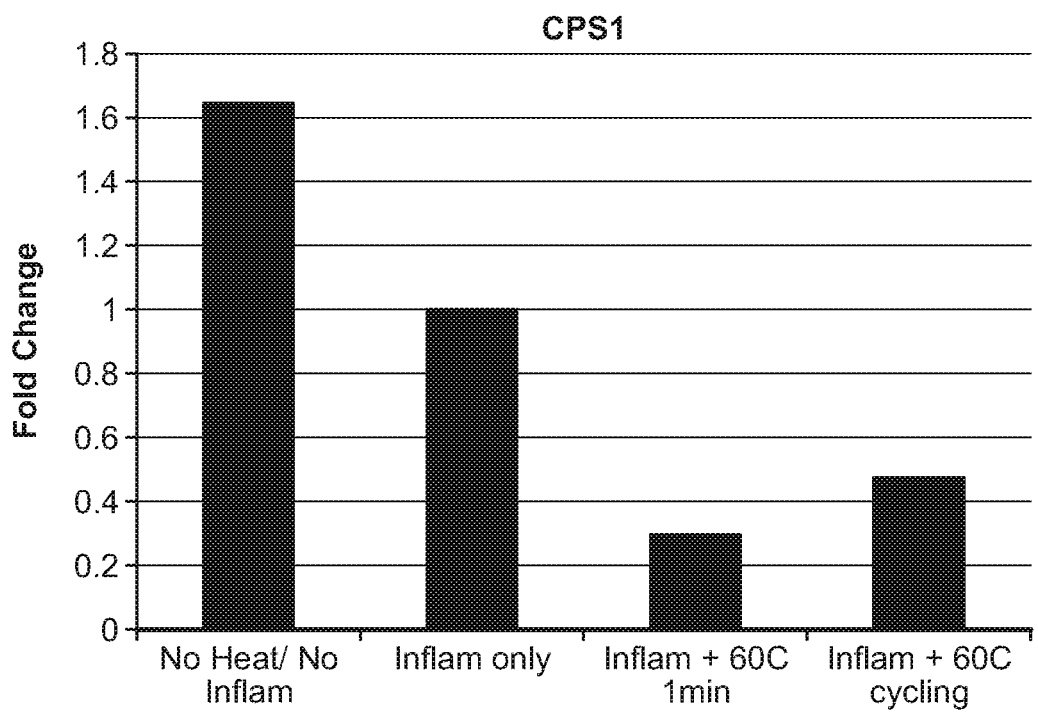
FIG. 25: Upregulation of CPS1 in response to inflammation/heat in endothelial cells.
Figure 26:
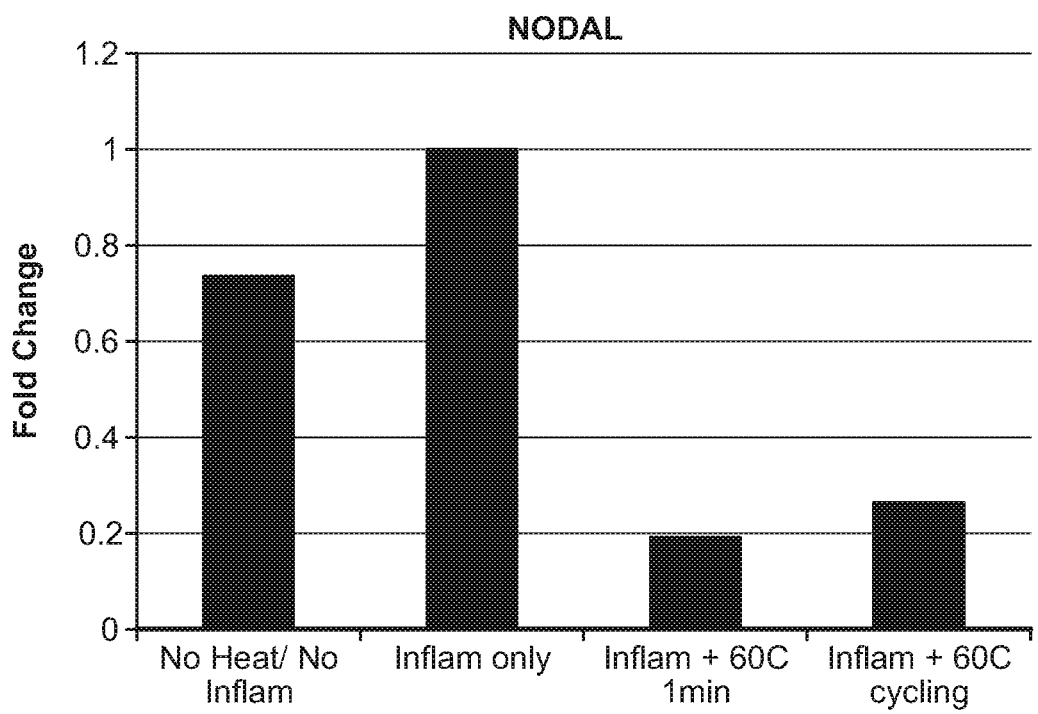
FIG. 26: Upregulation of NODAL in response to inflammation/heat.
Figure 27:
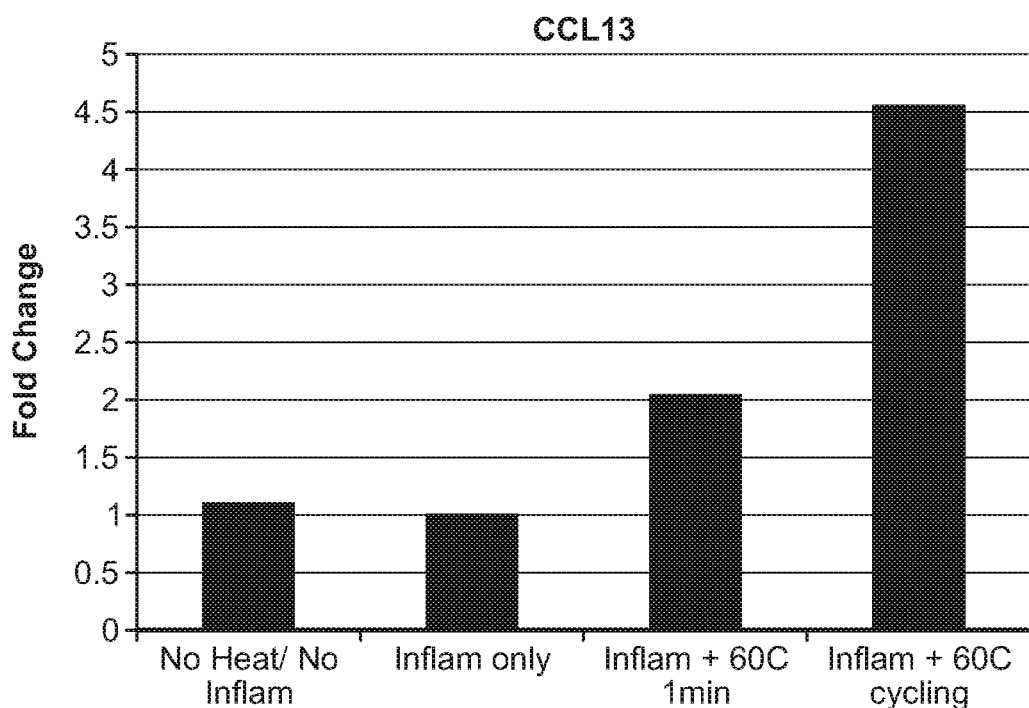
FIG. 27: Upregulation of CCL13 in response to inflammation/heat in endothelial cells.
Figure 28:
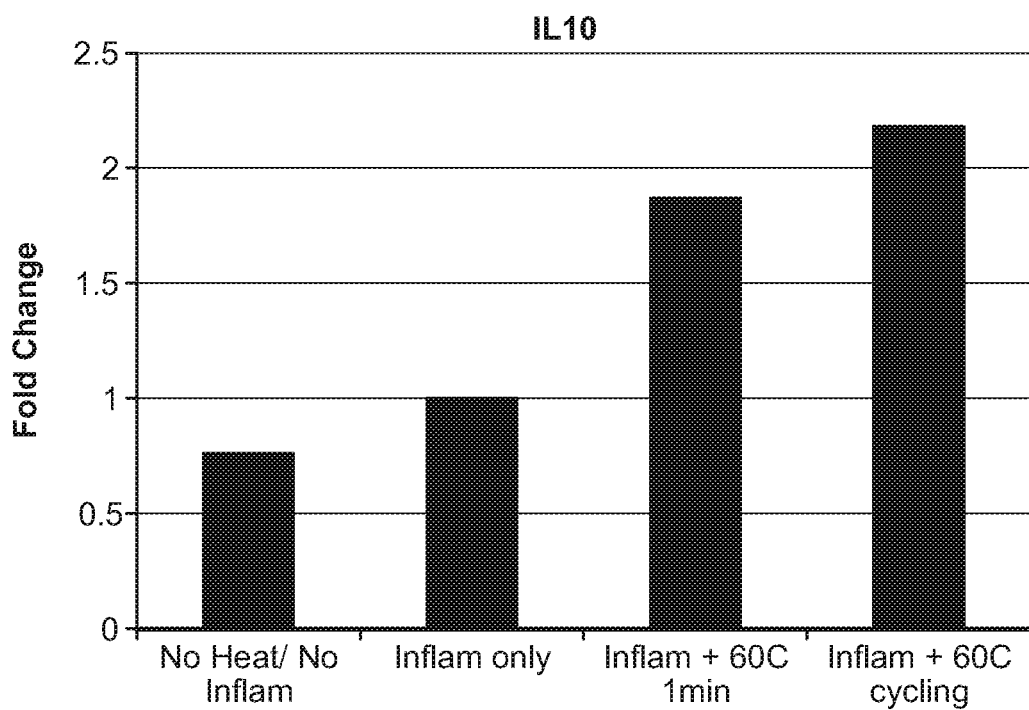
FIG. 28: Upregulation of IL-10 in response to inflammation/heat in endothelial cells.

A first set of gene profiling and secretomics experiments were performed according to the protocol set forth in FIG. 22. In this first set of experiments, Human Coronary Artery Endothelial Cells (HCAEC), Human Coronary Artery Smooth Muscle Cells (HCASMC), and Lund human mesencephalic cells (LUHMES) were exposed to inflammatory conditions and/or heat, following by secretomic and gene profiling studies. Inflammatory conditions were obtained by treating cultured cells with various inflammatory cytokines (e.g., TNFα or IL-1β at about 5 ng/ml) to mimic the cellular environment during neuromodulatory intervention. Cells exposed to heat were subjected to an elevated temperature of 60° C. for 90 seconds and allowed to recover at 37° C. for various time periods (e.g., 30-120 seconds). Cell culture samples were obtained for proteomics analysis prior to inflammation/heat exposure and at 1, 5, and 10 minutes post-exposure.

Cells were lysed, and gene profiling was performed. This resulted in the identification of 19 proteins that exhibited an acute response to inflammation and heat. These proteins are listed in Table 5. Results for LTA, POU1F1, CPS1, NODAL, CCL13, and IL-10 are set forth in FIGS. 23-28, respectively.

TABLE 5

| Gene | Gene Product Function/Description |
|---|---|
| CASP10 | Cysteinyl aspartate protease involved in signal transduction pathways of apoptosis, necrosis, and inflammation |
| CCL13 (MCP4) | Chemotactic factor that attracts monocytes, lymphocytes, basophils, and eosinophils, but not neutrophils |
| CCND1 | Regulatory component of cyclin D1-CDK4 (DC) complex that phosphorylates and inhibits members of the retinoblastoma (RB) protein family and regulates cell cycle during G(1)/S transition |
| CD70 | Cytokine that binds CD27, plays role in T-cell activation, induces proliferation of co-stimulated T-cells and enhances generation of cytolytic T-cells |
| CPS1 | Mitochondrial enzyme catalyzes synthesis of carbamoyl phosphate from ammonia and bicarbonate, involved in urea cycle of ureotelic animals, plays important role in removing excess urea |

TABLE 5-continued

| Gene | Gene Product Function/Description |
|---|---|
| CRYAB | Members of small heat shock protein (sHSP) family, acts as molecular chaperone by holding proteins in large soluble aggregates, elevated expression in many neurological diseases |
| DNAJB1 | Interacts with Hsp70, stimulates ATPase activity |
| DNAJB11 | |
| HSPA1A | |
| HSPA1B | |
| HSPB6 | Expressed in multiple tissues, most highly constitutively expressed in different types of muscle including vascular, airway, colonic, bladder, uterine smooth muscle, cardiac muscle, and skeletal muscle, has specific functions for vasodilation, platelet function, and insulin resistance in smooth and cardiac muscle |
| IL-10 | Anti-inflammatory cytokine with pleiotropic effects in immunoregulation and inflammation, inhibits synthesis of various cytokines including IFN-γ, IL-2, IL-3, TNF, and GM-CSF produced by activated macrophages and helper T-cells |
| KIT | Receptor for stem cell factor (mast cell growth factor), has tyrosine-protein kinase activity, ligand binding leads to autophosphorylation and associate with substrates such as phosphatidylinositol 3-kinase (Pi3K) |
| LTA | Member of TNF family produced by lymphocytes, highly inducible, forms heterotrimers with lymphotoxin beta |
| MYLK3 | Myosin light chain kinases (MLCKs) are serine/threonine kinases divided into two subtypes, MLCK1 subtype is found in smooth muscle and phosphorylates myosin II regulatory light chains at Ser19 |
| NODAL | Member of TGF-β superfamily, may be essential for mesoderm formation and subsequent organization of axial structures in early embryonic development |
| NPY1R | NPY receptors are Gi/o-protein-coupled receptors divided into four subtypes (Y1, Y2, Y4, Y5), mediate diverse range of biological actions including stimulation of food intake and anxiolysis |
| POU1F1 | Member of TNF ligand family, part of POU family of transcription factors that regulate mammalian development |
| TCP1 | Molecular chaperone, assists folding of proteins upon ATP hydrolysis, may play a role in formation of BBSome (complex involved in ciliogenesis), plays a role in actin and tubulin folding |

Figure 29:
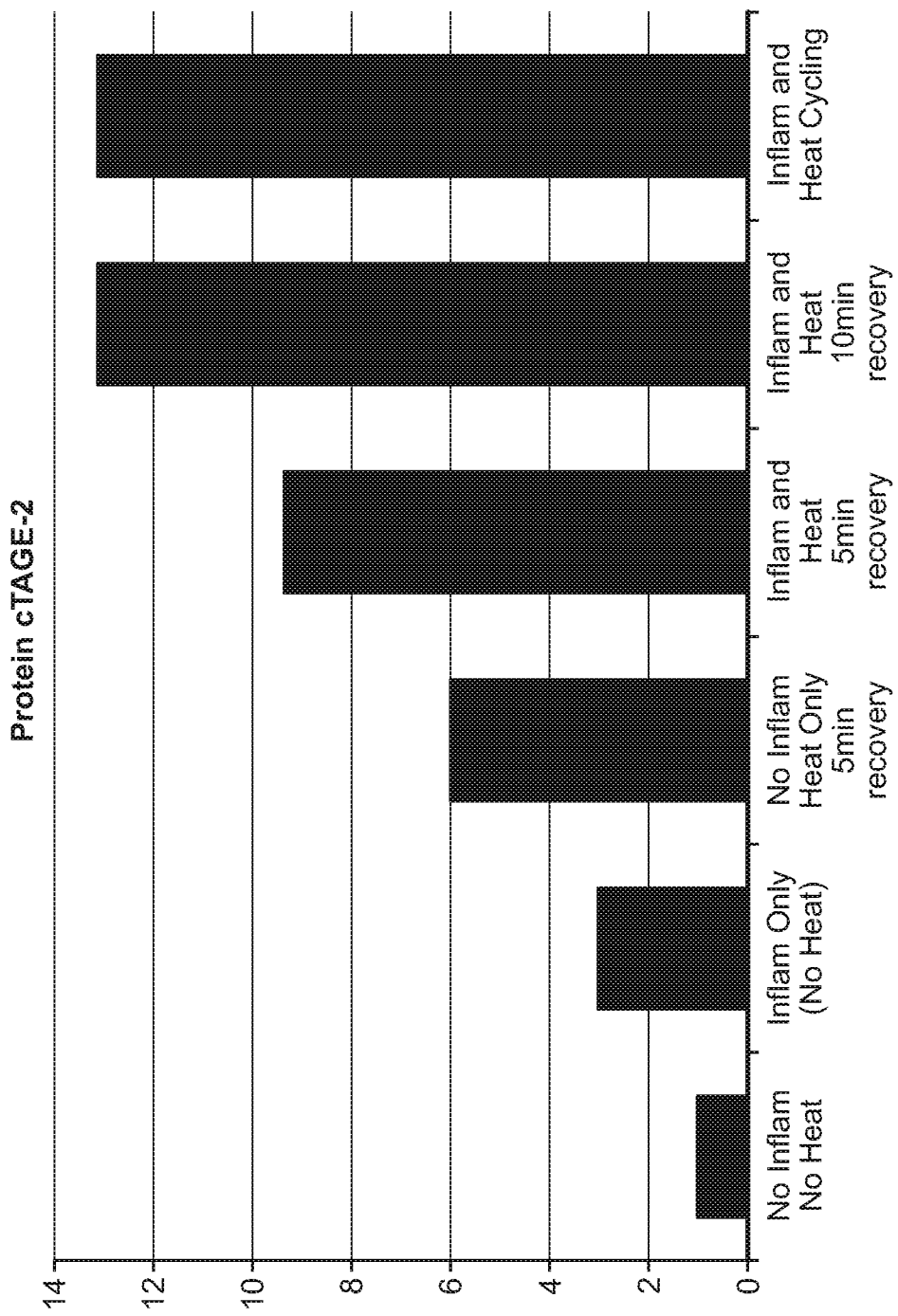
FIG. 29: Increased secretion of cTAGE-2 in response to inflammation/heat in endothelial cells.

The collected cell culture samples included cultured media from the treated cells (i.e., conditioned media) into which the cells can actively secrete proteins, peptides, and non-protein molecules in response to inflammation and heat. These cell culture samples were subjected to secretomics to identify proteins released into culture in response to inflammation and heat. Secretomics assays were performed using iTRAQ methodology (Wiśniewski Arch Pathol Lab Med 132:1566 (2008)). Samples were diluted, digested with trypsin, and iTRAQ labeled using 8-Plex reagent. The resultant complex protein digests were pooled together for MudPIT analysis. Each fraction was analyzed by LC-MS/MS, for acquisition of mass spectroscopy data with the inclusion of iTRAQ quantitation data. The 13 proteins listed in Table 6 exhibited increased secretion after exposure to inflammatory markers and heat. Results for cTAGE-2 are set forth in FIG. 29.

TABLE 6

| Protein | Gene | Function/Description |
|---|---|---|
| Actin, cytoplasmic | ACTA2 | Major component of cytoskeletal part of contractile apparatus |
| S100 calcium binding protein A6 | CACY/2A9 | May function as calcium sensor and contribute to cellular calcium signaling, may function by interacting with other proteins and indirectly play a role in reorganization of the actin cytoskeleton and in cell motility |
| Cofilin-1 | CFL1 | Actin de-polymerization factor |
| Protein cTAGE-2 | CTAG1A1/CTAG21 | Antigen overexpressed in many cancers, but also expressed in normal testis, potential role in survival/stress response |
| L-lactate dehydrogenase A | LDHA | Catalyzes conversion of L-lactate and NAD to pyruvate and NADH in final step of aerobic glycolysis |
| Transmembrane protein 141 | MGC141/TMEM141 | Multi-pass membrane protein |
| N-alpha-acetyltransferase 20 | NAA20/NAT5 | Catalytic subunit of NatB complex which catalyzes acetylation of N-terminal methionine residue of peptides beginning with Met-Asp-Glu, may play a role in normal cell cycle progression |
| Nucleoside diphosphate kinase B | NM23B | Major role in synthesis of nucleoside triphosphates other than ATP, acts as transcriptional activator of MYC gene, binds DNA non-specifically, exhibits histidine protein kinase activity |
| Phytanoyl-CoA deoxygenase, peroxisomal | PAHX/PHYH1 | Plays role in lipid metabolism |
| Prefoldin subunit 1 | PFDN1 | |
| Serine/threonine-protein kinase PLK2 | PLK-2 | Plays key role in synaptic plasticity and memory by regulating Ras and Rap protein signaling, induction by p53/TP53 suggests it may participate in mitotic checkpoint following stress, activated by phosphorylation of Thr-239 |
| Tubulin alpha-1B chain | TUBA1B | Part of microtubule, function in maintaining cell shape |
| Vimentin | VIM | Class-III intermediate filament found in various non-epithelial cells (especially mesenchymal cells), attached to the nucleus, endoplasmic reticulum, and mitochondria, either laterally or terminally involved with LARPS in stabilization of type I collagen mRNAs for CO1A1 and CO1A2 |

Cell culture samples were further subjected to proteomics analysis using commercially available ELISA assays for proteins encoded by the genes identified in Tables 5 and 6.

Figure 30:
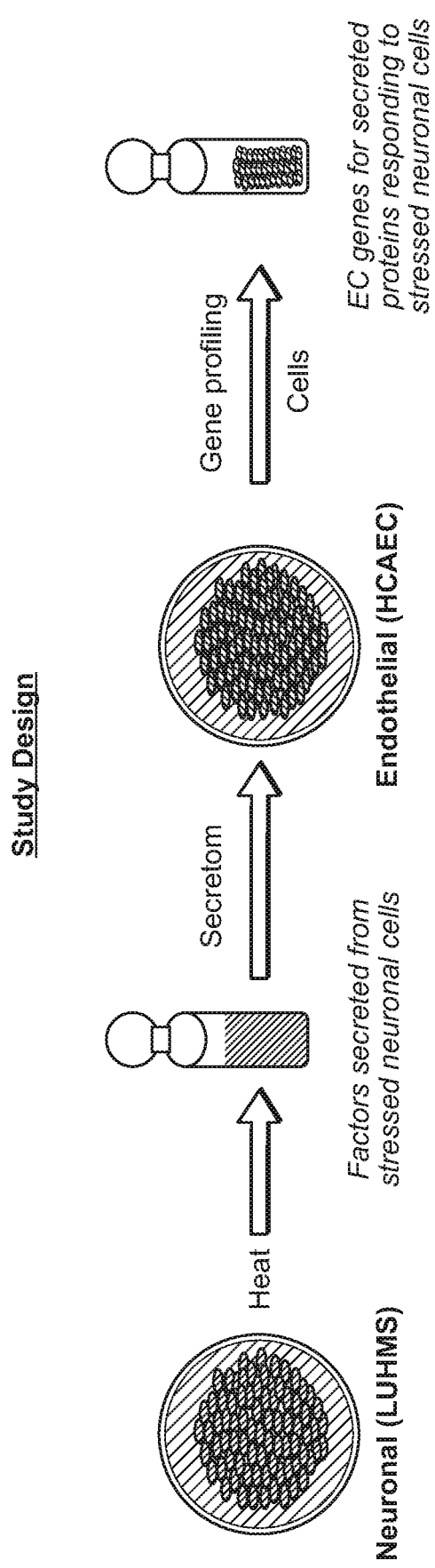
FIG. 30: General protocol for human in vitro gene expression/secretomics experiment.
Figure 31A:
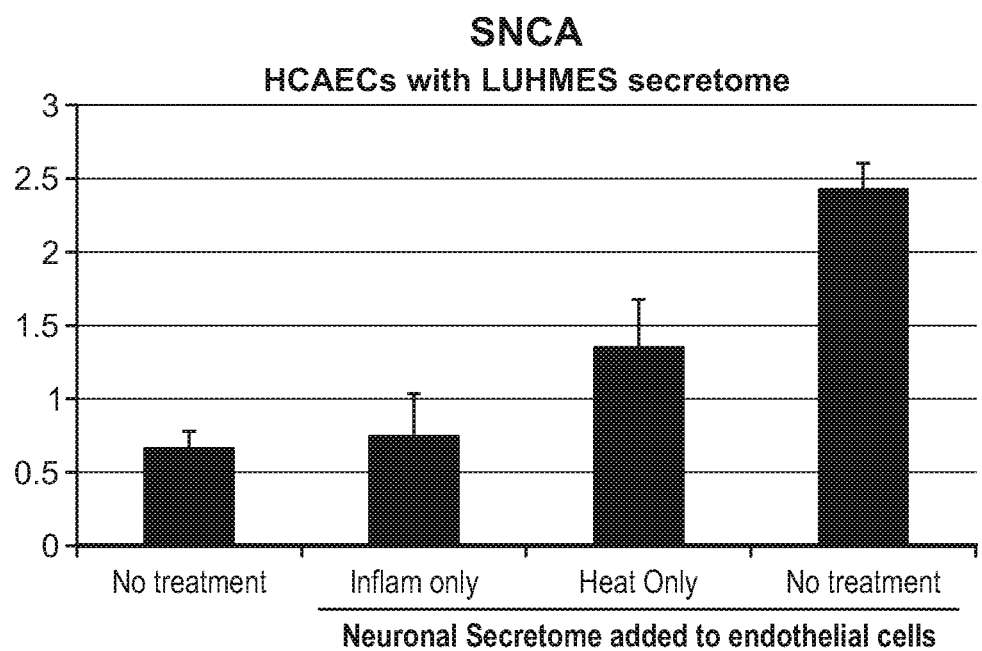
FIGS. 31A-B: Upregulation of SNCA expression by HCAECs in the presence of (A) secreted proteins from LUHMES treated with inflammation/heat and (B) added neuronal (recombinant) factor BDNF.
Figure 31B:
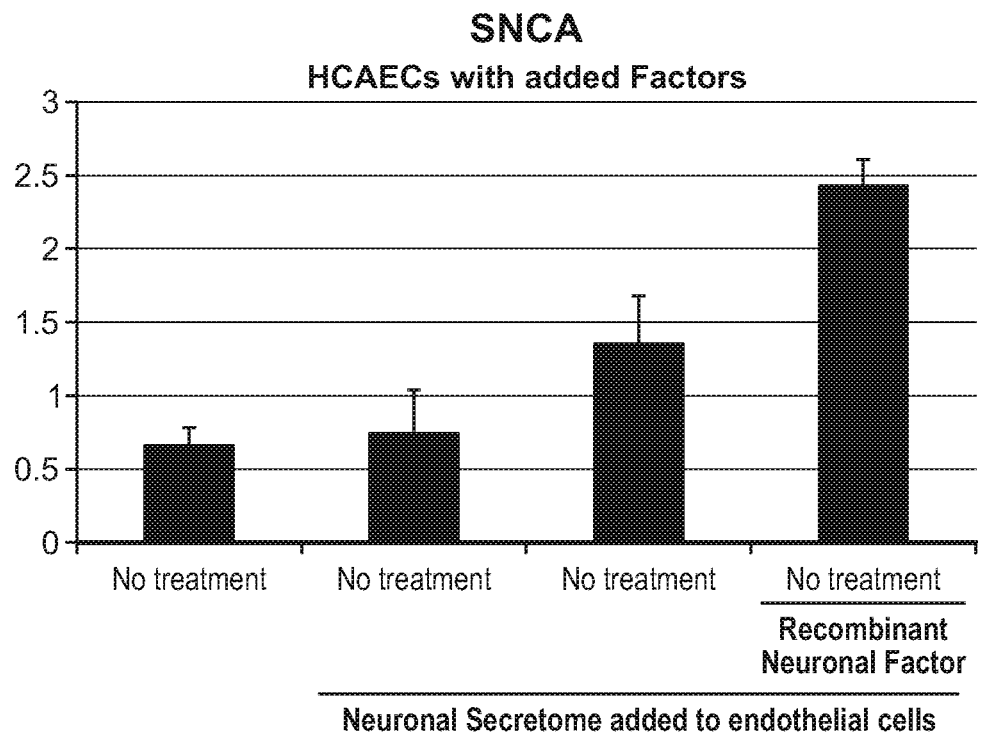
Figure 32:
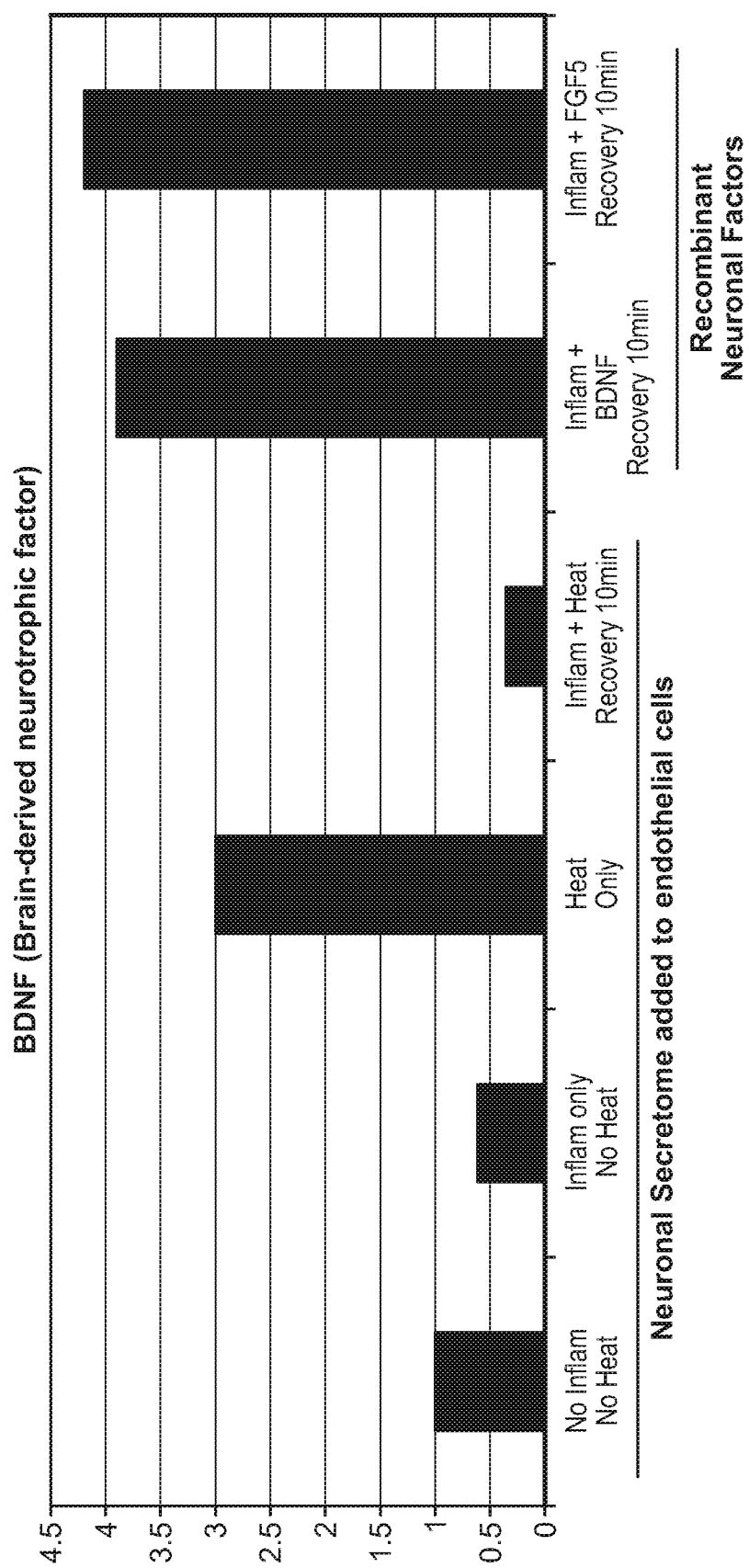
FIG. 32: Upregulation of BDNF expression in response to heat and/or inflammation in neuronal cells treated with inflammation/heat and with added neuronal (recombinant) factors BDNF or FGF5.
Figure 33:
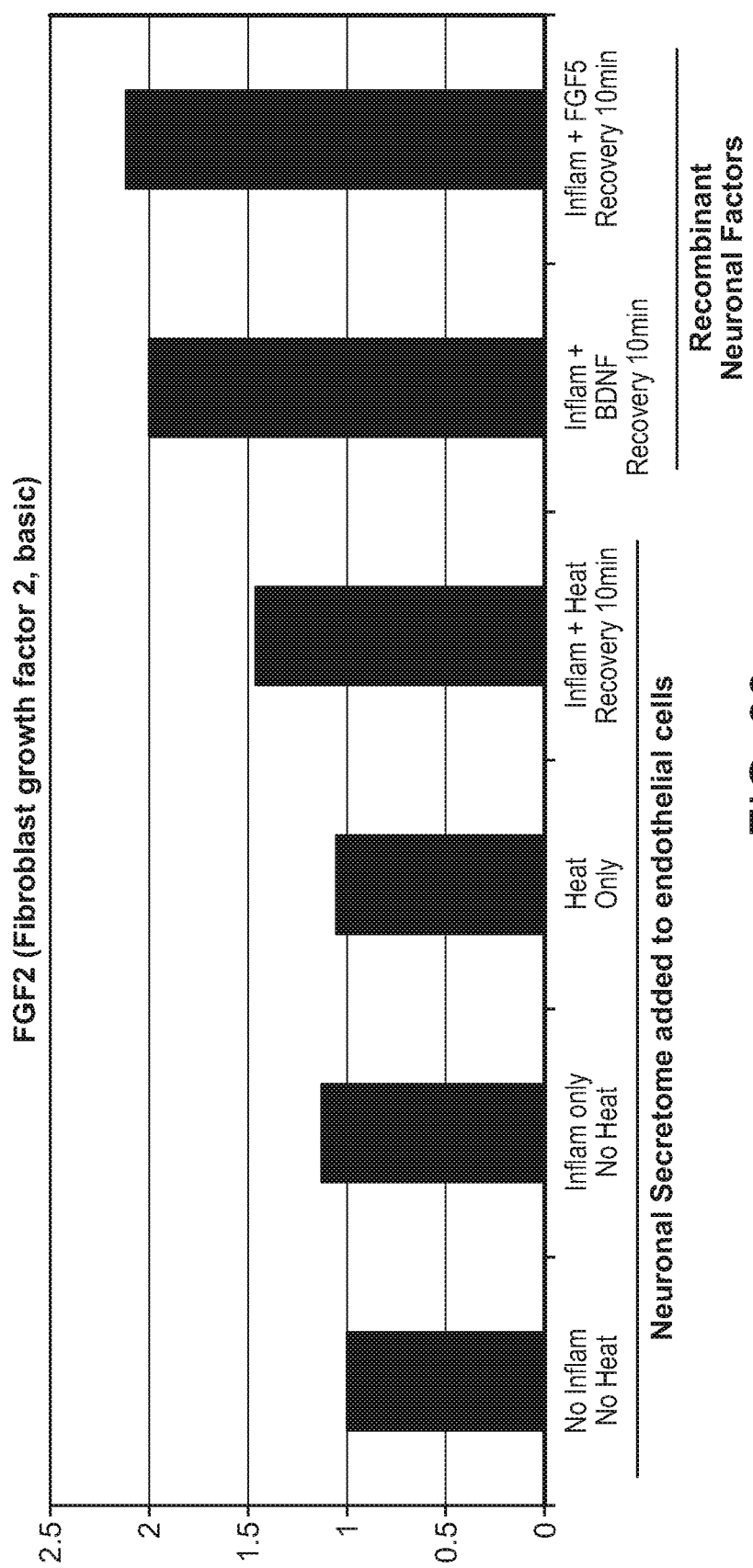
FIG. 33: Upregulation of FGF2 expression in response to heat and/or inflammation and with added neuronal (recombinant) factors BDNF or FGF5.
Figure 34:
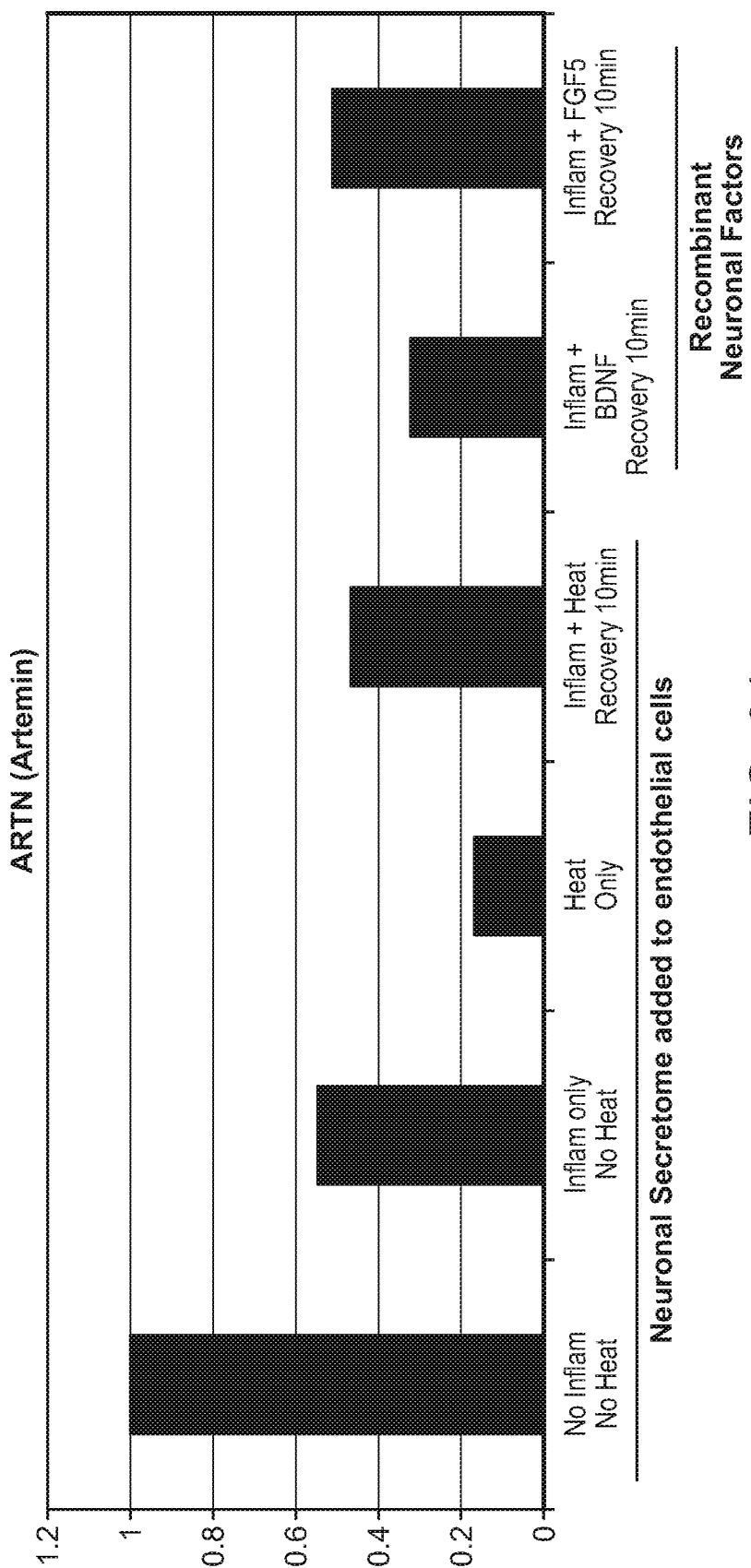
FIG. 34: Upregulation of ARTN expression in response to heat and/or inflammation and with added neuronal (recombinant) factors BDNF or FGF5.
Figure 35:
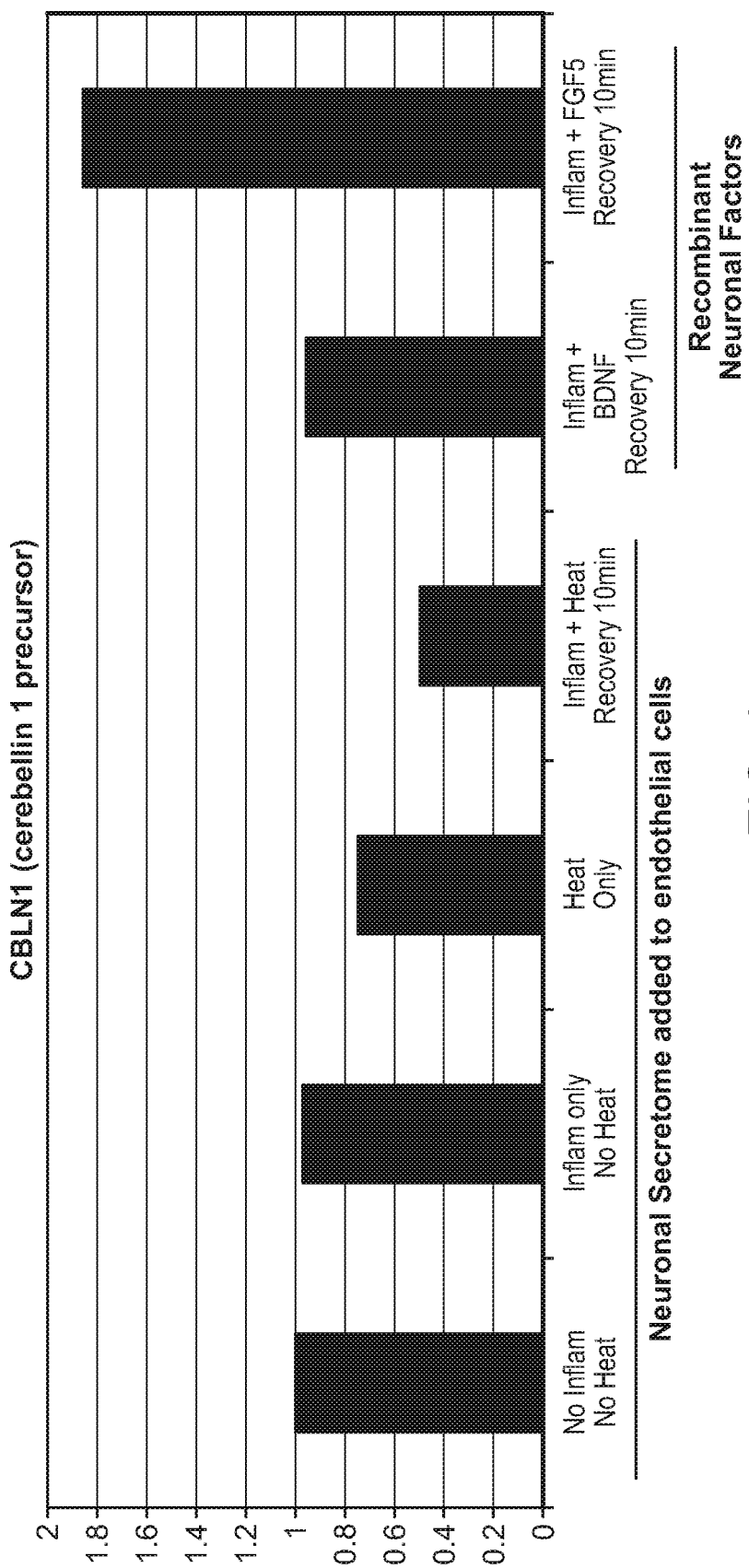
FIG. 35: Upregulation of CBLN1 expression in response to heat and/or inflammation and with added neuronal (recombinant) factors BDNF or FGF5.
Figure 36:
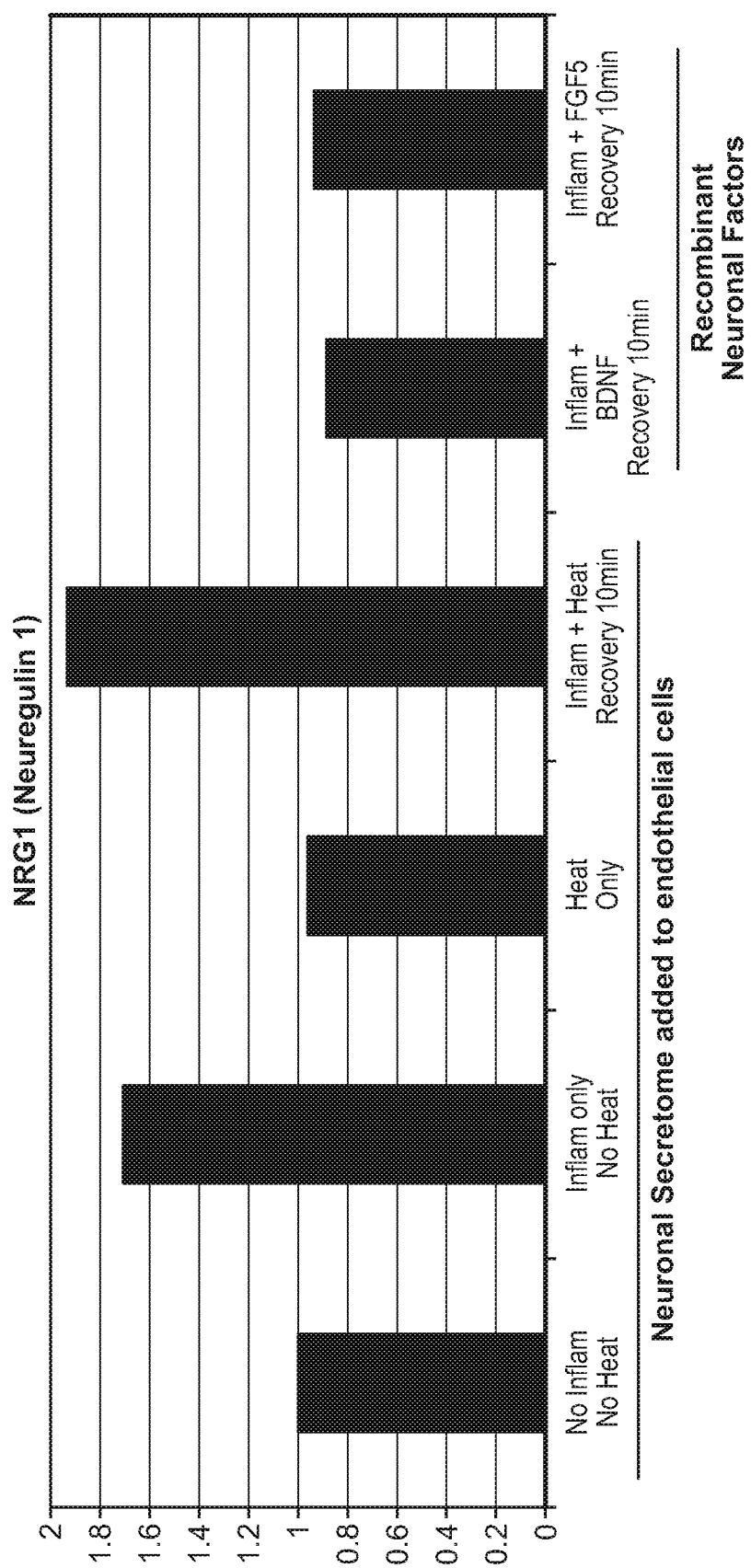
FIG. 36: Upregulation of NRG1 expression in response to heat and/or inflammation and with added neuronal (recombinant) factors BDNF or FGF5.
Figure 37:
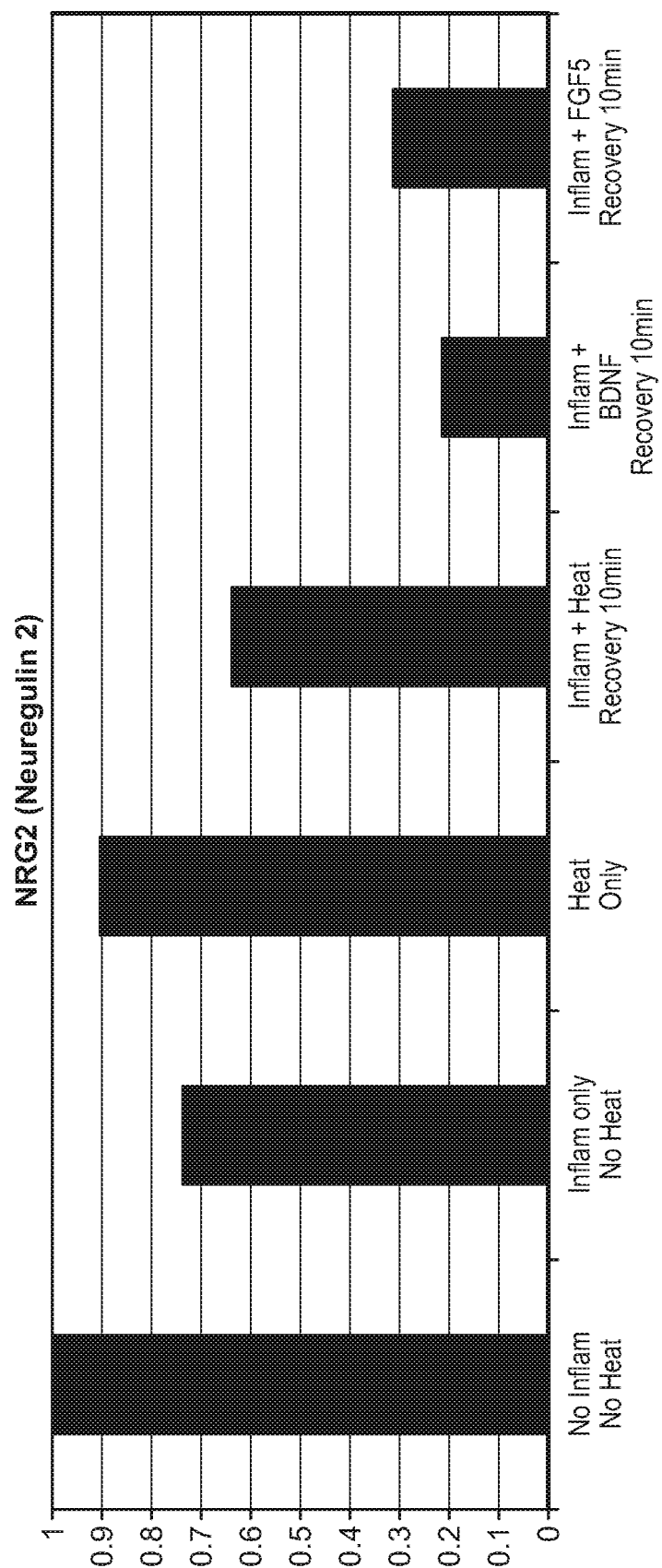
FIG. 37: Upregulation of NRG2 expression in response to heat and/or inflammation and with added neuronal (recombinant) factors BDNF or FGF5.
Figure 38:
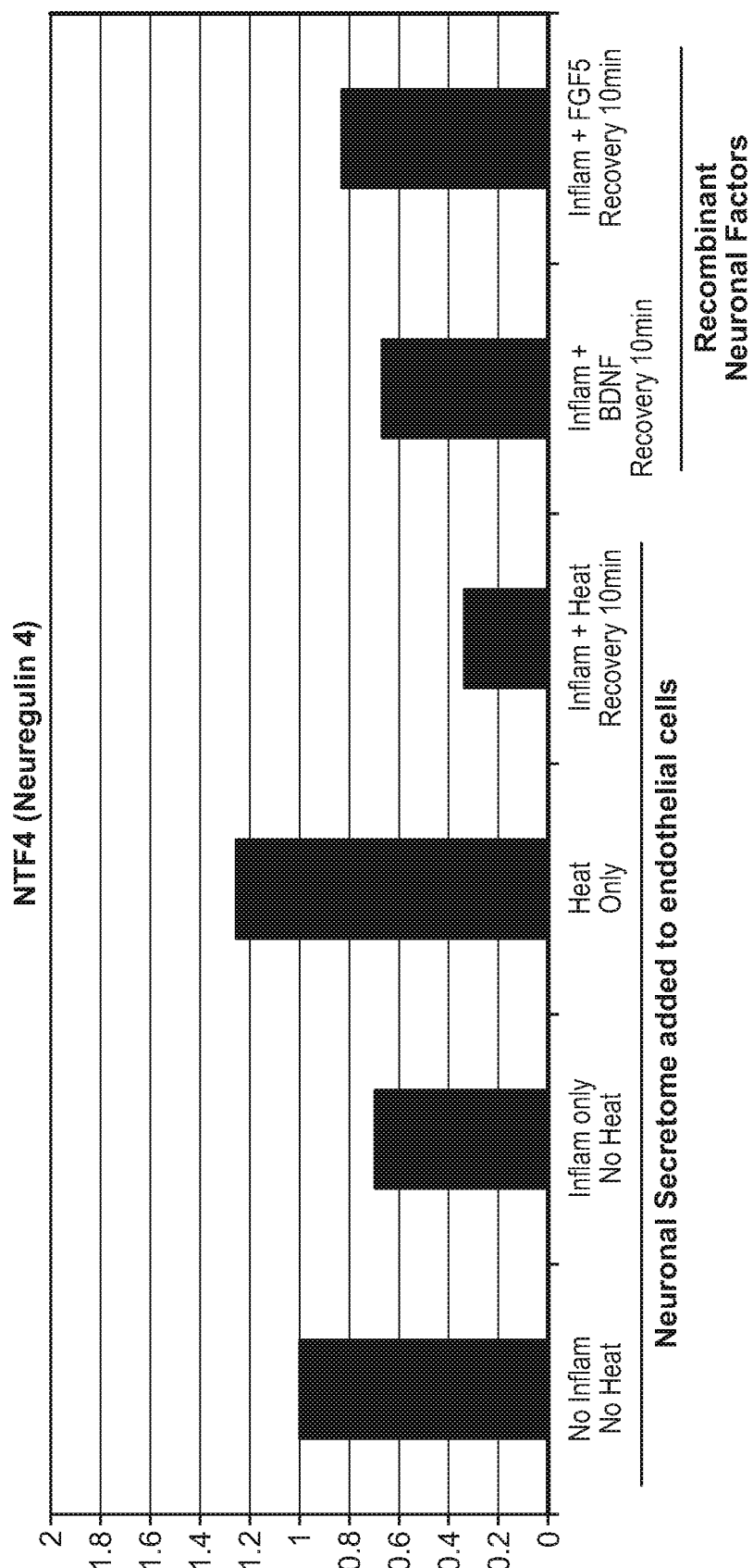
FIG. 38: Upregulation of NRG4 expression in response to heat and/or inflammation and with added neuronal (recombinant) factors BDNF or FGF5.
Figure 39:
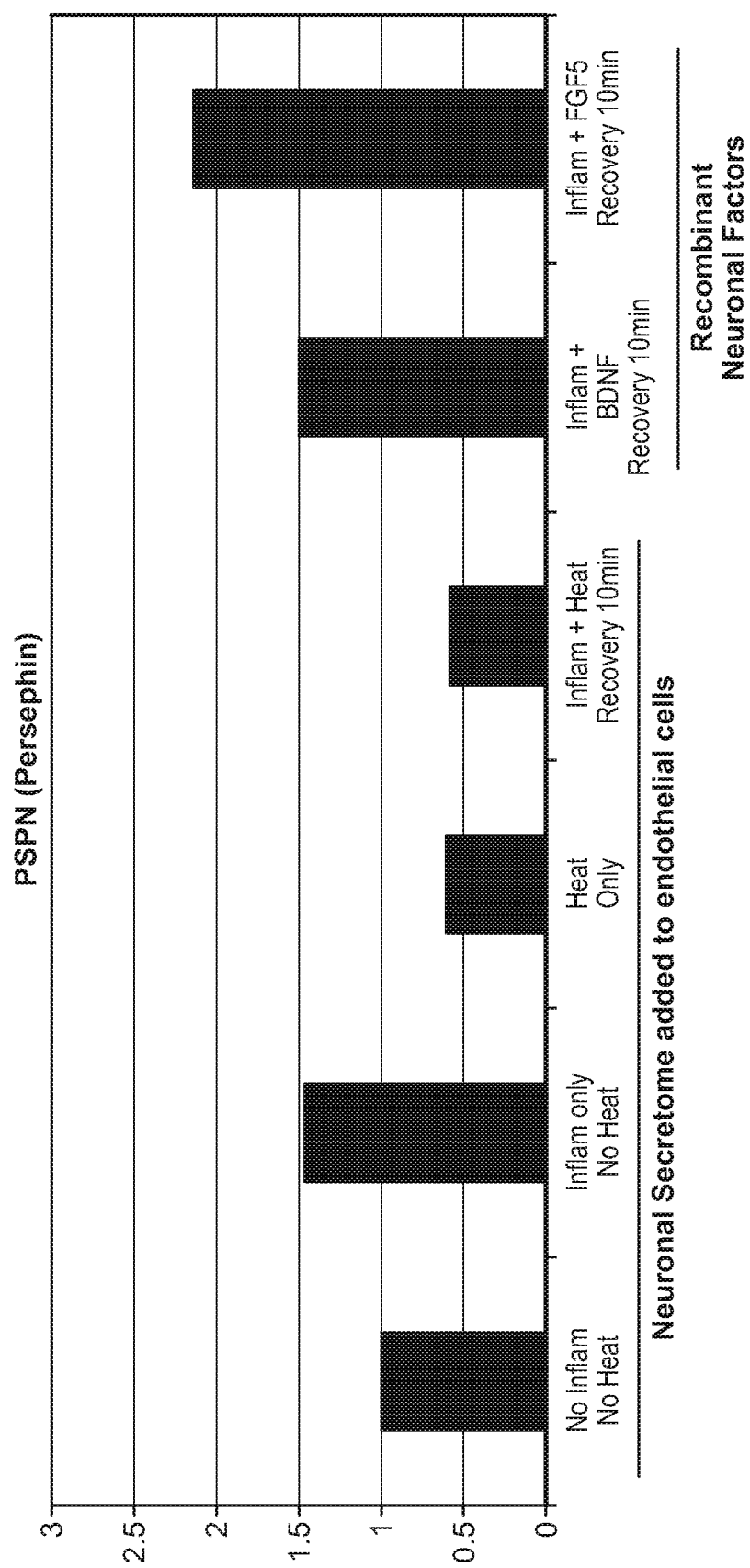
FIG. 39: Upregulation of PSPN expression in response to heat and/or inflammation and with added neuronal (recombinant) factors BDNF or FGF5.
Figure 40:
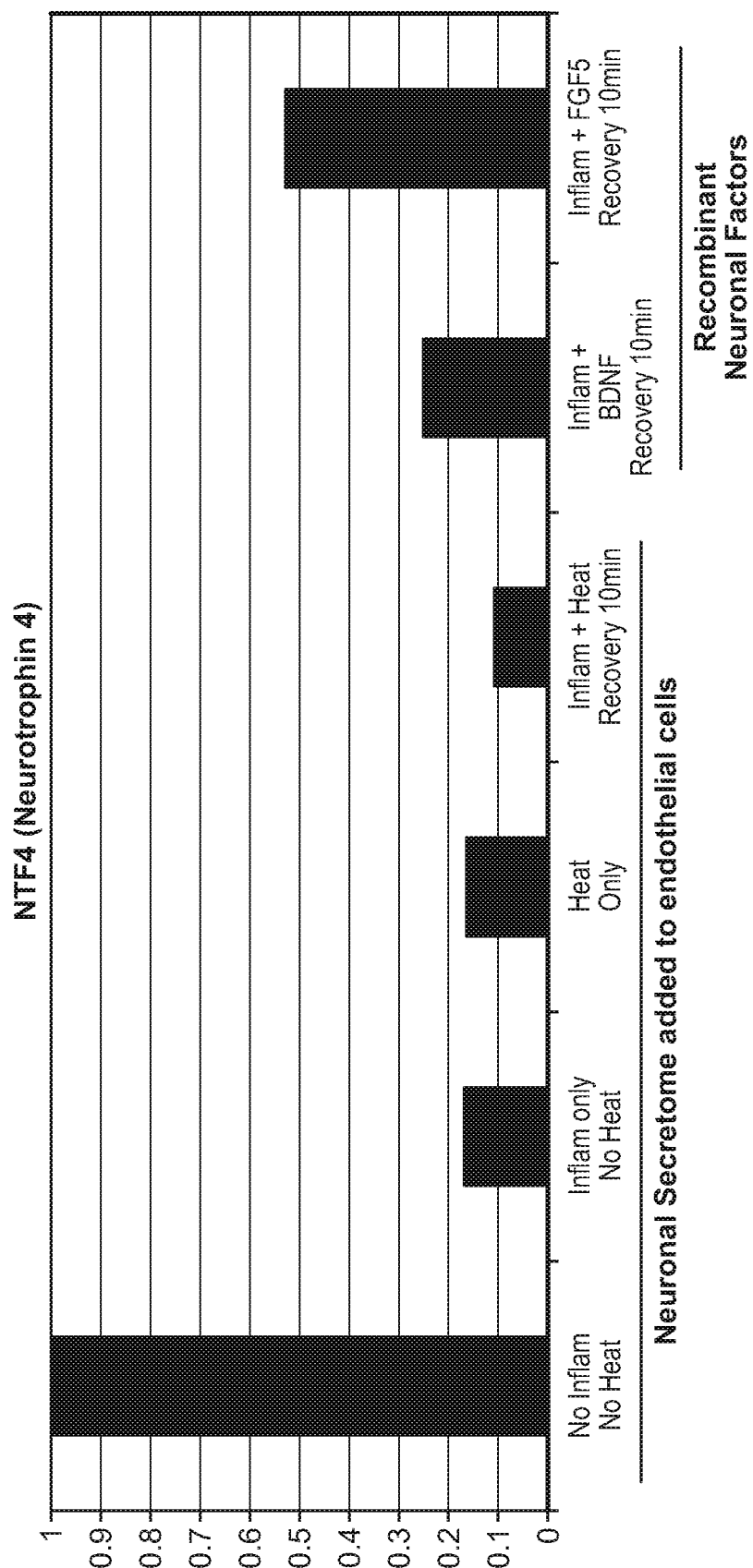
FIG. 40: Upregulation of NTF4 expression in response to heat and/or inflammation and with added neuronal (recombinant) factors BDNF or FGF5.
Figure 41:
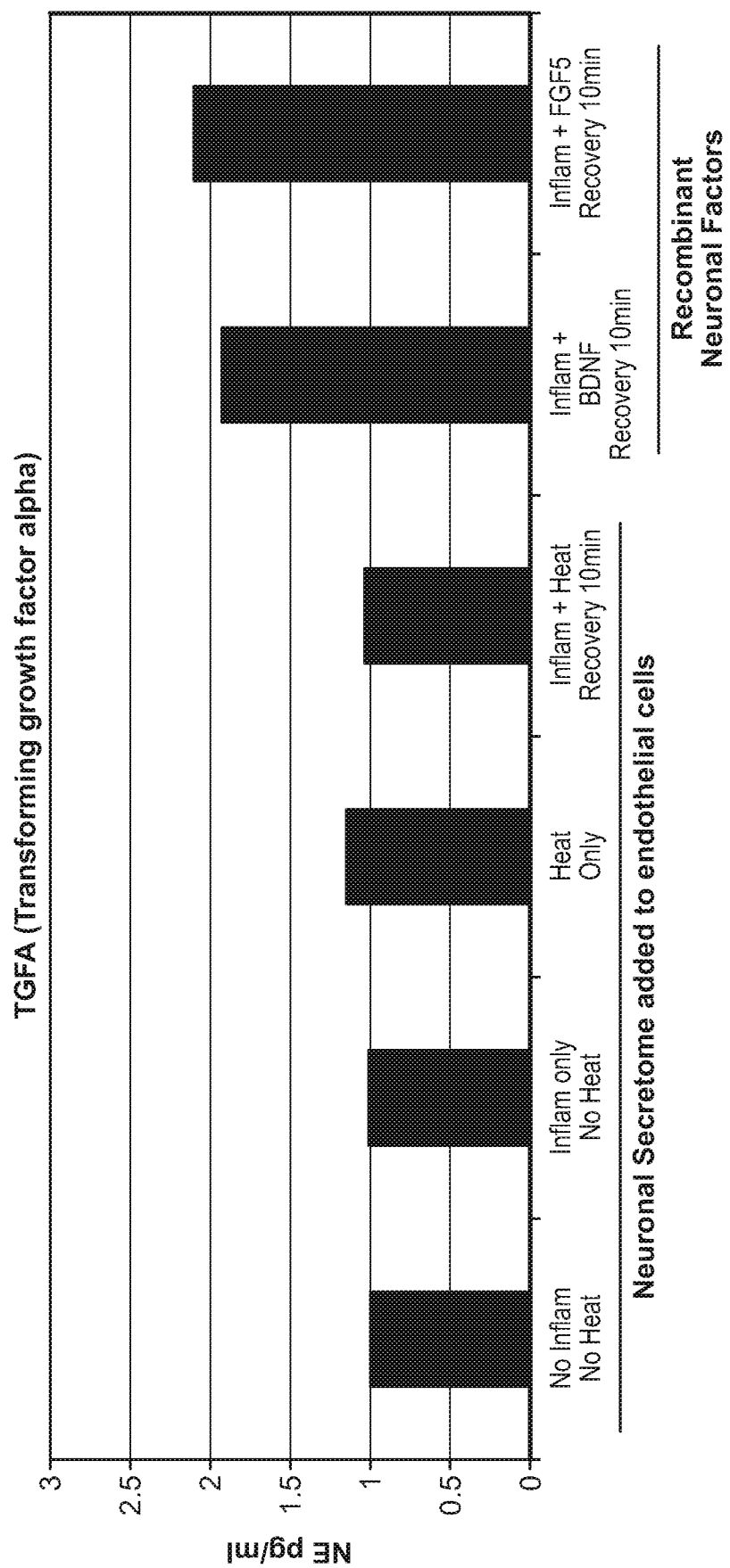
FIG. 41: Upregulation of TGFA expression in response to heat and/or inflammation and with added neuronal (recombinant) factors BDNF or FGF5.

A second set of gene profiling and secretomics experiments were performed according to the protocol set forth in FIG. 30. In the second set of experiments, neuronal LUHMES cells were treated with either heat and inflammatory conditions or recombinant stress factors such as BDNF or FGF5, then lysed and subjected to gene profiling. Conditions media was collected from LUHMES cells treated with heat and inflammatory conditions, and endothelial HCAEC were treated with either this conditioned media or recombinant neuronal stress factors such as BDNF or FGF5 for ten minutes. The endothelial cells were then lysed and subjected to gene profiling. Gene profiling of the treated LUHMES and HCAEC cells resulted in the identification of the 20 target biomarkers listed in Table 7. Results for specific proteins in this list are set forth at FIGS. 31-41.

TABLE 7

| Protein | Gene | Function/Description |
|---|---|---|
| Synuclein, alpha (FIG. 31) | SNCA | May be involved in regulation of dopamine release and transport, induces fibrillization of microtubule-associated protein tau, reduces neuronal responsiveness to various apoptotic stimuli |
| BDNF (FIG. 32) | BDNF | Promotes survival and differentiation of selected neuronal populations of the peripheral and central nervous system, participates in axonal growth and pathfinding and in modulation of dendritic growth and morphology |
| Ciliary neurotrophic factor | CNTF | Survival factor for various neuronal cell types, seems to prevent degeneration of motor axons |
| Fibroblast growth factor 2 (basic) (FIG. 33) | FGF2 | Plays important role in regulation of cell survival, cell division, angiogenesis, cell differentiation, and cell migration, functions as potent mitogen in vitro |
| Glial cell-derived neurotrophic factor 1 | GDNF | Neurotrophic factor that enhances survival and morphological differentiation of dopaminergic neurons and increases their high-affinity dopamine uptake |
| Beta-nerve growth factor 2 | NGF | Important for development and maintenance of sympathetic and sensory nervous systems, involved in differentiation and survival of neurons and in the control of gene expression for enzymes involved in neurotransmitter synthesis |
| Neurotrophin-3 | NTF3 | Neurotrophic growth factor, controls neuron survival and differentiation, seems to promote survival of visceral and proprioceptive sensory neurons |
| PF4 | Secreted | Released during platelet aggregation, neutralizes anticoagulant effect of heparin by binding more strongly to heparin than to the chondroitin-4-sulfate chains of the carrier molecule, chemotactic for neutrophils and monocytes, inhibits endothelial cell proliferation, short form is a more potent inhibitor than longer form |
| EDN2 | Secreted | Highly potent vasoconstrictive peptides, localized to non-vascular structures including epithelial cells, glia and neurons, principle physiological role is maintenance of vascular tone, have co-mitogenic activity and potentiate effects of other growth factors |
| ACE2 | Secreted | Carboxypeptidase that converts angiotensin II to angiotensin 1-7, vasodilator |
| Interferon gamma (IFN-γ) | | Member of type II interferon family, soluble cytokine with antiviral, immunoregulatory, and anti-tumor properties, potent activator of macrophages |
| Artemin (ARTN) (FIG. 34) | Secreted | Ligand for GFR-alpha-3-RET receptor complex, can also activate GFR-alpha-1-RET receptor complex, supports survival of sensory and sympathetic peripheral neurons in culture, supports survival of dopaminergic neurons of the ventral mid-brain |
| LIF | Secreted | Pleiotropic cytokine involved in nephrogenesis & ECM repair |
| Cerebellin 1 precursor (CBLN1) (FIG. 35) | Secreted | Neuromodulator, directly stimulates NE release via adenylate cyclase/PKA-dependent signaling pathway, indirectly enhances adrenocortical secretion in vivo via paracrine mechanism involving medullary catecholamine release |
| Neuregulin 1 (NRG1) (FIG. 36) | Secreted | Originally identified as 44-kD glycoprotein that interacts with NEU/ERBB2 receptor tyrosine kinase to increase phosphorylation on tyrosine residues, acts as signaling protein that mediates cell-cell interactions, plays critical roles in growth and development of multiple organ systems |
| Neuregulin 2 (NRG2) (FIG. 37) | Secreted | Member of neuregulin family |
| Neuregulin 4 (NRG4) (FIG. 38) | Secreted | Member of neuregulin family |
| Persephin (PSPN) (FIG. 39) | Secreted | Exhibits neurotrophic activity on mesencephalic dopaminergic and motor neurons |

TABLE 7-continued

| Protein | Gene | Function/Description |
|---|---|---|
| NTF4 (FIG. 40) | Secreted | Target-derived survival factor for peripheral sensory sympathetic neurons |
| Transforming growth factor alpha (TGFA) (FIG. 41) | Secreted | Mitogenic polypeptide able to bind EGF receptor/EGFR and act synergistically with TGF beta to promote anchorage-independent cell proliferation |

Example 3: In Vivo Target Biomarker Screening (Porcine Renal Arterial, Renal Venous, and Systemic Blood)

Proteomics detection studies are conducted using porcine blood collected from the renal artery to screen for protein and non-protein candidate target biomarkers that exhibit a change in secretion level at various time points after renal denervation/ablation.

Animals are broken into three groups of three animals each: naïve (no treatment), sham (catheterized but not ablated), and treated (subject to ablation at 65° C. and 90 seconds using a spiral ablation catheter device). Blood is collected using a multi-lumen OTW catheter designed to collect localized blood samples in the left or right renal artery (see U.S. Provisional Appl. No. 61/608,626 (C00002431.USP2)). Denervation is carried out using either a Symplicity™ catheter or an alternate catheter as described in U.S. patent application Ser. No. 13/281,361.

For renal artery blood collection, percutaneous vascular access is obtained through the right or left femoral artery and an introducer sheath is placed. Using fluoroscopic guidance, an appropriately sized angiographic catheter is inserted through the introducer sheath and advanced to each renal artery. One or more angiograms are performed for measurements of treated vessels.

Figure 42:
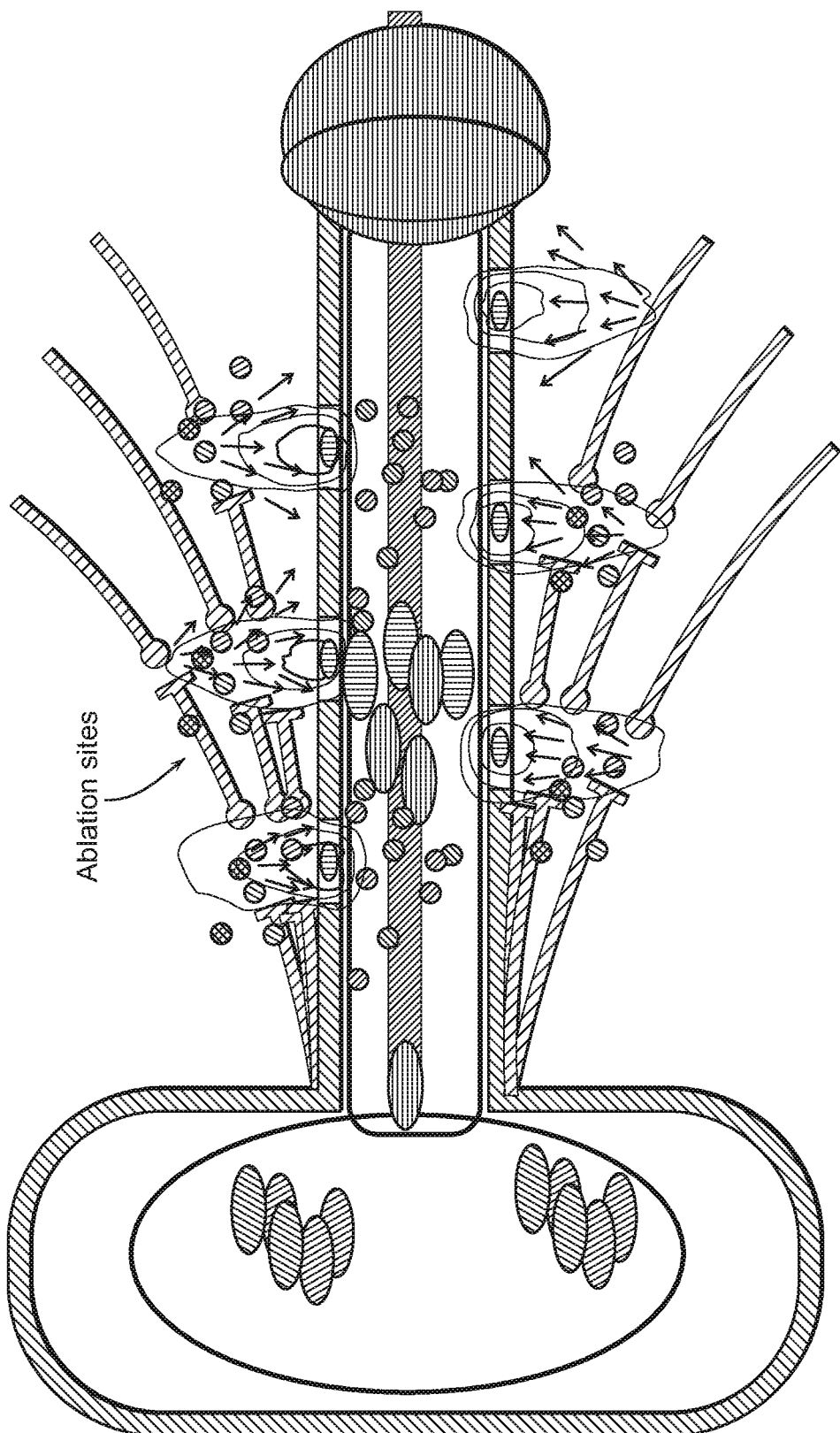
FIG. 42: Blood collection catheter for real-time assessment of post-procedural biomarkers.
Figure 43A:
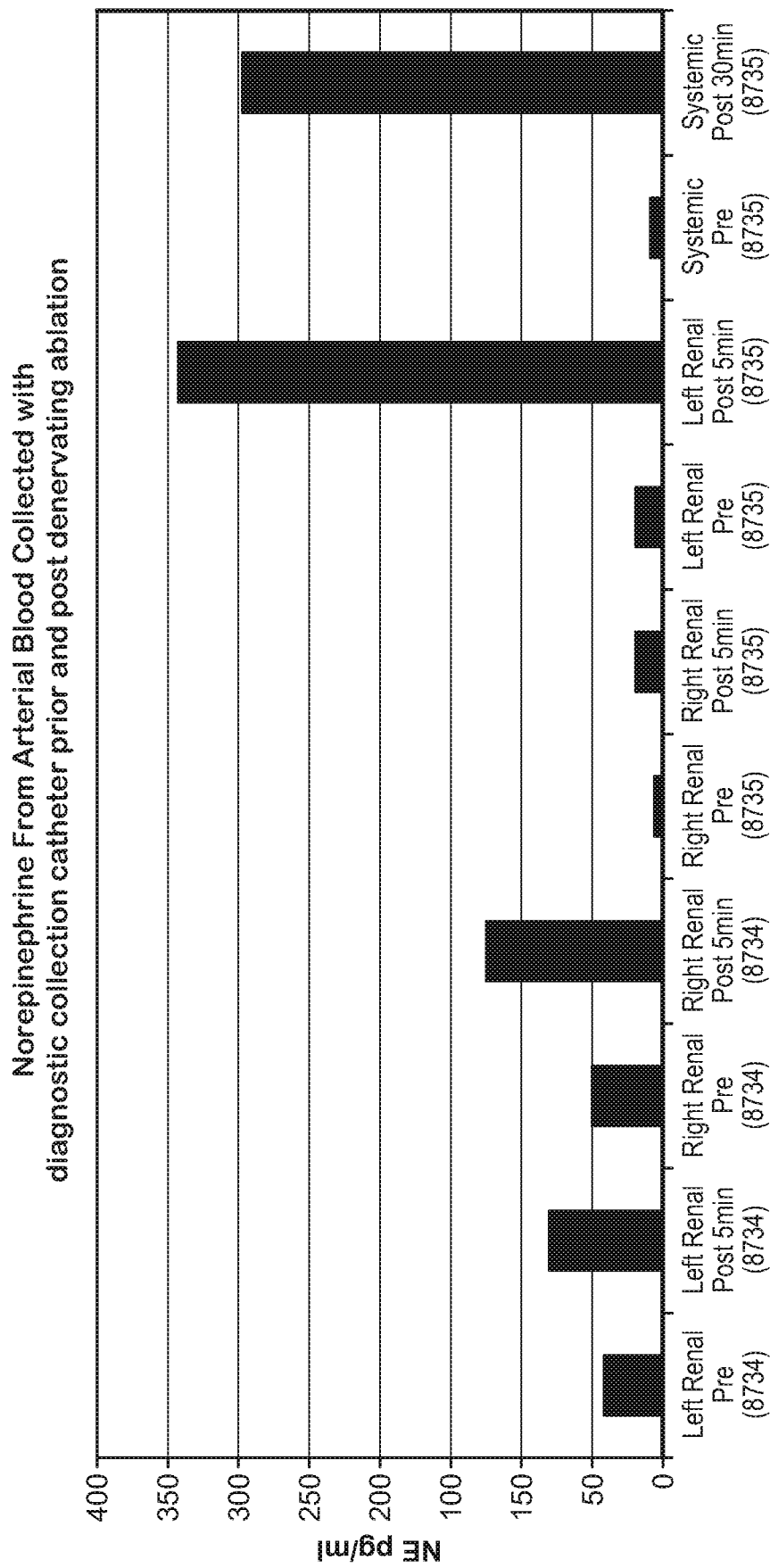
FIG. 43A-B: NE levels in renal arterial blood prior to and after denervating ablation. Increase in NE levels in renal arterial blood versus control prior to and after denervating ablation.
Figure 43B:
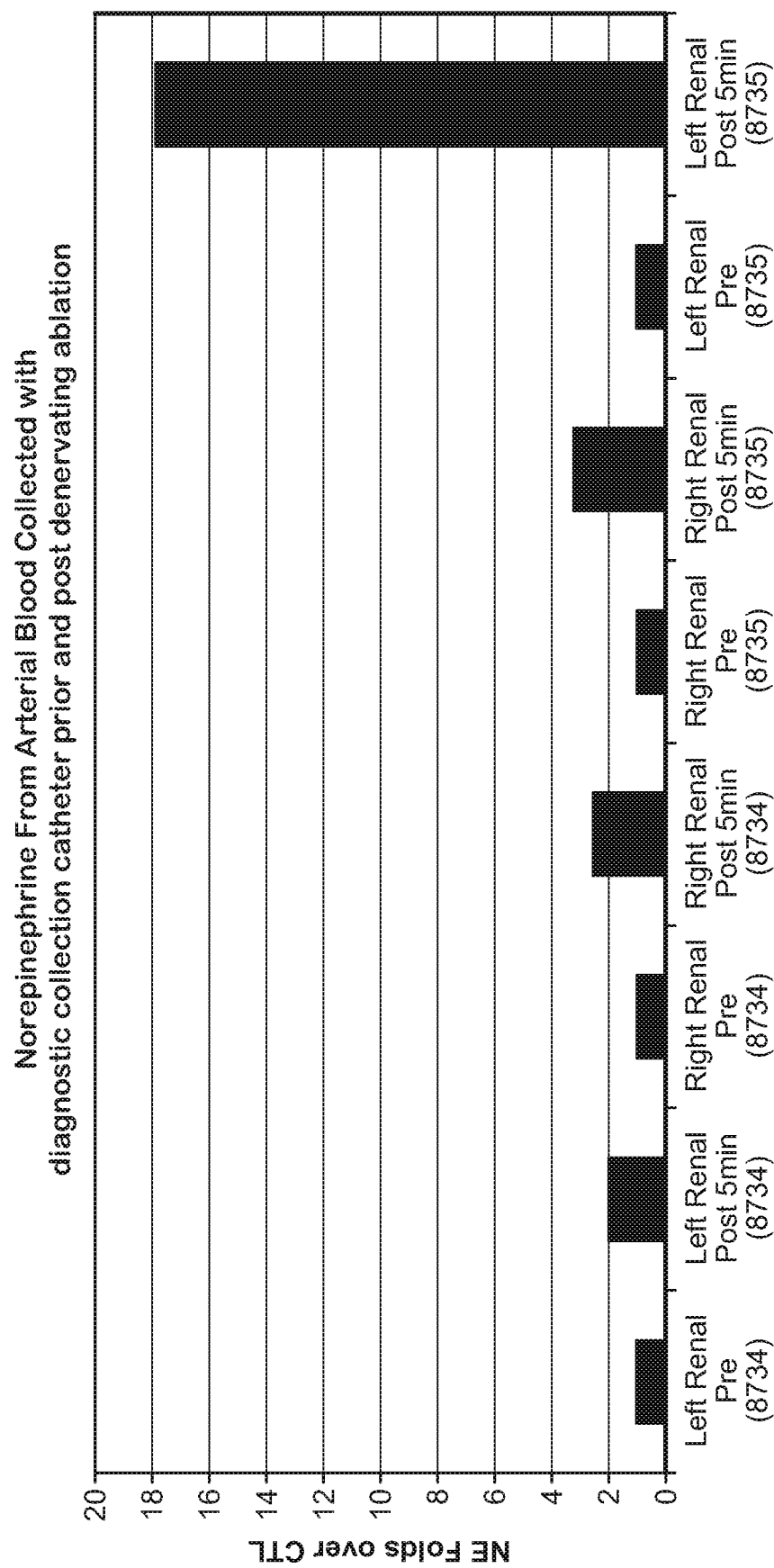
Figure 44:
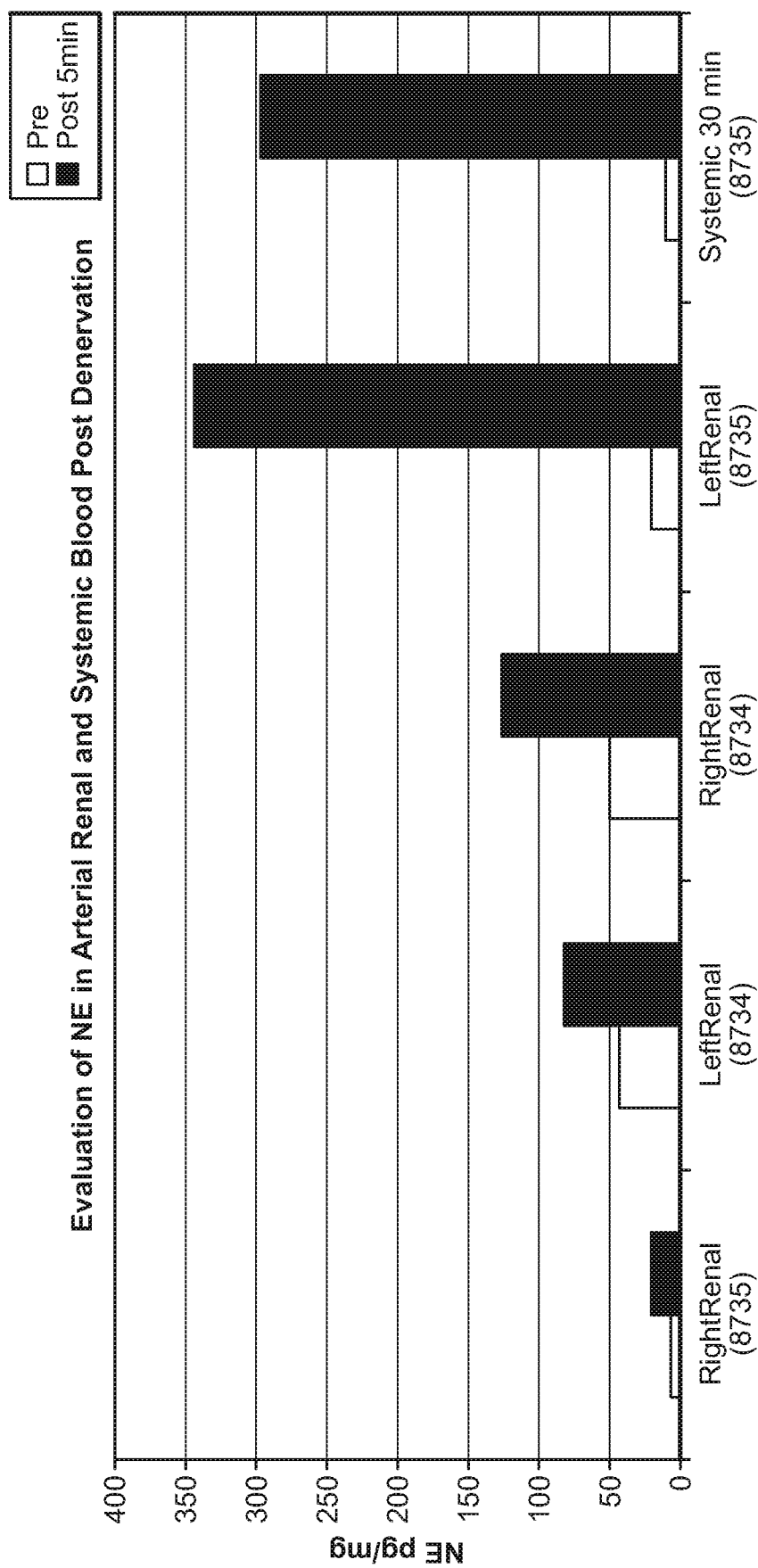
FIG. 44: NE levels in porcine renal arterial and systemic blood prior to and after denervating ablation.
Figure 45:
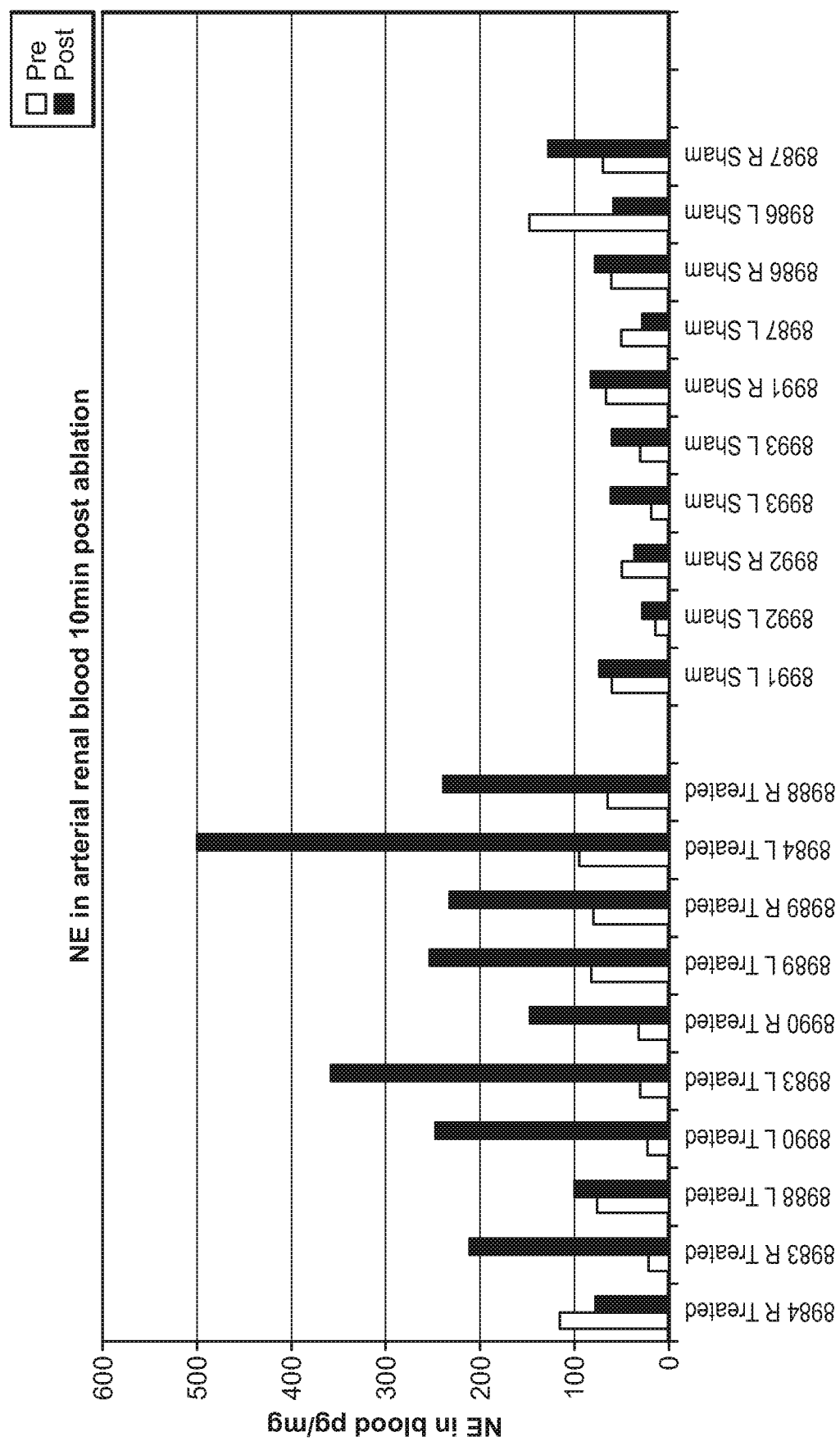
FIG. 45: NE levels in porcine renal arterial blood prior to and 10 minutes after denervating ablation.
Figure 46A:
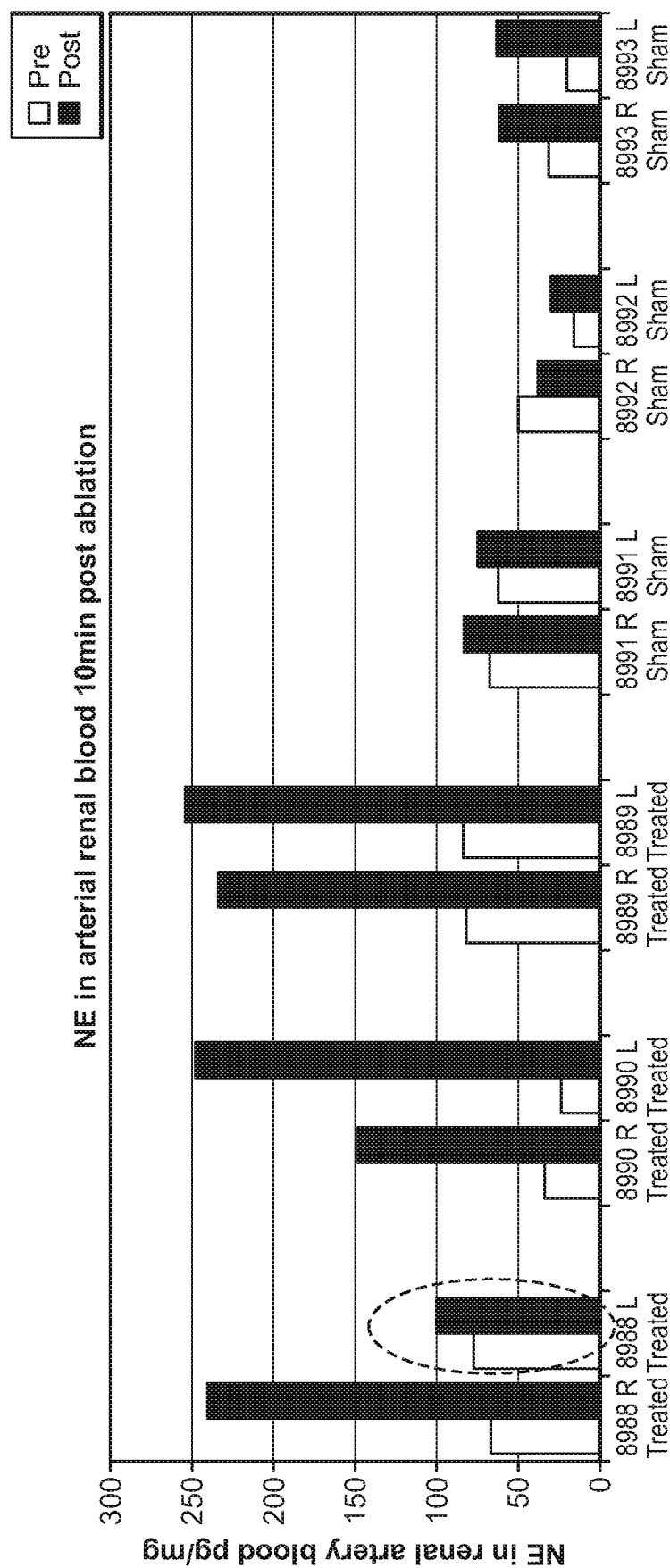
FIG. 46A-B: NE levels in porcine renal arterial blood prior to and 10 minutes after denervating ablation. Kidney NE levels 14 days after denervating ablation.
Figure 46B:
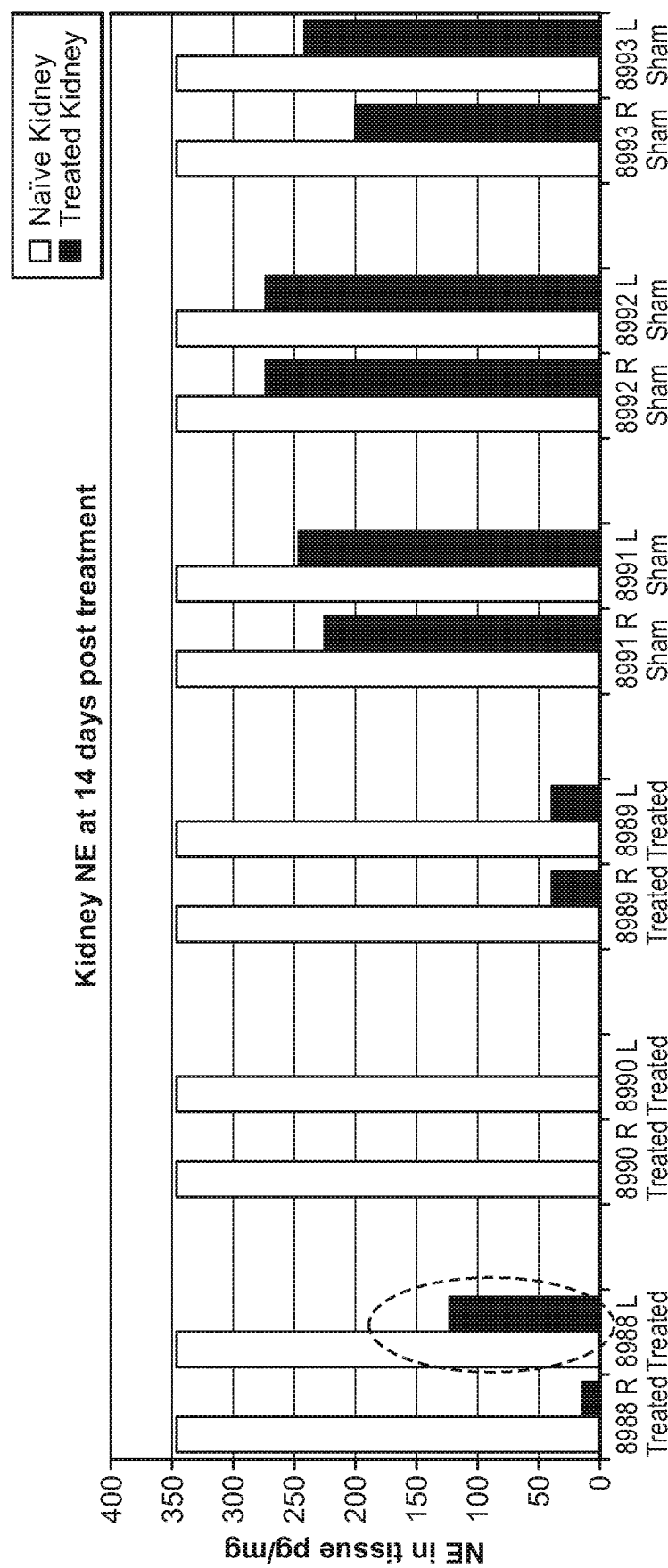
Figure 47:
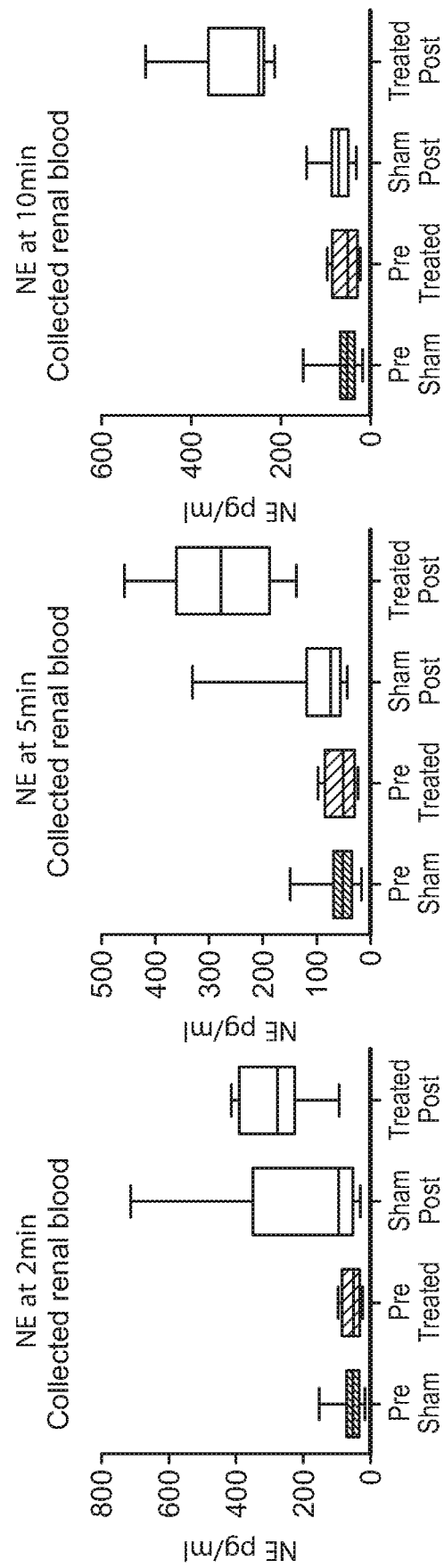
FIG. 47: NE levels in porcine renal blood at 2, 5, and 10 minutes after denervating ablation.
Figure 48:
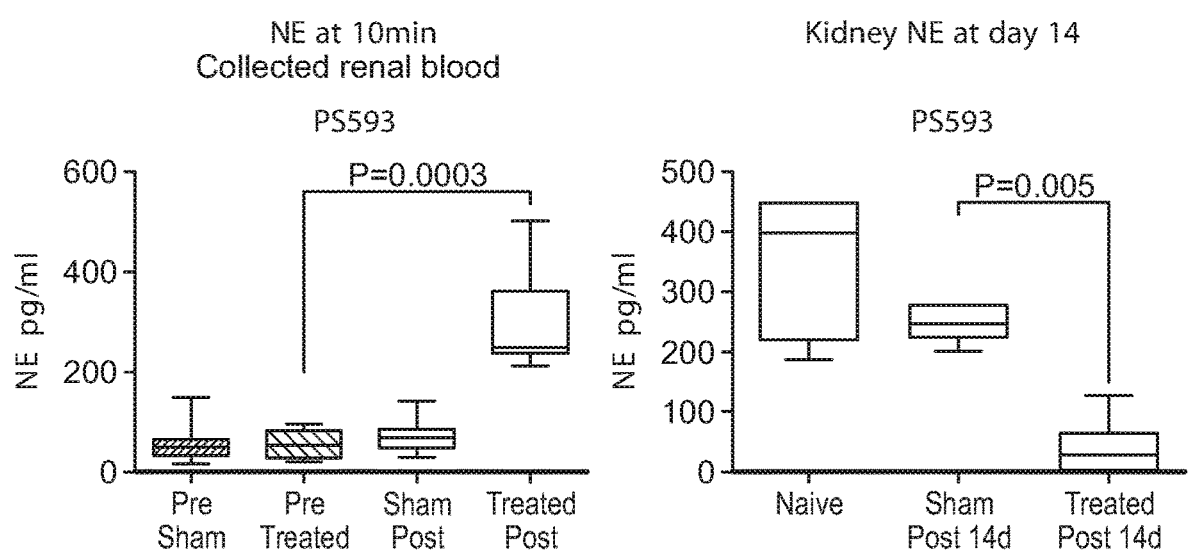
FIG. 48: NE levels in porcine arterial renal blood at 10 minutes. B. Corresponding kidney NE levels 14 days after denervating ablation.
Figure 49:
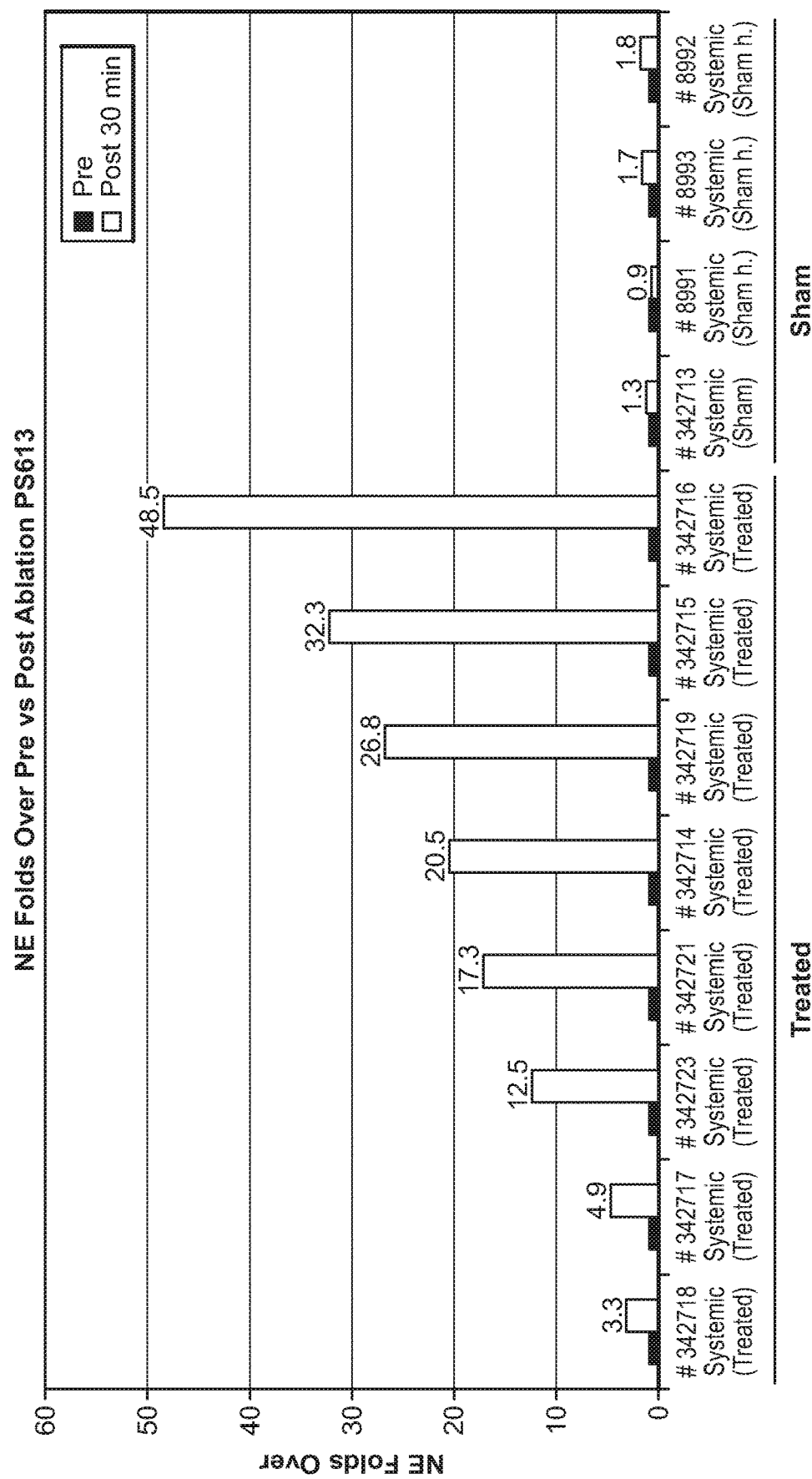
FIG. 49: Increase in NE levels after denervating ablation.

Renal arterial blood samples are collected immediately following treatment with the RF catheter and at approximately 2, 5, and 10 minutes post-ablation using a specialized collection catheter that allows for concentration of secreted factors and collection of back flow (FIG. 42). In addition, systemic arterial blood samples are collected pre-ablation and at approximately 30±5 and 60±5 minutes post-ablation. Treatment arms are summarized in Table 8.

TABLE 8

| Survival cohort | Arm | Catheter type | Minimum vessels required | Minimum number of animals |
|---|---|---|---|---|
| 0 days (acute) | 1 | Symplicity treatment (4-6 ablations) | 6 | 3 |
| | 2 | Sham (0 ablations) | 6 | 3 |
| 14 days | 3 | Symplicity treatment (4-6 ablations) | 6 | 3 |
| | 4 | Sham (0 ablations) | 6 | 3 |
| | 5 (Naïve) | N/A | 6 | 3 |
| Totals | | | 30 | 15 |

Figure 50:
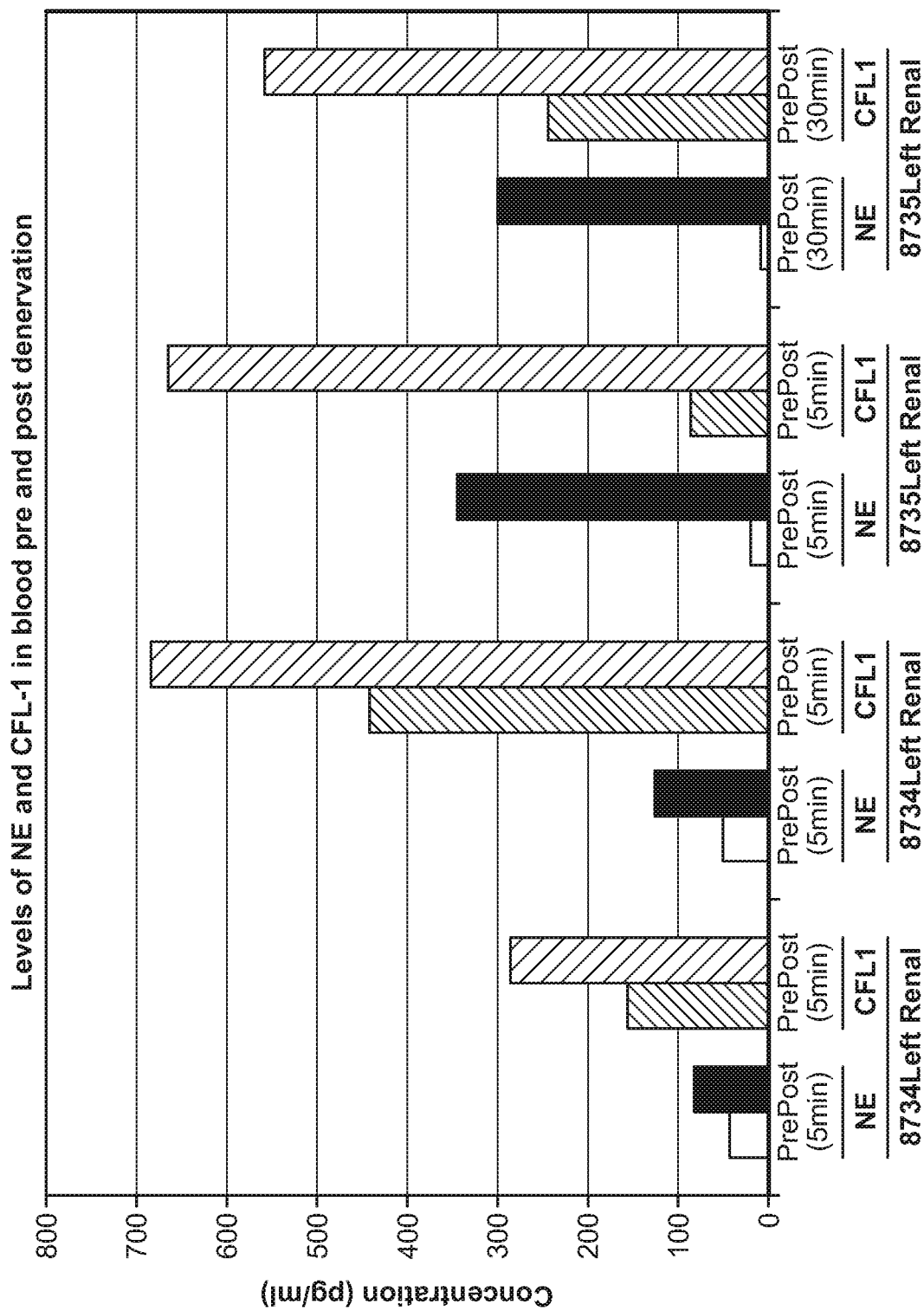
FIG. 50: Changes in NE and CFL-1 levels after denervating ablation.

An initial evaluation was carried out using NE and CFL1, with protein levels being assessed by ELISA. Results for NE are set forth in FIGS. 43-49. Results for CFL1 are set forth in FIG. 50.

This screening method may be used to evaluate one or more of the candidate target biomarkers set forth in Tables 1-7. Additional candidate biomarkers that may be evaluated include factors released in the kidney from stressed/denervated nerve ends such as neurotransmitters stored at the nerve ends (e.g., NPY), enzymes stored in nerve ends (e.g., DBH), ions released upon denervation (e.g., $Ca^{2+}$), and factors released from renal artery endothelial cells and the kidney that may play a physiological role in response to stress or modulation of renal sympathetic system (e.g., Endothelin 1, 2, and 3). Examples of these additional potential candidate target biomarkers are set forth in Table 9. Additional screens may be carried out using other porcine biological samples such as urine.

TABLE 9

| Factors released in the kidney as a result of denervation | Function |
|---|---|
| Norepinephrine/noradrenaline (NE) | Catecholamine with multiple roles including as a hormone and a neurotransmitter. NE is converted into epinephrine by the enzyme phenylethanolamine N-methyltransferase (PNMT), with S-adenosyl-L-methionine (SAMe) as the cofactor. Areas of the body that produce or are affected by norepinephrine are described as noradrenergic. One of the most important functions of norepinephrine is its role as the neurotransmitter released from the sympathetic neurons. |

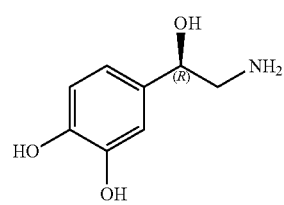

TABLE 9-continued

| Factors released in the kidney as a result of denervation | Function |
|---|---|
| Neuropeptide Y (NPY) | 36-amino acid peptide neurotransmitter found in the brain and autonomic nervous system, augments the vasoconstrictor effects of noradrenergic neurons. |
| Dopamine (DBN) | Converted into NE by dopamine β-hydroxylase (DBH), with $O^2$ and L-ascorbic acid as cofactors. |
| $Ca^{2+}$ | Mediates nerve signaling and regeneration and could be released upon denervation |
| Renin | Highly specific endopeptidase, functions to generate angiotensin I from angiotensinogen in plasma, initiating a cascade of reactions that produce an elevation of blood pressure and increased sodium retention by the kidney. |
| Dopamine beta-hydroxylase (DBH) | Oxidoreductase belonging to the copper type II ascorbate-dependent monooxygenase family, present in synaptic vesicles of postganglionic sympathetic neurons, converts dopamine to norepinephrine. Protein exists in both soluble and membrane-bound forms. |
| Angiotensin (AGT) | Acts directly on vascular smooth muscle as a potent vasoconstrictor, affects cardiac contractility and heart rate through its action on the sympathetic nervous system, alters renal sodium and water absorption through its ability to stimulate the zona glomerulosa cells of the adrenal cortex to synthesize and secrete aldosterone. |
| Endothelin 1, Endothelin 2, Endothelin 3 | Endothelium-derived vasoactive peptides involved in a variety of biological functions. Active form is a 21 amino acid peptide processed from the precursor protein. Active peptide is a ligand for EDNRB, and this interaction is essential for development of neural crest-derived cell lineages, such as melanocytes and enteric neurons. Endothelin receptors are widely expressed in all tissues, consistent with their physiological role as vasoactive peptides. Also localized to non-vascular structures including epithelial cells, glia and neurons. Principle physiological role of endothelin receptors is maintenance of vascular tone. |
| Neurotensin (NTS) | 170 AA protein, may play endocrine or paracrine role in regulation of fat metabolism, causes contraction of smooth muscle. |
| Amyloid beta (A4) precursor protein (APP) | 770 AA protein, N-APP binds TNFRSF21, triggering caspase activation and degeneration of both neuronal cell bodies (via caspase-3) and axons (via caspase-6). |

Selected Embodiments of Renal Neuromodulation Systems and Devices

Figure 51:
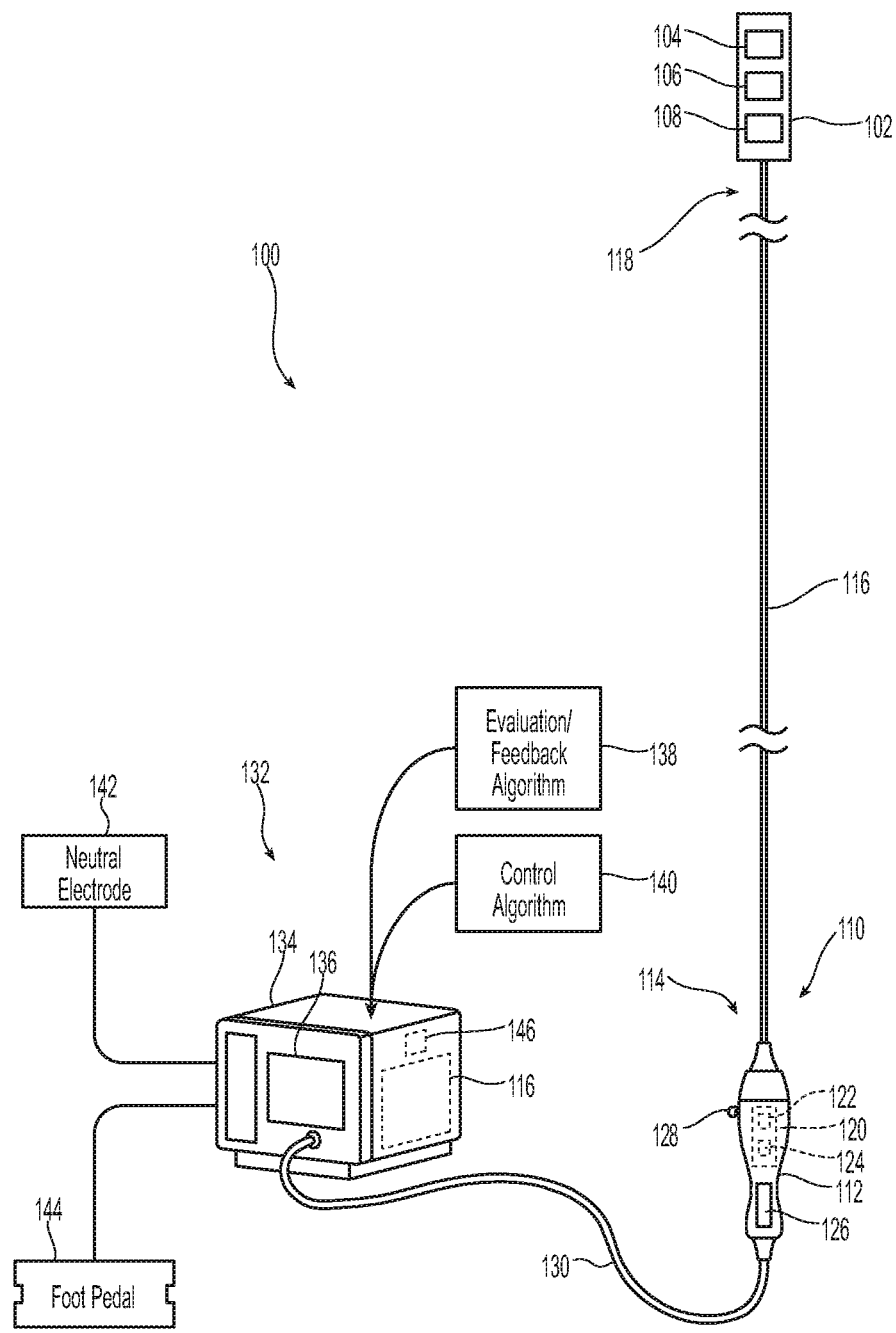
FIG. 51: Partially-schematic perspective view illustrating a renal neuromodulation system including a treatment device configured in accordance with an embodiment of the present technology.

FIG. 51 is a partially-schematic diagram illustrating a system 100 configured in accordance with an embodiment of the present technology. The system 100 can include a treatment device 110 (e.g., a catheter) operably coupled to a console (e.g., an energy generator) 132 via a connector 130 (e.g., a cable). As shown in FIG. 51, the treatment device 110 can include an elongated shaft 116 having a proximal portion 114, a handle assembly 112 at a proximal region of the proximal portion 114, and a distal portion 118 extending distally relative to the proximal portion 114. The elongated shaft 116 can be configured to locate the distal portion 118 intravascularly (e.g., within a renal artery) or within another suitable body lumen (e.g., within a ureter) at a treatment location. The treatment device 110 can further include a neuromodulation and sampling assembly 102 carried by or affixed to the distal portion 118 of the elongated shaft 116. The neuromodulation and sampling assembly 102 can include one or more energy delivery elements 104 (shown schematically in FIG. 51) (e.g., electrodes) configured to modulate nerves at or near the treatment location as well as one or more sampling ports 108 (also shown schematically in FIG. 51) configured to collect biological samples from the treatment location or another suitable location near the treatment location.

The system 100 can further include an analyzer 120 (e.g., a biosensor) configured to receive and analyze the biological sample collected by the neuromodulation and sampling assembly 102 for the level or activity of one or more target biomarkers. In certain embodiments, the analyzer may be configured to further analyze one or more additional biological parameters related to neuromodulation.

Upon receipt of the sample by the analyzer 120, detection and/or capture agents within the analyzer 120 can interact with target biomarkers of the collected sample, if present. In at least some cases, binding of a target biomarker to a capture agent and/or interaction of the target biomarker with a detection agent can result in a biomarker response (e.g., a change in color, formation of a reaction product, or another suitable response). The physicochemical transducer 122 can transform the biomarker response into a more easily measurable and quantifiable signal (e.g., a colorimetric, fluorescent, heat, energy, or electric signal) that can be sensed by or communicated to the processing device 124 for storage and/or analysis. The processing device 124 can be operably coupled to an indicator 126 carried by the handle 112. The indicator 126 can be configured to indicate suitable information related to processing the target biomarker (e.g., a sample date, a status of the target biomarker, and/or a status of nerve modulation based on a detected level or activity of the target biomarker). The indication can be auditory and/or visual. In some embodiments, the indicator 126 includes a suitable display component, such as a light emitting diode, an imaging display, and/or a graphical user interface.

In some embodiments, the analyzer 120 is integrated into the console 132 instead of the handle 112. In these embodiments, for example, the analyzer 120 can be configured to receive a biological sample directly from the treatment device 110 (e.g., via a fluid conduit (not shown) (e.g., polymer tubing) within or separate from the connector 130). The fluid conduit can extend between the treatment device 110 and the console 132 where an air or fluid pump (not shown) integrated with the analyzer 120 can draw a biological sample into a portion of the analyzer 120. Alternatively, the air or fluid pump can be housed in the handle 112 to transfer a biological sample to the analyzer 120 contained within the console. In these and other embodiments, the handle 112 can include a removable container (not shown) configured to receive a biological sample collected via the sampling port 108 and conveyed to the container via the shaft 116. For detection and/or analysis of a target biomarker within the sample, the removable container can be removed from the handle 112 and transferred to the analyzer 120 (e.g., when the analyzer 120 is a remote a standalone device or when the analyzer 120 integrated into the console 132, and/or in other embodiments in which the analyzer 120 is remote relative to the treatment device 110). The removable container may be reusable or disposable.

The console 132 can be configured to generate a selected form and/or magnitude of energy for delivery to the treatment site via the energy delivery element 104 of the neuromodulation and sampling assembly 102. For example, the console 132 can include an energy generator (not shown) configured to generate RF energy (monopolar or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, chemicals (e.g., drugs or other agents), radiation (e.g., infrared, visible, gamma), or another suitable type of energy. In some embodiments, neuromodulation may be achieved by chemical-based treatment including delivering one or more chemicals (e.g., guanethidine, ethanol, phenol, a neurotoxin (e.g., vincristine)), or another suitable agent selected to alter, damage, or disrupt nerves. In a particular embodiment, the console 132 includes a RF generator operably coupled to one or more energy delivery elements 104 of the neuromodulation and sampling assembly 102. Furthermore, the console 132 can be configured to control, monitor, supply, or otherwise support operation of the treatment device 110. For example, a control mechanism, such as foot pedal 144, may be connected (e.g., pneumatically connected or electrically connected) to the console 132 to allow an operator to initiate, terminate and/or adjust various operational characteristics of the energy generator, such as power delivery. In some embodiments, the console 132 may be configured to provide delivery of a monopolar electric field via the energy delivery element 104. In such embodiments, a neutral or dispersive electrode 142 may be electrically connected to the console 132 and attached to the exterior of the patient (not shown).

In some embodiments, the system 100 includes a remote control device (not shown) that can be configured to be sterilized to facilitate its use within a sterile field. The remote control device can be configured to control operation of the neuromodulation and sampling assembly 102, the console 132, and/or other suitable components of the system 100. For example, the remote control device can be configured to allow for selective activation of the neuromodulation and sampling assembly 102. In other embodiments, the remote control device may be omitted and its functionality may be incorporated into the handle 112 or console 132.

As shown in FIG. 51, the console 132 can include a primary housing 134 having a display 136. In some embodiments, the console 132 includes a processing device 146 having processing circuitry (e.g., a microprocessor). The console 132 can be configured to execute an automated control algorithm 140 and/or to receive control instructions from an operator. Furthermore, the console 132 can be configured to provide feedback to an operator before, during, and/or after a treatment procedure via the display 136 and/or via an evaluation/feedback algorithm 138. For example, the feedback can be based on output from the analyzer 120. The processing device 146 can be configured to execute stored instructions relating to the control algorithm 140 and/or the evaluation/feedback algorithm 138.

The console 132 can be configured to communicate with the treatment device 110 (e.g., via the connector 130). For example, the neuromodulation and sampling assembly 102 and/or the shaft 116 can include a sensor 106 (e.g., a chemical sensor, a temperature sensor, a pressure sensor, or a flow rate sensor) and a sensor lead (not shown) (e.g., an electrical lead or a pressure lead) configured to carry a signal from the sensor 106 to the handle 112. The connector 130 can be configured to carry the signal from the handle 112 to the console 132. The processing device 146 of the console 132 can be configured to communicate with the processing device 124 of the analyzer 120 (e.g., via the connector 130, Bluetooth, wireless, or in another suitable manner when the analyzer 120 is within the handle 112 or otherwise remote relative to the console 132).

In some embodiments, the console 132 includes a vacuum 148 or other suitable negative pressure source (e.g., a syringe) operably coupled to the sampling port 108 of the neuromodulation and sampling assembly 102. In other embodiments, the vacuum 148 can be a standalone device separate from the console 132. The vacuum 148 can be in fluid connection with the sampling port 108 via the shaft 116. Negative pressure generated by the vacuum 148 can be used, for example, to draw a biological sample into the sampling port 108. In yet other embodiments, the treatment device 110 can include an adapter (not shown) (e.g., a luer lock) configured to be operably coupled to a syringe (not shown) and the syringe can be used to apply negative pressure to the shaft 116.

FIG. 52A is a side view illustrating the neuromodulation and sampling assembly 102 in a low-profile or delivery state in accordance with an embodiment of the present technology. The neuromodulation and sampling assembly 102 can include a neuromodulation element 200, a sampling element 202, and an occlusion element 204. In some embodiments, the neuromodulation element 200 and the sampling element 202 are distal to the occlusion element 204 and the neuromodulation element 200 is distal to the sampling element 202. In other embodiments, the neuromodulation element 200 and the sampling element 202 are distal to the occlusion element 204 and the sampling element 202 is distal to the neuromodulation element 200. In still other embodiments, the neuromodulation element 200, the sampling element 202, and the occlusion element 204 can have another suitable arrangement. A proximal region 208 of the neuromodulation and sampling assembly 102 can be carried by or affixed to the distal portion 118 of the elongated shaft 116. For example, all or a portion (e.g., a proximal portion) of the neuromodulation and sampling assembly 102 can be an integral extension of the shaft 116. In some embodiments, the profile of the neuromodulation and sampling assembly can increase between the neuromodulation element 200 and the sampling element 202. A distal region 206 of the neuromodulation and sampling assembly 102 may terminate distally with, for example, an atraumatic, flexible curved tip 214 having an opening 212 at its distal end. In some embodiments, the distal region 206 of the neuromodulation and sampling assembly 102 may also be configured to engage another element of the system 100 or treatment device 110.

FIG. 52B is an enlarged view of a portion of the neuromodulation and sampling assembly 102 of FIG. 52A. FIG. 53 is a cross-sectional end view taken along line 3-3 in FIG. 52A. Referring to FIGS. 52A-53 together, the neuromodulation and sampling assembly 102 can include the one or more energy delivery elements 104 (e.g., RF electrodes, ultrasound transducers, cryotherapeutic cooling assemblies, etc.) carried by a support structure 210 as part of the neuromodulation element 200. The energy delivery elements 104, for example, can be separate band electrodes axially spaced apart along the support structure 210 (e.g., adhesively bonded to the support structure 210 at different positions along the length of the support structure 210). In other embodiments, the neuromodulation and sampling assembly 102 may have a single energy delivery element 104 at or near the distal portion 118 of the shaft 116.

In some embodiments, the energy delivery elements 104 are formed from a suitable electrically conductive material (e.g., a metal, such as gold, platinum, alloys of platinum and iridium, etc.). The number, arrangement, shape (e.g., spiral and/or coil electrodes) and/or composition of the energy delivery elements 104 may vary. The individual energy delivery elements 104 can be electrically connected to the console 132 by a conductor or bifilar wire 300 extending through a lumen 302 of the shaft 116 and/or support structure 210. For example, the individual energy delivery elements 104 may be welded or otherwise electrically coupled to corresponding energy supply wires 300, and the wires 300 can extend through the elongated shaft 116 for the entire length of the shaft 116 such that proximal ends of the wires 300 are coupled to the handle 112 and/or to the console 132.

As shown in the enlarged cut-away view of FIG. 52B, the support structure 210 can be a tube (e.g., a flexible tube) and the neuromodulation and sampling assembly 102 can include a pre-shaped control member 220 positioned within the tube. Upon deployment, the control member 220 can bias at least a portion of the neuromodulation and sampling assembly 102 (e.g., the neuromodulation element 200) into a deployed state (FIG. 56C or 56D). For example, the control member 220 can have a pre-set configuration that gives at least a portion of the neuromodulation and sampling assembly 102 a helical or spiral configuration in the deployed state (FIG. 56C or 56D). In some embodiments, the control member 220 includes a tubular structure comprising a nitinol multifilar stranded wire with a lumen 222 therethrough and sold under the trademark HELICAL HOLLOW STRAND (HHS), and commercially available from Fort Wayne Metals of Fort Wayne, Ind. The lumen 222 can define a passageway for receiving a guide wire 600 that extends proximally from the opening 212 at the tip 214 of the neuromodulation and sampling assembly 102.

FIGS. 54 and 55 are cross-sectional end views taken, respectively, along lines 4-4 and 5-5 of FIG. 52A. With reference to FIGS. 52A-55 together, the neuromodulation and sampling assembly 102 can include the sampling port 108 as part of the sampling element 202. The sampling port 108 can be in fluid connection with a sampling lumen 400 that extends proximally along the shaft 116 from sampling port 108 to the handle 112. In some embodiments, the sampling lumen 400 can be coupled to the vacuum 148 or a syringe (not shown) to facilitate retrieval of a sample through the sampling port 108 and conveyance of the sample along the sampling lumen 400. To prevent the sample from contaminating the vacuum 148 or syringe, the sampling lumen 400 can include a one-way valve or seal (not shown) at a location along the length of the sampling lumen 400 distal to the negative pressure source inlet. In some embodiments, an inner cross-sectional area of the sampling lumen 400 and/or an area of the sampling port can be selected to achieve an adequate pressure drop across the sampling port 108.

The sampling element 202 can further include an occlusion member 218 (e.g., a compliant, semi-compliant, or non-compliant balloon, an expandable basket, a stent-like structure, etc.) as part of the occlusion element 204. The occlusion member 218 can be configured to at least partially occlude a vessel (e.g., a renal artery) or lumen in which the neuromodulation and sampling assembly 102 is positioned. In some embodiments, the occlusion member 218 extends around a segment of the shaft 116 that includes an inflation opening 216. For example, the occlusion member 218 can be laser-bonded or adhered by other suitable methods to an outer surface of the shaft 116 at axially spaced apart locations distal and proximal, respectively, relative to the inflation opening 216.

The inflation opening 216 can connect to an inflation lumen 500 that extends proximally along the shaft 116 from the inflation opening 216 to the handle 112. Control of the occlusion element 204 and/or occlusion member 218 (e.g., control over inflation/expansion volume, inflation/expansion timing and/or deflation/collapse timing) can be manual or automatic (e.g., based on a pre-set schedule or algorithm). As shown in FIG. 55, the sampling lumen 400 and the inflation lumen 500 can be positioned within the shaft 116 at least proximate to opposite sides of the lumen 222. In other embodiments, the sampling lumen 400 and the inflation lumen 500 can be positioned within the support structure 210. In yet other embodiments, the sampling lumen 400, the inflation lumen 500 and the lumen 222 can have other suitable shapes, sizes and/or arrangements.

Several embodiments of methods for utilizing the system 100 to provide real-time or relatively contemporaneous (e.g., less than 30 minutes) renal neuromodulation efficacy feedback in accordance with the present technology are described herein. In a particular embodiment, a method includes: (a) collecting a pre-neuromodulation biological sample at a treatment site via a sampling element 202 of a neuromodulation and sampling assembly 102; (b) determining a baseline or pre-neuromodulation level or activity of one or more target biomarkers within the pre-neuromodulation biological sample; (c) performing a neuromodulation procedure using a neuromodulation element 200 of the neuromodulation and sampling assembly 102; (d) expanding an occlusion member 218 to at least partially occlude a vessel or lumen in which the treatment site is located; (e) collecting a post-neuromodulation biological sample at the treatment site via the sampling element 202; (f) determining a post-neuromodulation level or activity for the target biomarker(s); and (g) comparing the post-neuromodulation level or activity to the baseline level or activity to provide neuromodulation efficacy feedback.

Figure 56A:
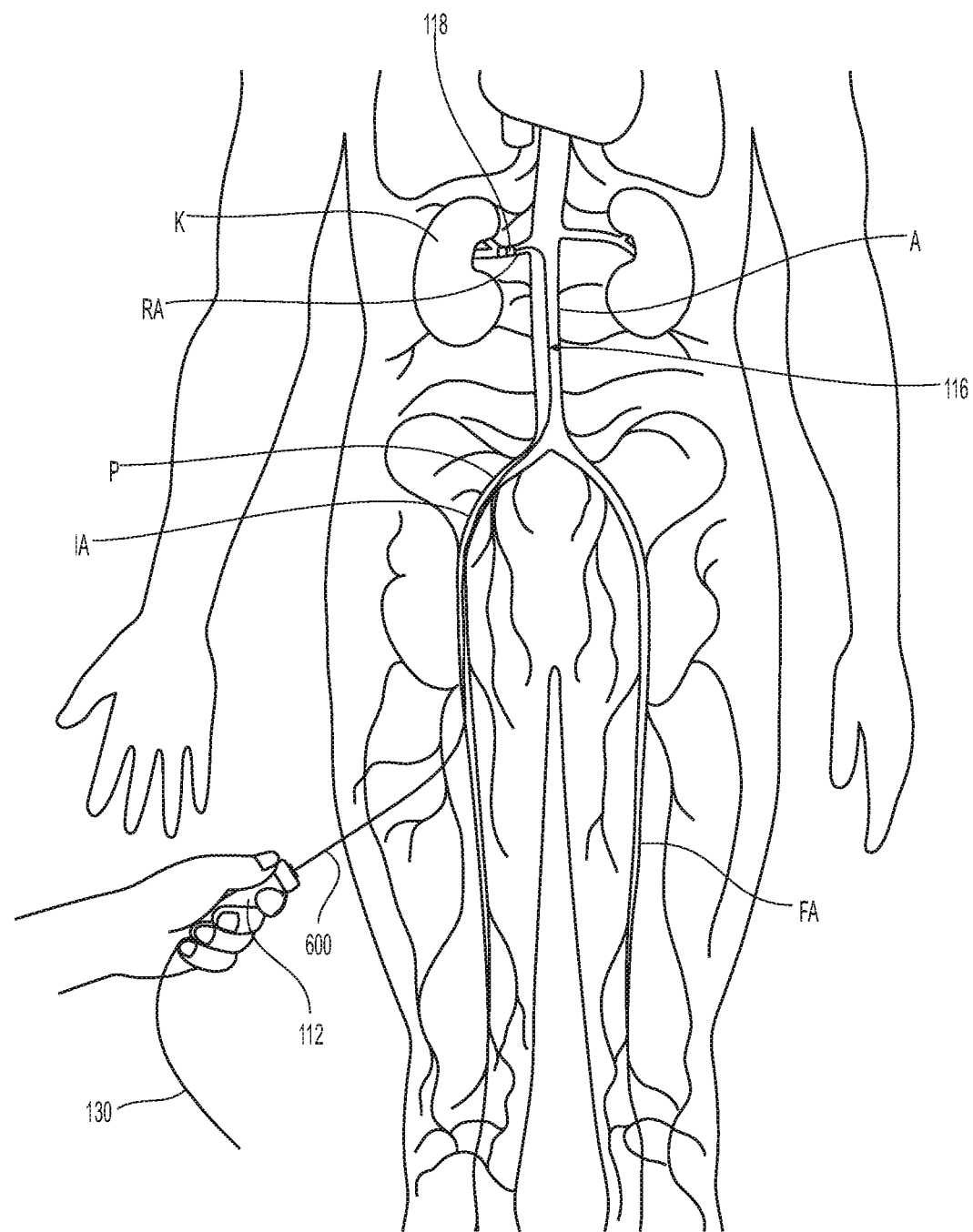
FIG. 56A-D: Partially cross-sectional anatomical front view illustrating advancing the treatment device shown in FIG. 51 along an intravascular path in accordance with an embodiment of the present technology. B. Cross-sectional view of the neuromodulation and sampling assembly shown in FIG. 52A within a renal artery in accordance with an embodiment of the present technology. C. Cross-sectional view of the neuromodulation and sampling assembly shown in FIG. 52A illustrating deploying a portion of the neuromodulation and sampling assembly at a treatment location within the renal artery in accordance with an embodiment of the present technology. D. Cross-sectional view of the neuromodulation and sampling assembly of FIG. 52A illustrating occluding a portion of the renal artery at a treatment location in accordance with an embodiment of the present technology.
Figure 56B:
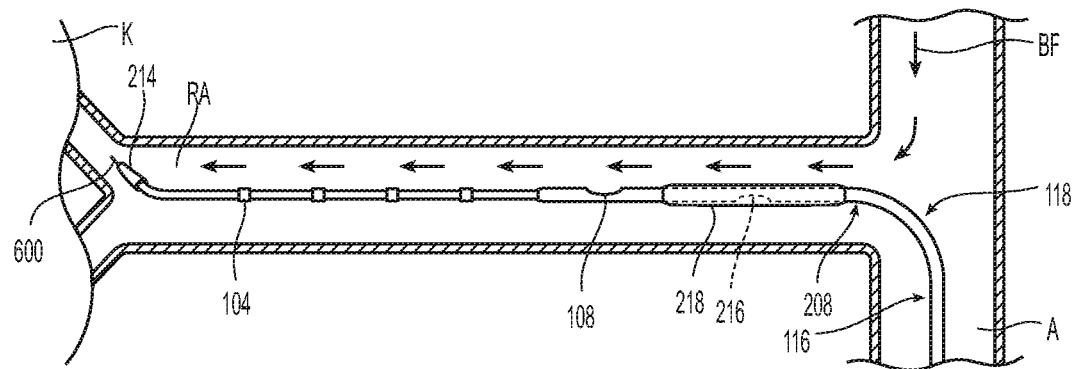
Figure 56C:
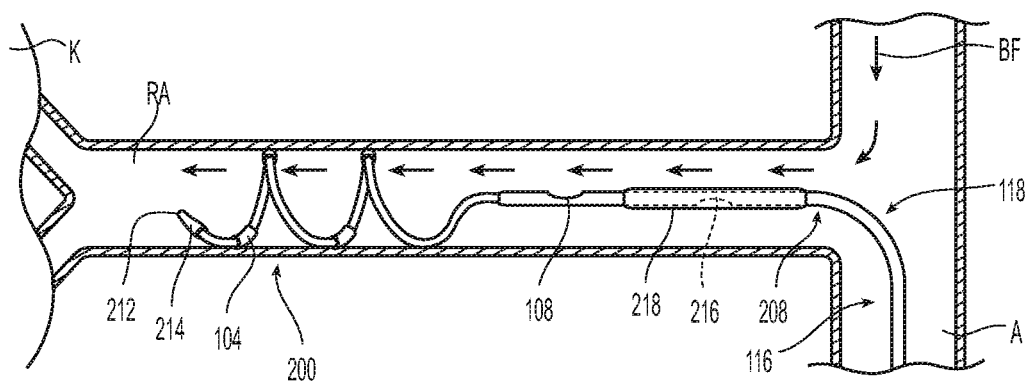
Figure 56D:
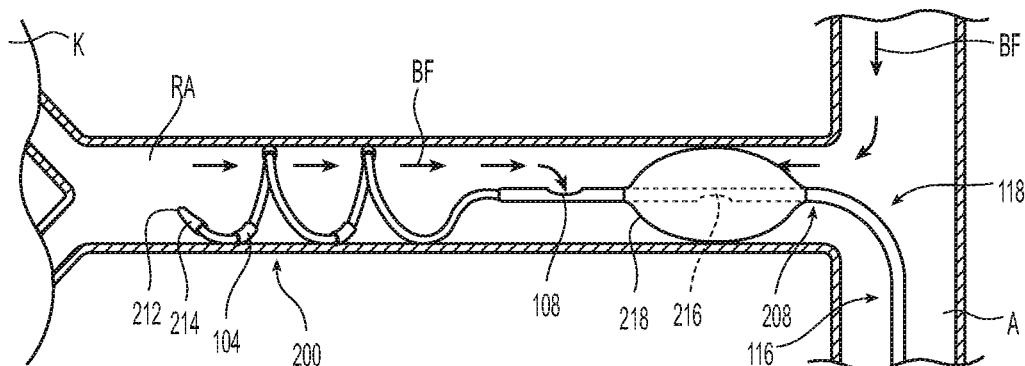

Referring to FIG. 56A, intravascular delivery of the neuromodulation and sampling assembly 102 can include percutaneously inserting a guide wire 600 within the vasculature at an access site (e.g., femoral, brachial, radial, or axillary artery) and moving the shaft 116 and the neuromodulation and sampling assembly 102 (in the delivery state) along the guide wire until at least a portion of the neuromodulation and sampling assembly 102 reaches the treatment location (as shown in FIG. 56B). In some embodiments, the shaft 116 and the neuromodulation and sampling assembly 102 can include the lumen 222 (FIGS. 53-55) configured to receive a guide wire 600 in an over-the-wire or rapid exchange configuration. As illustrated, a section of the proximal portion 114 of the shaft 116 can be extracorporeally positioned and manipulated by the operator (e.g., via the actuator 128) to advance the shaft 116 through the sometimes tortuous intravascular path (P) and remotely manipulate the distal portion 118 of the shaft 116.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation and sampling assembly 102. For example, a fluoroscopy system (e.g., including a flat-panel detector, x-ray, or c-arm) can be rotated to accurately visualize and identify the target treatment site. In other embodiments, the treatment site can be located using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the treatment device 110. Further, in some embodiments, image guidance components (e.g., IVUS, OCT) may be integrated with the treatment device 110 and/or run in parallel with the treatment device 110 to provide image guidance during positioning of the neuromodulation and sampling assembly 102. For example, image guidance components (e.g., IVUS or OCT) can be coupled to a distal portion of the treatment device 110 to provide three-dimensional images of the vasculature proximate the target site to facilitate positioning or deploying the neuromodulation and sampling assembly 102 within the target renal blood vessel.

Once the neuromodulation and sampling assembly 102 is positioned at a treatment location, the guide wire 600 can be at least partially introduced (e.g., inserted) into or removed (e.g., withdrawn) from the neuromodulation and sampling assembly 102 to transform or otherwise move the neuromodulation and sampling assembly 102 to a deployed state. In the deployed state, for example, the energy delivery elements 104 of the neuromodulation and sampling assembly 102 can be positioned in stable contact with a wall of the vessel or lumen for delivering energy, as illustrated by FIG. 56C. Though the embodiment shown in FIG. 56C shows a deployed neuromodulation and sampling assembly 102 in which only the neuromodulation element 200 is spiral or helically-shaped, in other embodiments, all or a greater portion of the neuromodulation and sampling assembly 102 can be spiral or helically-shaped. Furthermore, the neuromodulation element 200, the sampling element 202, and/or other portions of the neuromodulation and sampling assembly 102 can have other suitable shapes, sizes, and/or configurations (e.g., bent, deflected, helical, spiral, zig-zag, Malecot, etc.).

In some embodiments, the neuromodulation and sampling assembly 102 may be delivered to a treatment site within a guide sheath (not shown) with or without using the guidewire 600. When the neuromodulation and sampling assembly 102 is at the target site, the guide sheath may be at least partially withdrawn or retracted and the neuromodulation and sampling assembly 102 can be transformed into the deployed state. For example, at least a portion of the neuromodulation and sampling assembly 102 can have a shape memory corresponding to a deployed state and the sheath can prevent the neuromodulation and sampling assembly 102 from deploying in response to the shape memory before reaching the treatment location. In still other embodiments, the shaft 116 may be steerable itself such that the neuromodulation and sampling assembly 102 may be delivered to the treatment site without the aid of the guide wire 600 and/or guide sheath.

Examples of other suitable neuromodulation delivery configurations, deployment configurations and/or deployment mechanisms can be found in U.S. application Ser. No. 12/910,631, filed Oct. 22, 2010, entitled "APPARATUS, SYSTEMS, AND METHODS FOR ACHIEVING INTRAVASCULAR, THERMALLY-INDUCED RENAL NEUROMODULATION," U.S. application Ser. No. 13/281,361, filed Oct. 25, 2011, entitled "CATHETER APPARATUSES HAVING MULTI-ELECTRODE ARRAYS FOR RENAL NEUROMODULATION AND ASSOCIATED SYSTEMS AND METHODS," and U.S. Provisional Application No. 61/646,218, filed May 5, 2012, entitled "MULTI-ELECTRODE CATHETER ASSEMBLIES FOR RENAL NEUROMODULATION AND ASSOCIATED SYSTEMS AND METHODS," which are all incorporated herein by reference in their entireties.

In the deployed state, at least a portion of the neuromodulation and sampling assembly 102 can be configured to contact an inner wall of the renal artery and to cause a fully-circumferential lesion without the need for repositioning. For example, the neuromodulation element 200 can be configured to form a lesion or series of lesions (e.g., a helical/spiral lesion or a discontinuous lesion) that is fully-circumferential overall, but generally non-circumferential at longitudinal segments of the treatment location. This can facilitate precise and efficient treatment with a low possibility of vessel stenosis. In other embodiments, the neuromodulation element 200 can be configured to form a partially-circumferential lesion or a fully-circumferential lesion at a single longitudinal segment of the treatment location. In some embodiments, the therapeutic element 502 can be configured to cause therapeutically-effective neuromodulation (e.g., using ultrasound energy) without contacting a vessel wall.

At one or more timepoints prior to neuromodulation, the sampling element 202 of the assembly 102 can collect a pre-neuromodulation biological sample at or near the treatment site to determine an initial, pre-neuromodulation level or activity of one or more target biomarkers. In some embodiments, the collected baseline sample can be conveyed directly from the sampling port 108 through the sampling lumen 400 to the analyzer 120 (e.g., when the analyzer 120 is incorporated into the handle 112). The analyzer 120 can be configured to analyze the pre-neuromodulation sample to detect a baseline level of one or more target biomarkers. In other embodiments, the collected baseline sample can be conveyed directly from the sampling port 108 through the sampling lumen 400 to the console 132 via the connector 130 and/or a separate collection connector (not shown) between the handle 112 and the console 132. As discussed below, the baseline level or value can be compared to a post-neuromodulation level to evaluate the efficacy of the neuromodulation. When the analysis is complete, the baseline data obtained by the analyzer 120 from the baseline analysis may be stored by memory of the analyzer 120, or in some embodiments, the baseline data can be communicated (e.g., via the connector 130 and/or wirelessly) to memory of the console 132 for storage and/or processing. In addition, the baseline data may be displayed by an analyzer display (not shown) on the handle 112 and/or the console display 136 (FIG. 51). After the baseline data has been obtained, the baseline sample can be removed from the analyzer 120 in the handle 112 to prevent contamination of incoming samples. Furthermore, in some embodiments, the analyzer 120 can be configured to separate and store more than one sample (e.g., reducing or eliminating the need to service the analyzer 120 in between collections).

After the neuromodulation and sampling assembly 102 is adequately positioned in the vessel or lumen, the neuromodulation element 200 can be used to purposefully apply or withdraw energy to or from the tissue to induce one or more desired neuromodulating effects on localized regions of the renal artery and adjacent regions of the renal plexus (RP), which lay intimately within, adjacent to, or in close proximity to the adventitia of the renal artery (RA). During and/or after the application of energy, the system 100 can detect changes in the level or activity of one or more target biomarkers associated with neuromodulation and provide real-time or relatively contemporaneous feedback of neuromodulation efficacy.

Before, during, and/or after the energy delivery or withdrawal, the occlusion member 218 carried by the occlusion element 204 of the neuromodulation and sampling assembly 102 can be inflated and/or expanded to at least partially occlude the vessel or lumen proximal to the treatment site, as shown in FIG. 56D (the direction of blood flow is indicated by arrows "BF"). After the occlusion member 218 is inflated and/or expanded, a negative pressure source can be activated to draw a post-neuromodulation sample proximally through the sampling port 108 and sampling lumen 400 to a proximal portion 114 of the treatment device 110 (e.g., the handle 112). Occlusion of the vessel or lumen upstream of the treatment site is expected to isolate and/or preserve target biomarkers released into the vessel or lumen as a result of the neuromodulation. Additionally, full or partial occlusion can cause pooling of the blood in the vessel or lumen distal to the occlusion member 218 that facilitates collection of a sufficient sample size (e.g., 1-5 cc) for subsequent analysis. In some embodiments, a sufficient sample size volume can be significantly smaller (e.g., less than about 1 cc). For example, the sampling lumen 400 may include an in vivo sensor (described below) and/or test element (described below) that can detect biomarker levels in sample volumes less than about 1 cc. Because the average renal artery contains about 1 cc of collectable biological sample, the occlusion member 218 may remain in a fully or partially inflated and/or expanded state for about 1 to 5 minutes before collection to allow sufficient pooling of the biological sample in the renal artery. Alternatively, in some embodiments, collection of a sample can occur during or after neuromodulation without use of an occlusion member 218. In these cases, the sampling element 202 can be distal to the neuromodulation element 200 so as to be downstream of the treatment site with respect to blood flow and more likely to collect target biomarkers resulting from the neuromodulation.

In some embodiments, collection of the post-neuromodulation sample can include an iterative process of inflating and/or expanding the occlusion member 218, collecting a first quantity of the sample, partially deflating the occlusion member 218 to allow perfusion of the renal artery, then re-inflating and/or re-expanding the occlusion member 218 to collect a second quantity of the sample. Such an iterative process can be used to collect any desired number of sample quantities until a sufficient sample volume has been reached. As discussed above, inflation and deflation of the occlusion member 218 can be automatically or manually controlled to achieve a desired occlusion to perfusion ratio. In some embodiments, the therapeutic element 502 can be configured to radially expand into a deployed state 504 at the treatment location.

The devices, systems and methods for conveying the post-neuromodulation sample from the sampling port 108 to an analyzer 120 and for analyzing the post-neuromodulation sample can be the same as that described above with respect to the baseline or pre-neuromodulation sample. Once determining the post-neuromodulation target biomarker level or activity, the processing circuitry associated with the analyzer 120, handle 112, and/or console 132 can compare the post-neuromodulation biomarker level or activity to the baseline level or activity and provide real-time or relatively contemporaneous feedback (e.g., auditory or visual) to the practitioner as to the efficacy of the neuromodulation. For example, target biomarkers for use in the methods disclosed herein may exhibit a change (e.g., a two-fold or greater, a three-fold or greater, a five-fold or greater, or a ten-fold or greater change) in level or activity in response to neuromodulation. If the feedback indicates that a neuromodulation treatment has not been effective, the neuromodulation element 200 can be re-activated (e.g., shifted and then reactivated) to perform a second neuromodulation. Once the second neuromodulation treatment is complete, an additional post-neuromodulation sample can be collected and analyzed to determine whether or not to continue treatment. This process can be repeated until sufficient neuromodulation has been effectuated at the treatment site.

FURTHER EXAMPLES

The following examples are illustrative of several embodiments of the present technology:

1. A method of monitoring the efficacy of a renal neuromodulation procedure in a human subject, the method comprising:
  determining a baseline level or activity of one or more target biomarkers;
  at least partially inhibiting sympathetic neural activity in a renal nerve of the subject via a neuromodulation assembly;
  determining a post-neuromodulation level or activity for the target biomarker(s); and
  comparing the post-neuromodulation level or activity to the baseline level or activity, wherein the neuromodulation procedure is classified as successful if the post-neuromodulation level or activity differs significantly from the baseline level or activity.

2. The method of example 1 wherein at least partially inhibiting sympathetic neural activity in a renal nerve of the subject comprises delivering energy to the renal nerve via the neuromodulation assembly to modulate the renal nerve.

3. The method of example 2 wherein the energy is radio frequency (RF) energy.

4. The method of example 2 wherein the energy is selected from the group consisting of pulsed RF energy, microwave energy, laser light energy, optical energy, ultrasound energy, high-intensity focused ultrasound energy, magnetic energy, direct heat energy, and cryotherapeutic energy.

5. The method of any one of examples 1 to 4 wherein at least partially inhibiting sympathetic neural activity in a renal nerve of the subject comprises delivering a chemical to the renal nerve via the neuromodulation assembly to modulate the renal nerve.

6. The method of any one of examples 1 to 5 wherein the neuromodulation assembly comprises an intravascularly positioned catheter carrying an energy delivery element positioned at least proximate to the renal nerve.

7. The method of any one of examples 1 to 6 wherein at least partially inhibiting sympathetic neural activity in a renal nerve of the subject comprises thermally modulating the renal nerve via the neuromodulation assembly from within a renal blood vessel of the subject.

8. The method of example 1 wherein at least partially inhibiting sympathetic neural activity in a renal nerve of the subject comprises delivering a chemical agent to tissue at a treatment location in the renal blood vessel in a manner that modulates sympathetic neural activity.

9. The method of any one of examples 1 to 8 wherein the one or more target biomarkers are selected from the group consisting of ADRA2b, ATP1A1, BDNF, BMP7, BNP, BTG2, CALCB, CD40L, CDKN1B, CDKN2B/p15, CLU, DNAJA4, DNAJB1, EDN3, ETB, FASLG, FOS, HMOX-1, HSPA5, HSPA14, HSPB1, HSPD1, HSPH1, IL-10, ITGAM, KLKB1, LIF, MC2R, NTF3, P2RY12, SELE, SLC2A5/GLUT5, SOD2, TLR3, TLR4, TLR7, and TNFRSF1B.

10. The method of any one of examples 1 to 8 wherein the one or more target biomarkers are selected from the group consisting of CASP10, CCL13, CCND1, CD70, CRYAB, CPS1, DNAJB1, DNAJB11, HSPA1A, HSPA1B, HSPB6, IL-10, KIT, LTA, MYLK3, NODAL, NPY1R, POU1F1, and TCP1.

11. The method of any one of examples 1 to 8 wherein the one or more target biomarkers are selected from the group consisting of ACTA2, CACY/2A9, CFL1, CTAG1A1/CTAG21, LDHA, MGC141/TMEM141, NAA20/NAT5, NM23B, PAHX/PHYH1, PFDN1, PLK-2, TUBA1B, and VIM.

12. The method of any one of examples 1 to 8 wherein the one or more target biomarkers are selected from the group consisting of SNCA, BDNF, CNTF, FGF2, GDNF, NGF2, NTF3, PF4, EDN2, ACE2, IFN-γ, ARTN, LIF, CBLN1, NRG1, NRG2, NRG4, PSPN, NTF4, and TGFA.

13. The method of any one of examples 1 to 8 wherein the one or more target biomarkers are selected from the group consisting of NE, CFL1, NPY, DBN, $Ca^{2+}$, renin, DBH, AGT, endothelin 1, 2, and 3, NTS, and APP.

14. The method of any one of examples 1 to 13 wherein the post-neuromodulation level or activity of the target biomarker(s) is determined at 10 minutes, 24 hours, or 7 days post-denervation.

15. A method of performing a renal neuromodulation procedure in a human patient, the method comprising:
intravascularly positioning a neuromodulation assembly proximate to a renal nerve of the patient;
determining a baseline level or activity of one or more target biomarkers prior to or after positioning the neuromodulation assembly;
partially disrupting function of the renal nerve by applying energy to the renal nerve via the neuromodulation assembly;
determining a post-neuromodulation level or activity for the target biomarker(s); and
comparing the post-neuromodulation level or activity to the baseline level or activity,
wherein the neuromodulation procedure is classified as successful if the post-neuromodulation level or activity differs significantly from the baseline level or activity.

16. The method of example 15 wherein partially disrupting function of the renal nerve comprises reducing renal nerve hyperplasia in the patient.

17. The method of example 15 or example 16 wherein partially disrupting function of the renal nerve comprises reducing the total number of functioning renal nerves of the patient to levels at or near levels observed in normotensive patients.

18. The method of any one of examples 15 to 17 wherein the one or more target biomarkers are selected from the group consisting of ADRA2b, ATP1A1, BDNF, BMP7, BNP, BTG2, CALCB, CD40L, CDKN1B, CDKN2B/p15, CLU, DNAJA4, DNAJB1, EDN3, ETB, FASLG, FOS, HMOX-1, HSPA5, HSPA14, HSPB1, HSPD1, HSPH1, IL-10, ITGAM, KLKB1, LIF, MC2R, NTF3, P2RY12, SELE, SLC2A5/GLUT5, SOD2, TLR3, TLR4, TLR7, and TNFRSF1B.

19. The method of any one of examples 15 to 17 wherein the one or more target biomarkers are selected from the group consisting of CASP10, CCL13, CCND1, CD70, CRYAB, CPS1, DNAJB1, DNAJB11, HSPA1A, HSPA1B, HSPB6, IL-10, KIT, LTA, MYLK3, NODAL, NPY1R, POU1F1, and TCP1.

20. The method of any one of examples 15 to 17 wherein the one or more target biomarkers are selected from the group consisting of ACTA2, CACY/2A9, CFL1, CTAG1A1/CTAG21, LDHA, MGC141/TMEM141, NAA20/NAT5, NM23B, PAHX/PHYH1, PFDN1, PLK-2, TUBA1B, and VIM.

21. The method of any one of examples 15 to 17 wherein the one or more target biomarkers are selected from the group consisting of SNCA, BDNF, CNTF, FGF2, GDNF, NGF2, NTF3, PF4, EDN2, ACE2, IFN-γ, ARTN, LIF, CBLN1, NRG1, NRG2, NRG4, PSPN, NTF4, and TGFA.

22. The method of any one of examples 15 to 17 wherein the one or more target biomarkers are selected from the group consisting of NE, CFL1, NPY, DBN, $Ca^{2+}$, renin, DBH, AGT, endothelin 1, 2, and 3, NTS, and APP.

23. A method of determining biomarker activity in a human patient, the method comprising:
transluminally positioning an energy delivery element of a catheter within a target blood vessel of the patient and adjacent to target neural fibers;
at least partially ablating the target neural fibers via the energy delivery element;
capturing a plurality of at least one type of biomarker in a capture compartment of the catheter, wherein the biomarker(s) are secreted as a result of the ablation procedure;
sequestering the plurality of the at least one type of biomarker in the capture compartment to concentrate the biomarker(s);
binding the biomarker(s) to at least one immobilized capture agent disposed on an inner surface of the capture compartment; and
detecting a concentration of the biomarker(s), wherein the concentration corresponds, at least in part, to a degree of ablation of the target neural fibers.

24. The method of example 23 wherein the catheter further comprises a distal filter at a distal end of the capture compartment, and wherein capturing a plurality of at least one type of biomarker in a capture compartment of the catheter comprises allowing passage of the biomarker(s) through the distal filter into the capture compartment, while preventing passage of other biomolecules through the distal filter into the capture compartment.

25. The method of example 23 or example 24 wherein the catheter further comprises a proximal filter at a proximal end of the capture compartment, and wherein capturing a plurality of at least one type of biomarker in a capture compartment of the catheter comprises preventing passage of the biomarker(s) out of the capture compartment through the proximal filter, while allowing blood to flow through the proximal filter and out of the capture compartment.

26. The method of any one of examples 23 to 25 wherein the capture compartment of the catheter is located within the patient while capturing the biomarker(s).

27. The method of any one of examples 23 to 25 wherein the capture compartment of the catheter is located external to the patient while capturing the biomarker(s).

28. A method of monitoring the efficacy of a renal neuromodulation procedure in a human subject, the method comprising:
  determining a baseline level or activity of one or more target biomarkers;
  at least partially inhibiting sympathetic neural activity in a renal nerve of the subject via a neuromodulation assembly;
  determining a post-neuromodulation level or activity for one or more target biomarker; and
  comparing the post-neuromodulation level or activity for the one or more target biomarkers to a pre-determined threshold level or activity, wherein the neuromodulation procedure is classified as successful if the post-neuromodulation level or activity is greater than the pre-determined threshold level or activity.

29. A device for carrying out the method of any one of examples 1 to 28.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for determining biomarker activity in a human subject during a neuromodulation procedure, the method comprising:
  transluminally delivering a distal portion of an elongated shaft of a catheter to a target renal blood vessel of the human subject;
  determining a baseline level of one or more biomarkers in bodily fluid collected from the human subject;
  at least partially inhibiting sympathetic neural activity in a renal nerve of the human subject via energy delivered by a neuromodulation assembly carried by the distal portion of the elongated shaft;
  intravascularly obtaining a volume of bodily fluid including the one or more biomarkers using a capture compartment of the catheter within 30 minutes post-neuromodulation;
  determining a post-neuromodulation level for the one or more biomarkers in the volume of bodily fluid including the one or more biomarkers using an analyzer operatively coupled to the elongated shaft; and
  comparing the post-neuromodulation level to the baseline level prior to removing the neuromodulation assembly from the human subject, wherein the neuromodulation procedure is classified as at least partially successful if the post-neuromodulation level differs significantly from the baseline level.

2. The method of claim 1 wherein the one or more biomarkers includes a catecholamine metabolite.

3. The method of claim 1 wherein the one or more biomarkers includes neuropeptide Y in plasma collected from the human subject.

4. The method of claim 1 wherein the one or more biomarkers includes vasopressin in plasma collected from the human subject.

5. The method of claim 1 wherein the one or more biomarkers is selected from a group consisting of epinephrine, dopamine, neuropeptide Y, vasopressin, and a secreted catecholamine metabolite.

6. The method of claim 1 wherein the one or more biomarkers includes a component of a renin-angiotensin aldosterone system in plasma collected from the human subject, and wherein the component of the renin-angiotensin aldosterone system is selected from aldosterone, angiotensin, angiotensin converting enzyme (ACE), kalakrein B1 (KLKB1) and natriuretic peptide B (BNP).

7. The method of claim 6 wherein the component of the renin-angiotensin aldosterone system is aldosterone.

8. The method of claim 1 wherein the baseline level is higher than the post-neuromodulation level.

9. The method of claim 1 wherein the baseline level is lower than the post-neuromodulation level.

10. The method of claim 1 wherein the neuromodulation procedure is classified as at least partially successful if the post-neuromodulation level differs at least about 5% from the baseline level.

11. The method of claim 1 wherein the neuromodulation procedure is classified as at least partially successful if the post-neuromodulation level is at least about 50% lower than the baseline level.

12. The method of claim 1 wherein the neuromodulation procedure is classified as at least partially successful if the post-neuromodulation level differs from the baseline level by at least about 2-fold.

13. The method of claim 1 wherein the post-neuromodulation level is a first post neuromodulation level, and wherein the method comprises determining a second post-neuromodulation level of the one or more biomarkers at about 1 month, about 3 months, or about 6 months post-neuromodulation, and wherein the neuromodulation procedure is classified as at least partially successful if the second post-neuromodulation level is lower than the baseline level and the first post-neuromodulation level.

14. The method of claim 1 wherein at least partially inhibiting sympathetic neural activity in a renal nerve of the human subject via energy comprises delivering energy selected from a group consisting of radio frequency (RF) energy, pulsed RF energy, microwave energy, laser light energy, optical energy, ultrasound energy, high-intensity focused ultrasound energy, magnetic energy, direct heat energy, and cryotherapeutic energy.

15. The method of claim 1 wherein at least partially inhibiting sympathetic neural activity in a renal nerve of the human subject via energy comprises delivering thermal energy.

16. The method of claim 1, wherein the comparing the post-neuromodulation level to the baseline level is done for two or more of the biomarkers.

* * * * *